US012582420B2

(12) United States Patent
Cundiff et al.

(10) Patent No.: US 12,582,420 B2
(45) Date of Patent: Mar. 24, 2026

(54) OSTEOTOMY CUTTING SYSTEMS AND SURGICAL TECHNIQUES

(71) Applicant: Fusion Orthopedics USA, LLC, Mesa, AZ (US)

(72) Inventors: Adam J. Cundiff, Gilbert, AZ (US); Nathan G. Peterson, Gilbert, AZ (US); Eli W. Jacobson, Chandler, AZ (US); Sergio H. Urquiza, Plainfield, IL (US)

( * ) Notice: Subject to any disclaimer, the term of this patent is extended or adjusted under 35 U.S.C. 154(b) by 67 days.

(21) Appl. No.: 18/182,672

(22) Filed: Mar. 13, 2023

(65) Prior Publication Data

US 2023/0255651 A1     Aug. 17, 2023

Related U.S. Application Data

(63) Continuation-in-part of application No. 17/897,972, filed on Aug. 29, 2022, which is a continuation-in-part of application No. 17/182,136, filed on Feb. 22, 2021, now Pat. No. 11,439,415.

(60) Provisional application No. 63/115,205, filed on Nov. 18, 2020.

(51) Int. Cl.
*A61B 17/17*     (2006.01)
*A61B 17/02*     (2006.01)

(52) U.S. Cl.
CPC ........ *A61B 17/1775* (2016.11); *A61B 17/025* (2013.01)

(58) Field of Classification Search
CPC ........................ A61B 17/1775; A61B 17/025
See application file for complete search history.

(56) References Cited

U.S. PATENT DOCUMENTS

| | | | |
|---|---|---|---|
| 2013/0090662 A1* | 4/2013 | Hanson ................. | A61B 90/00 606/86 R |
| 2016/0199076 A1* | 7/2016 | Fallin ................. | A61B 17/1739 606/301 |
| 2016/0213384 A1* | 7/2016 | Fallin ................... | A61B 17/151 |
| 2016/0235414 A1* | 8/2016 | Hatch ................ | A61B 17/1739 |
| 2017/0014173 A1* | 1/2017 | Smith ................ | A61B 17/1775 |
| 2018/0256210 A1* | 9/2018 | Mullaney .............. | A61B 17/68 |
| 2022/0313287 A1* | 10/2022 | Woodard .............. | A61B 17/90 |

* cited by examiner

*Primary Examiner* — Christian A Sevilla

(57) ABSTRACT

Osteotomy cutting systems and surgical methods are provided herein. One surgical method includes coupling, to a cuneiform of a subject, a surgical apparatus for use in facilitating correction of a bunion and coupling the surgical apparatus to another bone of the subject. Another surgical method includes coupling a surgical apparatus to a cuneiform and metatarsal of a subject, coupling a cutting block for alignment at a joint between the cuneiform and the metatarsal, and performing a surgical procedure utilizing the surgical apparatus and the cutting block to correct a bunion. A further surgical method includes providing a surgical apparatus for use in facilitating correction of a bunion in a subject in which the surgical apparatus is configured to couple to a cuneiform and a metatarsal of the subject and performing a surgical procedure utilizing the surgical apparatus while the surgical apparatus is coupled to the cuneiform and the metatarsal.

12 Claims, 56 Drawing Sheets

4000

900

4000

900

OSTEOTOMY CUTTING SYSTEM 5100

SURGICAL CUTTING BLOCK
5102

POSITIONING GUIDE
5104

SURGICAL JIG
5106

ATTACH SURGICAL JIG TO CUNEIFORM ⟶ 5202

ALIGN JIG WITH METATARSAL ⟶ 5204

CORRECT INTERMETATARSAL ANGLE OF METATARSAL ⟶ 5206/5208

ROTATE METATARSAL ⟶ 5208/5206

LOCK POSITION OF METATARSAL ⟶ 5210

PLACE POSITIONING GUIDE INTO CUNEIFORM-METATARSAL JOINT ⟶ 5212

ALIGN CUTTING BLOCK WITH TARGET JOINT AND POSITIONING GUIDE ⟶ 5214

SECURE CUTTING BLOCK ⟶ 5216

REMOVE POSITIONING GUIDE ⟶ 5218

A

5300A

ATTACH SURGICAL JIG TO CUNEIFORM — 5302

ALIGN JIG WITH METATARSAL — 5304

LOCK IN ALIGNMENT OF JIG AND METATARSAL — 5306

CORRECT INTERMETATARSAL ANGLE OF METATARSAL — 5308/ 5310

ROTATE METATARSAL — 5310/ 5308

LOCK IN POSITION OF METATARSAL — 5312

SURGICALLY CUT BONE — 5314

DISTRACT TARGET JOINT — 5316

REMOVE LEFTOVER CUT BONE — 5318

A

6200

ATTACH A FIXATION DEVICE TO A FIRST METATARSAL — 6202

APPLY A FORCE TO THE FIXATION DEVICE VIA A POSITIONING DEVICE TO MOVE THE FIRST METATARSAL — 6204

RELEASE THE MOVED FIRST METATARSAL FROM A TARSOMETATARSAL JOINT — 6206

OSTEOTOMY CUTTING SYSTEMS AND SURGICAL TECHNIQUES

REFERENCE TO RELATED APPLICATION

This application is a Continuation-In-Part of and claims priority to U.S. patent application Ser. No. 17/897,972, now U.S. Pat. No. 12,369,931, filed on Aug. 29, 2022, which is a Continuation-In-Part of and claims priority to U.S. patent application Ser. No. 17/182,136, now U.S. Pat. No. 11,439, 415, filed on Feb. 22, 2021, which claims priority to and the benefit of U.S. Provisional Patent Application No. 63/115, 205, filed on Nov. 18, 2020, the contents of each of which are incorporated herein by reference in their entirety.

FIELD OF THE TECHNOLOGY

The present technology relates generally to surgical instruments and techniques, and more particularly to, osteotomy cutting systems and surgical techniques.

BACKGROUND

Different surgical procedures utilize different instruments and techniques. In an osteotomy for correcting a bunion, for example, the surgeon makes multiple cuts to the bone to realign the joint using multiple surgical cutting blocks that each include a single cutting guide. That is, each time that a new cut is needed to be made to the hone, the surgeon must move the surgical cutting block to a new location or use a different surgical cutting block at the new location to make the cut, both of which are time consuming and/or an inefficient use of surgical instrumentation.

SUMMARY

Osteotomy cutting systems and surgical methods are provided herein. One surgical method includes coupling, to a cuneiform of a subject, a surgical apparatus for use in facilitating correction of a bunion in the subject in which the cuneiform is a first bone of the subject and coupling the surgical apparatus to a second bone of the subject.

Another surgical method includes coupling a surgical apparatus to a cuneiform and a metatarsal of a subject, coupling a cutting block for alignment at a joint between the cuneiform and the metatarsal of the subject. The method further includes performing a surgical procedure utilizing the surgical apparatus and the cutting block to correct a bunion in the subject.

A further surgical method includes providing a surgical apparatus for use in facilitating correction of a bunion in a subject in which the surgical apparatus is configured to couple to a cuneiform and a metatarsal of the subject. The method further includes performing a surgical procedure utilizing the surgical apparatus while the surgical apparatus is coupled to the cuneiform and the metatarsal of the subject.

BRIEF DESCRIPTION OF THE DRAWINGS

To readily understand the advantages and benefits of the technology, a more particular description of the technology briefly described above will be rendered by reference to specific embodiments that are illustrated in the appended drawings. Understanding that these drawings depict typical embodiments of the technology, and are therefore not to be considered to be limiting of its scope, the technology will be described and explained with additional specificity and detail through the use of the accompanying drawings, in which:

FIG. 51 is a block diagram illustrating one embodiment of an osteotomy cutting system;

DETAILED DESCRIPTION OF THE DRAWINGS

It should be understood that the language used in the present disclosure has been principally selected for readability and instructional purposes, and not to limit the scope of the subject matter disclosed herein in any manner. Further, reference throughout this specification to "one embodiment," "an embodiment," or similar language means that a particular feature, structure, or characteristic described in connection with the embodiment is included in at least one embodiment. Thus, appearances of the phrases "in one embodiment," "in an embodiment," and similar language throughout this specification may, but do not necessarily, all refer to the same embodiment, but mean "one or more but not all embodiments" unless expressly specified otherwise. The terms "including," "comprising," "having," and variations thereof mean "including, but not limited to" unless expressly specified otherwise. An enumerated listing of items does not imply that any or all of the items are mutually exclusive and/or mutually inclusive, unless expressly specified otherwise. The terms "a," "an," and "the" also refer to "one or more" unless expressly specified otherwise.

In addition, as used herein, the term "set" can mean "one or more," unless expressly specified otherwise. The term "sets" can mean multiples of or a plurality of "one or mores," "ones or more," and/or "ones or mores" consistent with set theory, unless expressly specified otherwise.

Furthermore, the described features, advantages, and characteristics of the embodiments may be combined in any suitable manner. One skilled in the relevant art will recognize that the embodiments may be practiced without one or more of the specific features or advantages of a particular embodiment. In other instances, additional features and advantages may be recognized in certain embodiments that may not be present in all embodiments.

Furthermore, the described features, structures, or characteristics of the various embodiments disclosed herein may be combined in any suitable manner. One skilled in the relevant art will recognize, however, that embodiments may be practiced without one or more of the specific details, or with other methods, components, materials, and so forth. In other instances, well-known structures, and/or materials are not shown or described in detail to avoid obscuring aspects of an embodiment.

Various embodiments provide osteotomy cutting systems surgical techniques. Some osteotomy cutting systems include a surgical cutting block, a positioning guide, and/or a surgical jig. Various surgical techniques perform an osteotomy using one embodiment of an osteotomy cutting system.

Figure 1:
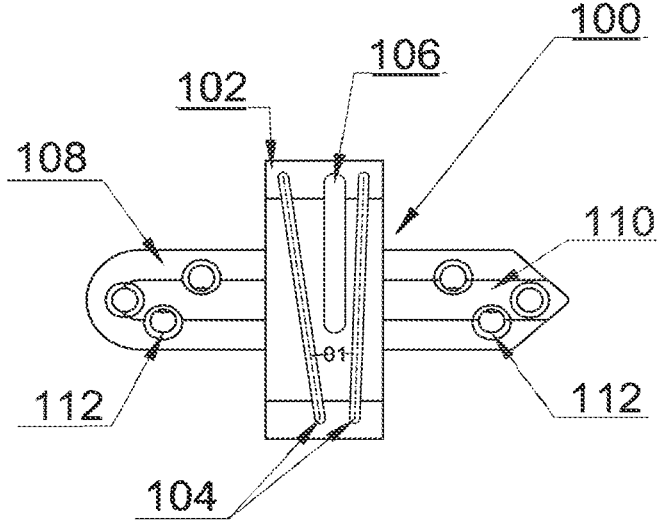
FIG. 1 is a diagram illustrating one embodiment of a surgical cutting block including a plurality of single cut guides.

Turning now to the drawings, FIG. 1 is a diagram illustrating one embodiment of a surgical cutting block 100. At least in the illustrated embodiment, the surgical cutting block 100 includes, among other components, a cutting platform 102 (or cutting portion 102) including a plurality of single cut guides 104 (e.g., cutting slots) formed thereon, a positioning slot 106 (e.g., an aperture), a cuneiform fixation platform 108, a metatarsal fixation platform 110, and a plurality of wire holes 112.

The cutting platform 102 may be formed of any suitable material. In certain embodiments, the material included in and/or forming the cutting platform 102 is sterilizable.

In the embodiment illustrated in FIG. 1, the plurality of single cut guides 104 includes a single cut guide 104 located on opposite sides of the positioning slot 106. Other embodiments may include the plurality of single cut guides 104 positioned at other locations on the cutting platform 102 (e.g., on the same side of the positioning slot 106, among other locations that are possible and contemplated herein). That is, the plurality of single cut guides 104 may be positioned/formed at any suitable location on the cutting platform 102.

The single cut guides 104 each include a size and/or width capable of accepting a surgical cutting tool (e.g., a scalpel, surgical knife, etc.) and provide a single path for the surgical cutting tool to follow while the surgical cutting tool is being used to produce an incision in a patient. Each single cut guide 104 includes an angle ($\theta$), which can be any suitable angle (e.g., an angle ($\theta$) in the range of about one degree (1°) to about 90 degrees)(90°) with respect to any suitable reference point that can provide a predetermined and/or target path for the surgical cutting tool to follow while the surgical cutting tool is cutting a patient and/or performing a surgical procedure.

In some embodiments, all of the single cut guides 104 are angled in the same direction (e.g., angled toward the left or toward the right with respect to the user (e.g., a medical professional)). In the illustrated embodiment, all of the single cut guides 104 are angled in the different directions (see, e.g., FIG. 1).

In additional or alternative embodiments, a pair of single cut guides 104 are positioned on the cutting platform 102 such that there is an angle ($\theta_1$) created between the pair of single cut guides 104, which may be any suitable angle ($\theta_1$). In various embodiments, the angle ($\theta_1$) is in the range of about fifteen degrees (15°) to about 75 degrees (75°).

The positioning slot 106 is configured to facilitate positioning the surgical cutting block 100 over a target surgical area. The positioning slot 106 may include any suitable size and/or shape that can facilitate positioning the surgical cutting block 100 over a target surgical area.

A cuneiform fixation platform 108 may include any suitable size, shape, and/or material(s) that can facilitate fixating the surgical cutting block 100 to a cuneiform. In certain embodiments, the cuneiform fixation platform 108 is located on a side of the cutting platform 102, among other locations that are possible and contemplated herein.

A metatarsal fixation platform 110 may include any suitable size, shape, and/or material(s) that can facilitate fixating the surgical cutting block 100 to a metatarsal. In various embodiments, the metatarsal fixation platform 110 is located on a side of the cutting platform 102, among other locations that are possible and contemplated herein. In some embodiments, the cuneiform fixation platform 108 is located on one side of the cutting platform 102 and the metatarsal fixation platform 110 is located on the other side of the cutting platform 102 opposite the cuneiform fixation platform 108, among other locations and/or relative positions that are possible and contemplated herein.

In some embodiments, the cuneiform fixation platform 108 and the metatarsal fixation platform 110 include a set of wire holes 112 formed respectively therein. Each of the he cuneiform fixation platform 108 and the metatarsal fixation platform 110 include one or more wire holes 112 for attaching the surgical cutting block 100 to a cuneiform and a metatarsal, respectively, which can be any suitable quantity of wire holes 112. Further, the wire holes 112 may include any suitable size and/or shape that can facilitate fixating the surgical cutting block 100 to a cuneiform and a metatarsal via a pin passing through the wire holes 112 on the cuneiform fixation platform 108 and the metatarsal fixation platform 110, respectively.

Figure 2:
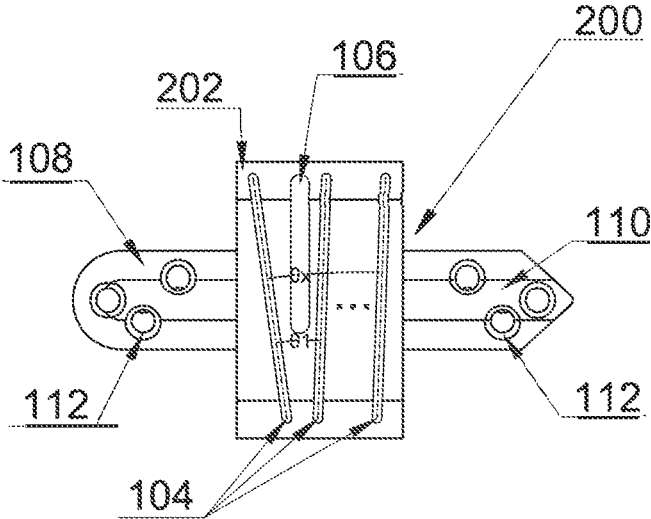
FIG. 2 is a diagram illustrating another embodiment of a surgical cutting block including a plurality of single cut guides.

FIG. 2 is a diagram illustrating another embodiment of a surgical cutting block 200 including a plurality of single cut guides 104. In this embodiment, a sub-plurality of single cut guides 104 are positioned/located on a cutting platform 202 on the side of the positioning slot 106 toward the metatarsal fixation platform 110. Further, surgical cutting block 200 includes one single cut guide 104 positioned/located on the cutting platform 202 on the side of the positioning slot 106 toward the cuneiform fixation platform 108.

In some embodiments, all of the single cut guides 104 are angled in the same direction (e.g., angled toward the left or toward the right with respect to the user (e.g., a medical professional)). In the illustrated embodiment, all of the single cut guides 104 on the same side of the positioning slot 106 are angled in the same direction and in a different direction than the single cut guide 104 on the other side of the positioning slot 106.

In additional or alternative embodiments, the single cut guides 104 are positioned on the cutting platform 202 such that there is an angle ($\theta_1$) and ($\theta_x$) created between the sub-plurality of single cut guides 104 and the one single cut guide 104, which may be any suitable angle. In various embodiments, the respective angles ($\theta_1$) and ($\theta_x$) may each be in the range of about fifteen degrees (15°) to about 75 degrees (75°).

Figure 3:
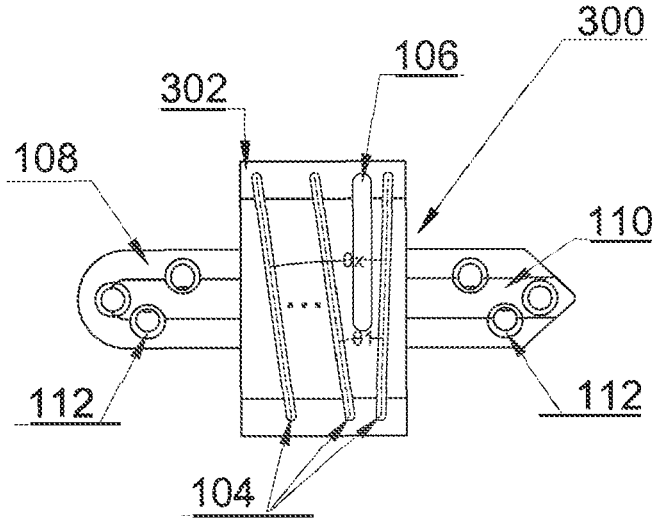
FIG. 3 is a diagram illustrating yet another embodiment of a surgical cutting block including a plurality of single cut guides.

FIG. 3 is a diagram illustrating yet another embodiment of a surgical cutting block 300 including a plurality of single cut guides 104. In this embodiment, a sub-plurality of single cut guides 104 are positioned/located on a cutting platform 302 on the side of the positioning slot 106 toward the cuneiform fixation platform 108. Further, surgical cutting block 300 includes one single cut guide 104 positioned/located on the cutting platform 302 on the side of the positioning slot 106 toward the metatarsal fixation platform 110.

In some embodiments, all of the single cut guides 104 are angled in the same direction (e.g., angled toward the left or toward the right with respect to the user (e.g., a medical professional)). In the illustrated embodiment, all of the single cut guides 104 on the same side of the positioning slot 106 are angled in the same direction and in a different direction than the single cut guide 104 on the other side of the positioning slot 106.

In additional or alternative embodiments, the single cut guides 104 are positioned on the cutting platform 302 such that there is an angle ($\theta_1$) and ($\theta_x$) created between the sub-plurality of single cut guides 104 and the one single cut guide 104, which may be any suitable angle. In various embodiments, the respective angles ($\theta_1$) and ($\theta_x$) may each be in the range of about 15° to about 75°.

Figure 4:
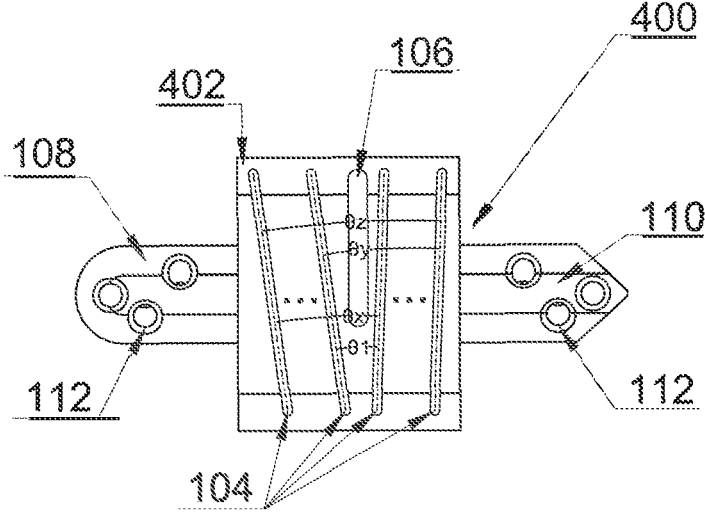
FIG. 4 is a diagram illustrating still another embodiment of a surgical cutting block including a plurality of single cut guides.

FIG. 4 is a diagram illustrating still another embodiment of a surgical cutting block 400 including a plurality of single cut guides 104. In this embodiment, a sub-plurality of single cut guides 104 are positioned/located on a cutting platform 402 on the side of the positioning slot 106 toward the metatarsal fixation platform 110. Further, surgical cutting block 400 includes a sub-plurality of single cut guides 104 positioned/located on the cutting platform 102 on the side of the positioning slot 106 toward the cuneiform fixation platform 108.

In some embodiments, all of the single cut guides 104 are angled in the same direction (e.g., angled toward the left or toward the right with respect to the user (e.g., a medical professional)). In the illustrated embodiment, all of the single cut guides 104 on the same side of the positioning slot 106 are angled in the same direction and in a different direction than the single cut guides 104 on the other side of the positioning slot 106.

In additional or alternative embodiments, the single cut guides 104 are positioned on the cutting platform 402 such that there is an angle ($\theta_1$), ($\theta_x$), ($\theta_y$), and ($\theta_z$) created between the sub-plurality of single cut guides 104 located on each side of the positioning slot 106, which may be any suitable angle. In various embodiments, the respective angles ($\theta_1$), ($\theta_x$), ($\theta_y$), and ($\theta_z$) may each be in the range of about 15° to about 75°.

Figure 5:
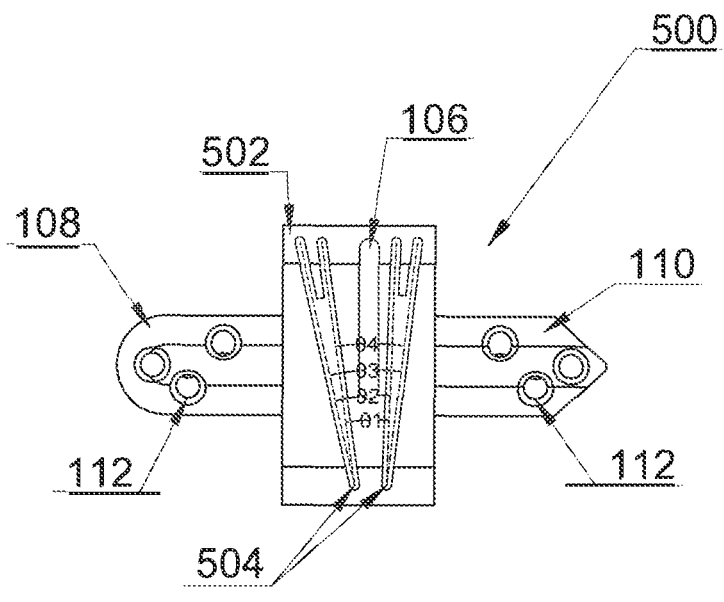
FIG. 5 is a diagram illustrating one embodiment of a surgical cutting block including a plurality of double cut guides.

FIG. 5 is a diagram illustrating one embodiment of a surgical cutting block 500 including a plurality of double cut guides 104. In this embodiment, a double cut guide 504 is positioned/located on a cutting platform 502 on each side of the positioning slot 106, among other positions that are possible and contemplated herein.

The double cut guides 504 each include a pair of paths that can include any suitable size and/or width capable of accepting a surgical cutting tool (e.g., a scalpel, surgical knife, etc.) and provide a respective path for the surgical cutting tool to follow while the surgical cutting tool is being used to produce an incision in a patient. Each double cut guide 504 includes an angle, which can be any suitable angle (e.g., an angle in the range of about one degree (1°) to about 90 degrees)(90°) with respect to any suitable reference point that can provide a predetermined and/or target path for the surgical cutting tool to follow while the surgical cutting tool is cutting a patient and/or performing a surgical procedure.

In some embodiments, all of the double cut guides 504 are angled in the same direction (e.g., angled toward the left or toward the right with respect to the user (e.g., a medical professional)). In the illustrated embodiment, all of the double cut guides 504 are angled in the different directions.

In additional or alternative embodiments, a pair of double cut guides 504 are positioned on the cutting platform 502 such that there is an angle ($\theta_1$), ($\theta_2$), ($\theta_3$), and ($\theta_4$) created between the double cut guides 504 located on each side of the positioning slot 106, which may be any suitable angle. In various embodiments, the respective angles ($\theta_1$), ($\theta_2$), ($\theta_3$), and ($\theta_4$) may each be in the range of about 15° to about 75°.

Figure 6:
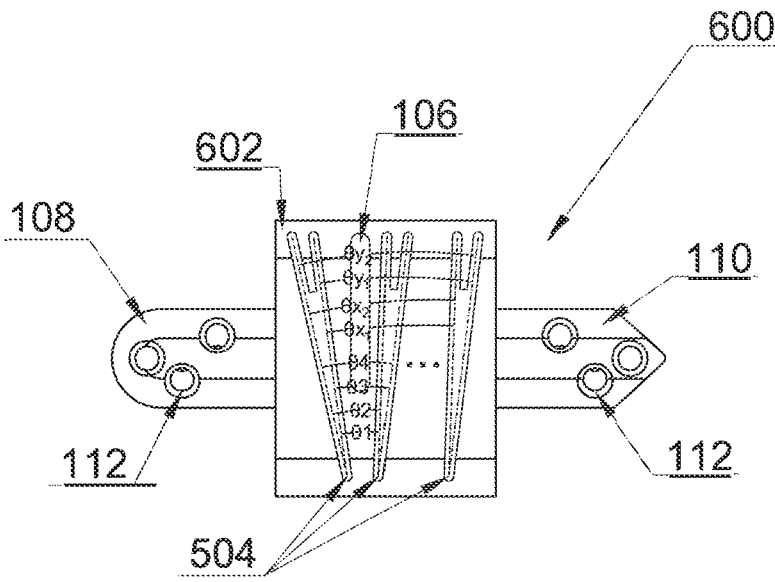
FIG. 6 is a diagram illustrating another embodiment of a surgical cutting block including a plurality of double cut guides.

FIG. 6 is a diagram illustrating another embodiment of a surgical cutting block 600 including a plurality of double cut guides 504. In this embodiment, a sub-plurality of double cut guides 504 are positioned/located on a cutting platform 602 on the side of the positioning slot 106 toward the metatarsal fixation platform 110. Further, surgical cutting block 600 includes one double cut guide 504 positioned/located on the cutting platform 602 on the side of the positioning slot 106 toward the cuneiform fixation platform 108.

In some embodiments, all of the double cut guides 504 are angled in the same direction (e.g., angled toward the left or toward the right with respect to the user (e.g., a medical professional)). In the illustrated embodiment, all of the double cut guides 504 on the same side of the positioning slot 106 are angled in the same direction and in a different direction than the double cut guide 504 on the other side of the positioning slot 106.

In additional or alternative embodiments, the double cut guides 504 are positioned on the cutting platform 602 such that there is an ($\theta_1$), ($\theta_2$), ($\theta_3$), ($\theta_4$), ($\theta_{x1}$), ($\theta_{x2}$), ($\theta_{y1}$), and $(\theta_{y2})$ created between the double cut guides 504 located on each side of the positioning slot 106, which may be any suitable angle. In various embodiments, the respective angles $(\theta_1)$, $(\theta_2)$, $(\theta_3)$, $(\theta_4)$, $(\theta_{x1})$, $(\theta_{x2})$, $(\theta_{y1})$, and $(\theta_{y2})$ may each be in the range of about 15° to about 75°.

Figure 7:
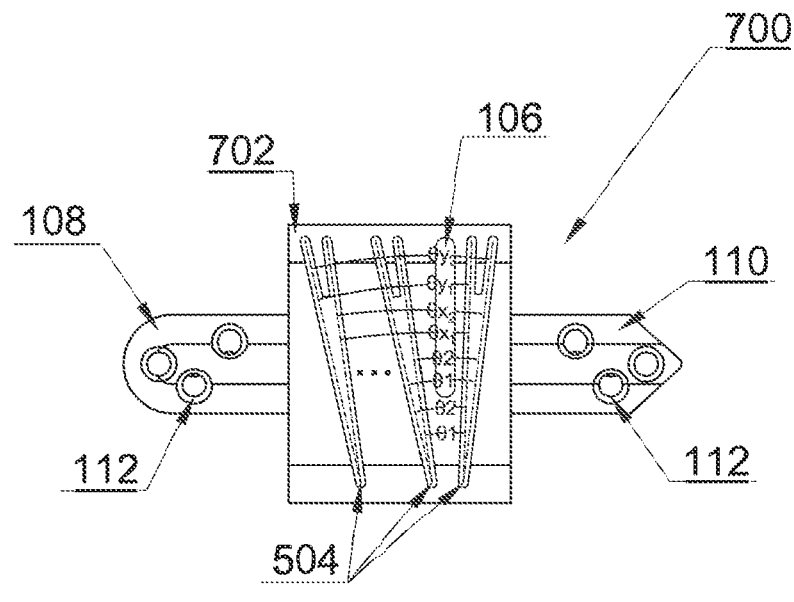
FIG. 7 is a diagram illustrating yet another embodiment of a surgical cutting block including a plurality of double cut guides.

FIG. 7 is a diagram illustrating another embodiment of a surgical cutting block 700 including a plurality of double cut guides 504. In this embodiment, a sub-plurality of double cut guides 504 are positioned/located on a cutting platform 702 on the side of the positioning slot 106 toward the cuneiform fixation platform 108. Further, surgical cutting block 700 includes one double cut guide 504 positioned/located on the cutting platform 702 on the side of the positioning slot 106 toward the metatarsal fixation platform 110.

In some embodiments, all of the double cut guides 504 are angled in the same direction (e.g., angled toward the left or toward the right with respect to the user (e.g., a medical professional)). In the illustrated embodiment, all of the double cut guides 504 on the same side of the positioning slot 106 are angled in the same direction and in a different direction than the double cut guide 504 on the other side of the positioning slot 106.

In additional or alternative embodiments, the double cut guides 504 are positioned on the cutting platform 702 such that there is an $(\theta_1)$, $(\theta_2)$, $(\theta_3)$, $(\theta_4)$, $(\theta_{x1})$, $(\theta_{x2})$, $(\theta_{y1})$, and $(\theta_{y2})$ created between the double cut guides 504 located on each side of the positioning slot 106, which may be any suitable angle. In various embodiments, the respective angles $(\theta_1)$, $(\theta_2)$, $(\theta_3)$, $(\theta_4)$, $(\theta_{x1})$, $(\theta_{x2})$, $(\theta_{y1})$, and $(\theta_{y2})$ may each be in the range of about 15° to about 75°.

Figure 8:
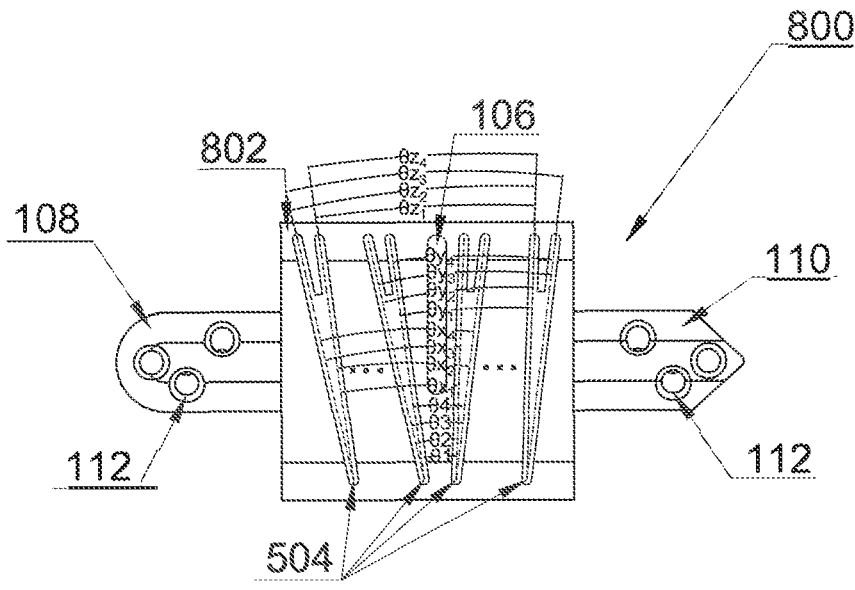
FIG. 8 is a diagram illustrating still another embodiment of a surgical cutting block including a plurality of double cut guides.

FIG. 8 is a diagram illustrating another embodiment of a surgical cutting block 800 including a plurality of double cut guides 504. In this embodiment, a sub-plurality of double cut guides 504 are positioned/located on a cutting platform 802 on both sides of the positioning slot.

In some embodiments, all of the double cut guides 504 are angled in the same direction (e.g., angled toward the left or toward the right with respect to the user (e.g., a medical professional)). In the illustrated embodiment, all of the double cut guides 504 on the same side of the positioning slot 106 are angled in the same direction and in a different direction than the double cut guides 504 on the other side of the positioning slot 106.

In additional or alternative embodiments, the double cut guides 504 are positioned on the cutting platform 802 such that there is an angle $(\theta_1)$, $(\theta_2)$, $(\theta_3)$, $(\theta_4)$, $(\theta_{x1})$, $(\theta_{x2})$, $(\theta_{x3})$, $(\theta_{x4})$, $(\theta_{y1})$, $(\theta_{y2})$, $(\theta_{y3})$, and $(\theta_{y4})$ created between the double cut guides 504 located on each side of the positioning slot 106, which may be any suitable angle. In various embodiments, the respective angles $\theta_1)$, $(\theta_2)$, $(\theta_3)$, $(\theta_4)$, $(\theta_{x1})$, $(\theta_{x2})$, $(\theta_{x3})$, $(\theta_{x4})$, $(\theta_{y1})$, $(\theta_{y2})$, $(\theta_{y3})$, and $(\theta_{y4})$ may each be in the range of about 15° to about 75°.

Figure 9A:
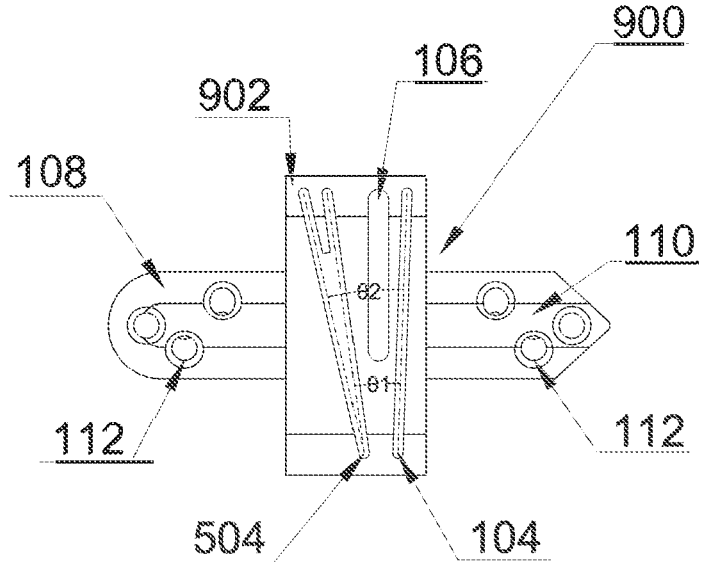
FIG. 9A is diagram illustrating a top view of one embodiment of a surgical cutting block including a single cut guide and a double cut guide.

FIG. 9A is a diagram illustrating one embodiment of a surgical cutting block 900 including a single cut guide 104 and a double cut guide 504. In this embodiment, the single cut guide 104 is positioned/located on a cutting platform 902 on the side of the positioning slot 106 toward the metatarsal fixation platform 110. Further, surgical cutting block 900 includes the double cut guide 504 positioned/located on the cutting platform 902 on the side of the positioning slot 106 toward the cuneiform fixation platform 108.

In some embodiments, the single cut guide 104 and the double cut guide 504 are angled in the same direction (e.g., angled toward the left or toward the right with respect to the user (e.g., a medical professional)). In the illustrated embodiment, the single cut guide 104 and the double cut guide 504 are angled in different directions.

In additional or alternative embodiments, the single cut guide 104 and the double cut guide 504 are positioned on the cutting platform 902 such that there is an angle $(\theta_1)$ and $(\theta_2)$ created between the single cut guide 104 and the double cut guide 504, which may be any suitable angle. In various embodiments, the respective angles $(\theta_1)$ and $(\theta_2)$ may each be in the range of about 15° to about 75°.

Figure 9B:
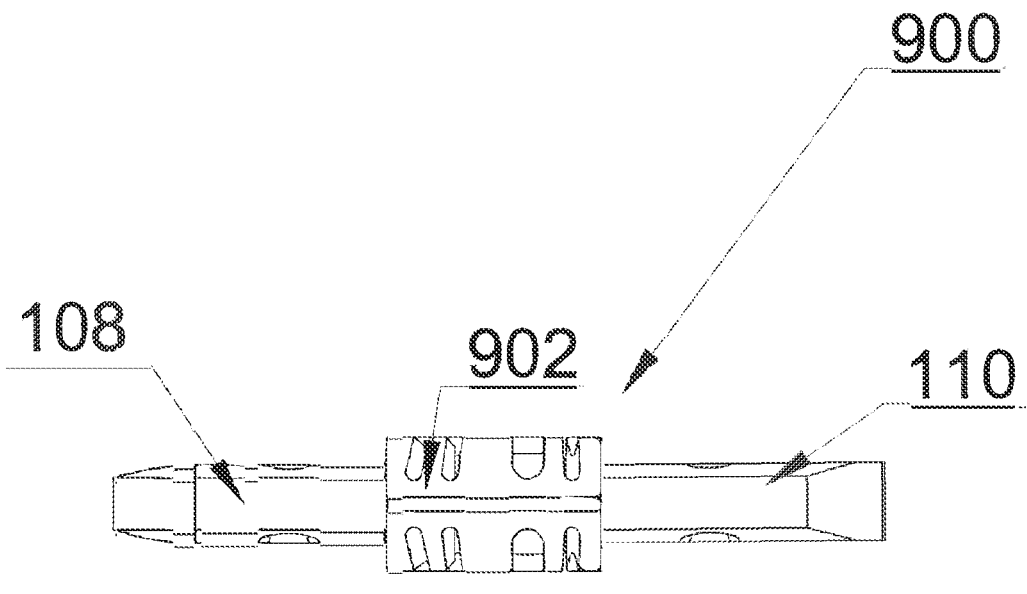
FIG. 9B is diagram illustrating a side profile of the surgical cutting block illustrated in FIG. 9A.

FIG. 9B is diagram illustrating a side profile of the surgical cutting block 900. FIG. 9B illustrates that a single cut guide 104 (e.g., an aperture) and a double cut guide 504 (e.g., an aperture) extend through the cutting platform 902.

Figure 9C:
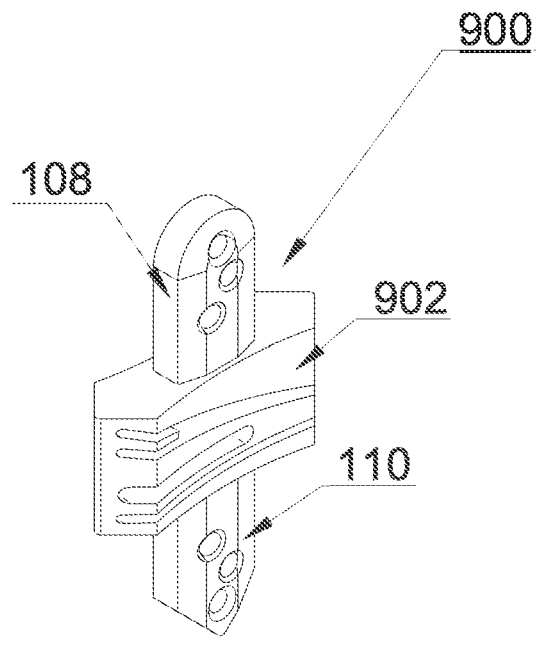
FIG. 9C is a diagram illustrating side view of the surgical cutting block illustrated in FIGS. 9A and 9B.

FIG. 9C is a diagram illustrating side view of the surgical cutting block 900. FIG. 9C illustrates that the cutting platform 902 may include a slope and/or sloped portion that can be any suitable slope included at any suitable portion of the cutting platform.

Figure 10:
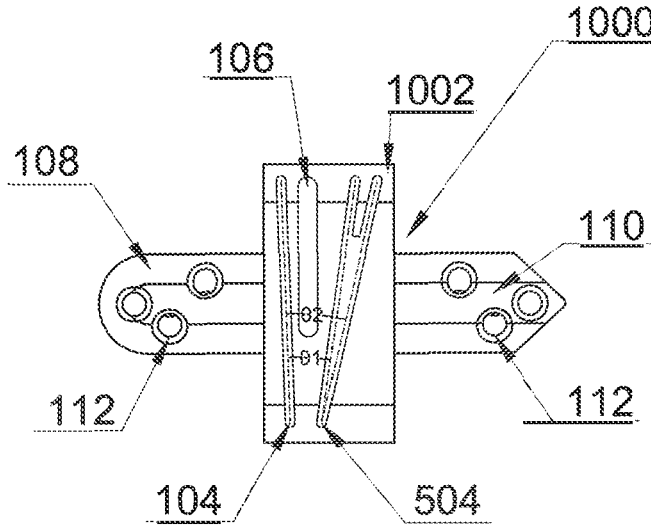
FIG. 10 is a diagram illustrating another embodiment of a surgical cutting block including a single cut guide and a double cut guide.

FIG. 10 is a diagram illustrating another embodiment of a surgical cutting block 1000 including a single cut guide 104 and a double cut guide 504. In this embodiment, the single cut guide 104 is positioned/located on a cutting platform 1002 on the side of the positioning slot 106 toward the cuneiform fixation platform 108. Further, surgical cutting block 1000 includes the double cut guide 504 positioned/located on the cutting platform 1002 on the side of the positioning slot 106 toward the metatarsal fixation platform 110.

In some embodiments, the single cut guide 104 and the double cut guide 504 are angled in the same direction (e.g., angled toward the left or toward the right with respect to the user (e.g., a medical professional)). In the illustrated embodiment, the single cut guide 104 and the double cut guide 504 are angled in different directions.

In additional or alternative embodiments, the single cut guide 104 and the double cut guide 504 are positioned on the cutting platform 102 such that there is an angle $(\theta_1)$ and $(\theta_2)$ created between the single cut guide 104 and the double cut guide 504, which may be any suitable angle. In various embodiments, the respective angles $(\theta_1)$ and $(\theta_2)$ may each be in the range of about 15° to about 75°.

Figure 11:
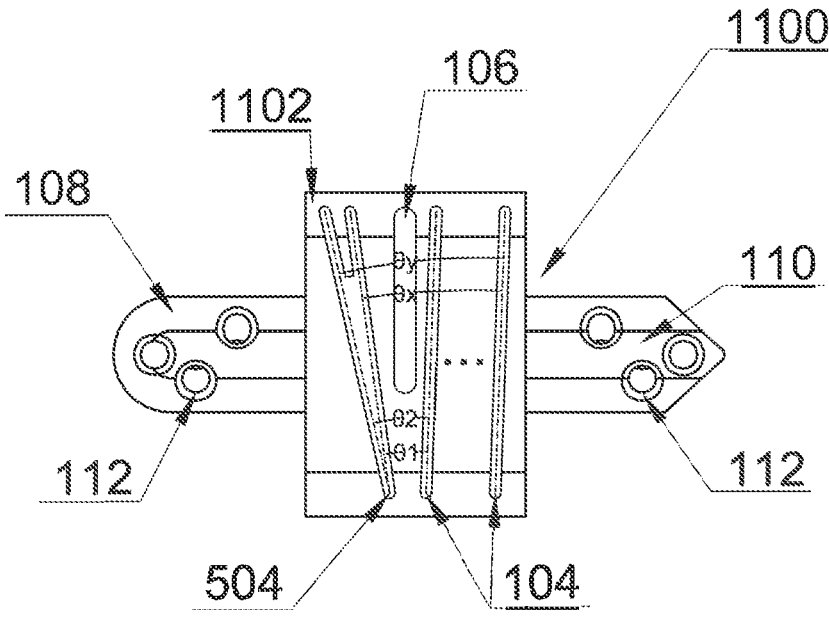
FIG. 11 is a diagram illustrating one embodiment of a surgical cutting block including a plurality of single cut guides and a double cut guide.

FIG. 11 is a diagram illustrating one embodiment of a surgical cutting block 1100 including a plurality of single cut guides 104 and a double cut guide 504. In this embodiment, the plurality of single cut guides 104 are positioned/located on a cutting platform 1102 on the side of the positioning slot 106 toward the metatarsal fixation platform 110. Further, surgical cutting block 1100 includes the double cut guide 504 positioned/located on the cutting platform 1102 on the side of the positioning slot 106 toward the cuneiform fixation platform 108.

In some embodiments, the plurality of single cut guides 104 and the double cut guide 504 are angled in the same direction (e.g., angled toward the left or toward the right with respect to the user (e.g., a medical professional)). In the illustrated embodiment, the plurality of single cut guides 104 and the double cut guide 504 are angled in different directions.

In additional or alternative embodiments, the plurality of single cut guides 104 and the double cut guide 504 are positioned on the cutting platform 1102 such that there is an angle $(\theta_1)$, $(\theta_2)$, $(\theta_x)$, and $(\theta_y)$ created between the plurality of single cut guides 104 and the double cut guide 504, which may be any suitable angle. In various embodiments, the respective angles $(\theta_1)$, $(\theta_2)$, $(\theta_x)$, and $(\theta_y)$ may each be in the range of about 15° to about 75°.

Figure 12:
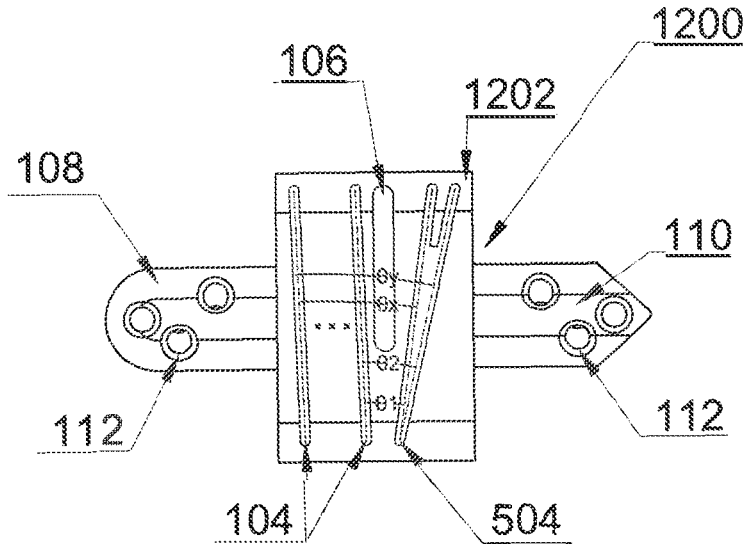
FIG. 12 is a diagram illustrating another embodiment of a surgical cutting block including a plurality of single cut guides and a double cut guide.

FIG. 12 is a diagram illustrating another embodiment of a surgical cutting block including a plurality of single cut guides 104 and a double cut guide 504. In this embodiment, the plurality of single cut guides 104 are positioned/located on a cutting platform 1202 on the side of the positioning slot 106 toward the cuneiform fixation platform 108. Further, surgical cutting block 1200 includes the double cut guide 504 positioned/located on the cutting platform 1202 on the side of the positioning slot 106 toward the metatarsal fixation platform 110.

In some embodiments, the plurality of single cut guides 104 and the double cut guide 504 are angled in the same direction (e.g., angled toward the left or toward the right with respect to the user (e.g., a medical professional)). In the illustrated embodiment, the plurality of single cut guides 104 and the double cut guide 504 are angled in different directions.

In additional or alternative embodiments, the plurality of single cut guides 104 and the double cut guide 504 are positioned on the cutting platform 1202 such that there is an angle $(\theta_1)$, $(\theta_2)$, $(\theta_x)$, and $(\theta_y)$ created between the plurality of single cut guides 104 and the double cut guide 504, which may be any suitable angle. In various embodiments, the respective angles $(\theta_1)$, $(\theta_2)$, $(\theta_x)$, and $(\theta_y)$ may each be in the range of about 15° to about 75°.

Figure 13:
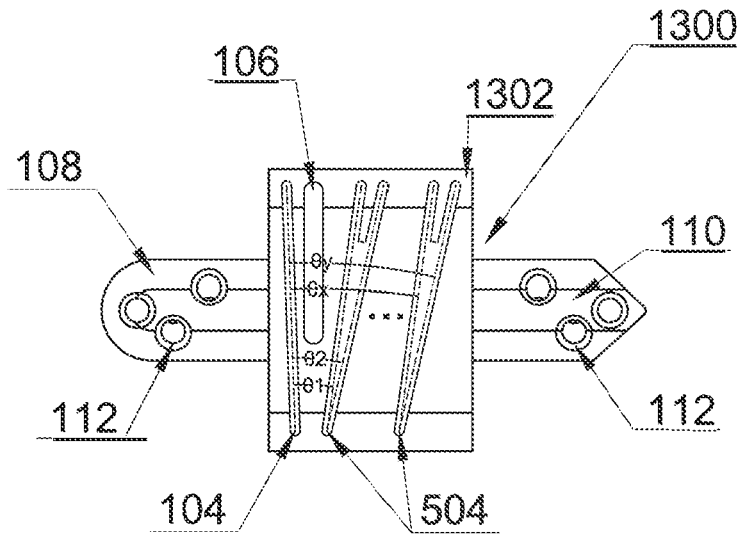
FIG. 13 is a diagram illustrating one embodiment of a surgical cutting block including a plurality of double cut guides and a single cut guide.

FIG. 13 is a diagram illustrating one embodiment of a surgical cutting block 1300 including a plurality of double cut guides 504 and a single cut guide 104. In this embodiment, the plurality of double cut guides 504 are positioned/located on a cutting platform 1302 on the side of the positioning slot 106 toward the metatarsal fixation platform 110. Further, surgical cutting block 1300 includes the single cut guide 104 positioned/located on the cutting platform 1302 on the side of the positioning slot 106 toward the cuneiform fixation platform 108.

In some embodiments, the plurality of double cut guides 504 and the single cut guide 104 are angled in the same direction (e.g., angled toward the left or toward the right with respect to the user (e.g., a medical professional)). In the illustrated embodiment, the plurality of double cut guides 504 and the single cut guide 104 are angled in different directions.

In additional or alternative embodiments, the plurality of double cut guides 504 and the single cut guide 104 are positioned on the cutting platform 1302 such that there is an angle $(\theta_1)$, $(\theta_2)$, $(\theta_x)$, and $(\theta_y)$ created between the single cut guide 104 and the plurality of double cut guides 504, which may be any suitable angle. In various embodiments, the respective angles $(\theta_1)$, $(\theta_2)$, $(\theta_x)$, and $(\theta_y)$ may each be in the range of about 15° to about 75°.

Figure 14:
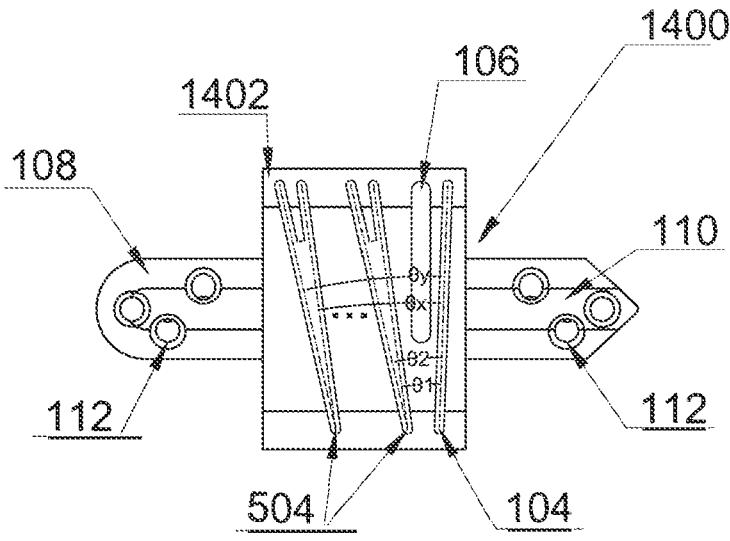
FIG. 14 is a diagram illustrating another embodiment of a surgical cutting block including a plurality of double cut guides and a single cut guide.

FIG. 14 is a diagram illustrating another embodiment of a surgical cutting block 1400 including a plurality of double cut guides 504 and a single cut guide 104. In this embodiment, the plurality of double cut guides 504 are positioned/located on a cutting platform 1402 on the side of the positioning slot 106 toward the cuneiform fixation platform 108. Further, surgical cutting block 1400 includes the single cut guide 104 positioned/located on the cutting platform 1402 on the side of the positioning slot 106 toward the metatarsal fixation platform 110.

In some embodiments, the plurality of double cut guides 504 and the single cut guide 104 are angled in the same direction (e.g., angled toward the left or toward the right with respect to the user (e.g., a medical professional)). In the illustrated embodiment, the plurality of double cut guides 504 and the single cut guide 104 are angled in different directions.

In additional or alternative embodiments, the plurality of double cut guides 504 and the single cut guide 104 are positioned on the cutting platform 1402 such that there is an angle $(\theta_1)$, $(\theta_2)$, $(\theta_x)$, and $(\theta_y)$ created between the single cut guide 104 and the plurality of double cut guides 504, which may be any suitable angle. In various embodiments, the respective angles $(\theta_1)$, $(\theta_2)$, $(\theta_x)$, and $(\theta_y)$ may each be in the range of about 15° to about 75°.

Figure 15:
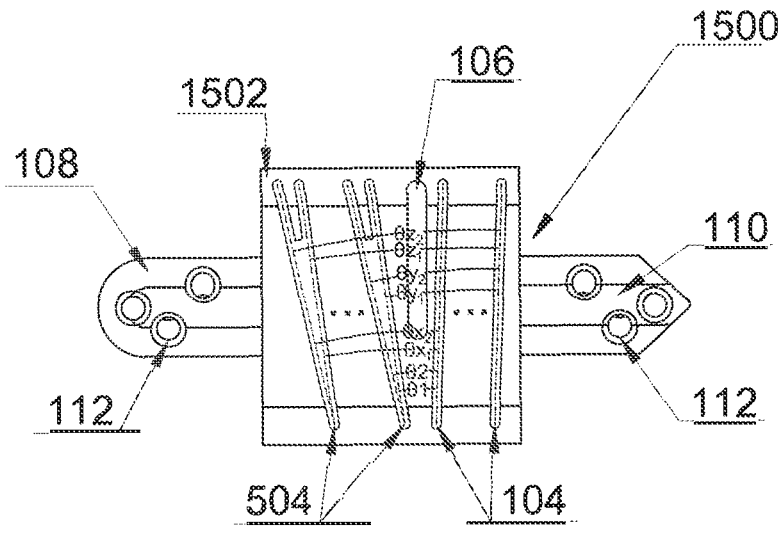
FIG. 15 is a diagram illustrating one embodiment of a surgical cutting block including a plurality of double cut guides and a plurality of single cut guides.

FIG. 15 is a diagram illustrating one embodiment of a surgical cutting block 1500 including a plurality of double cut guides 504 and a plurality of single cut guides 104. In this embodiment, the plurality of double cut guides 504 are located/positioned on a cutting platform 1502 toward the cuneiform fixation platform 108 and the plurality of single cut guides 104 are located/positioned on the cutting platform 1502 toward the metatarsal fixation platform 110.

In some embodiments, the plurality of double cut guides 504 and the plurality of single cut guides 104 are angled in the same direction (e.g., angled toward the left or toward the right with respect to the user (e.g., a medical professional)). In the illustrated embodiment, the plurality of double cut guides 504 and the plurality of single cut guides 104 are angled in different directions.

In additional or alternative embodiments, the plurality of double cut guides 504 and the plurality of single cut guides 104 are positioned on the cutting platform 1402 such that there is an angle $(\theta_1)$, $(\theta_2)$, $(\theta_{x1})$, $(\theta_{x2})$, $(\theta_{y1})$, $(\theta_{y2})$, $(\theta_{z1})$, and $(\theta_{z2})$ created between the plurality of single cut guides 104 and the plurality of double cut guides 504, which may be any suitable angle. In various embodiments, the respective angles $(\theta_1)$, $(\theta_2)$, $(\theta_{x1})$, $(\theta_{x2})$, $(\theta_{y1})$, $(\theta_{y2})$, $(\theta_{z1})$, and $(\theta_{z2})$ may each be in the range of about 15° to about 75°.

Figure 16:
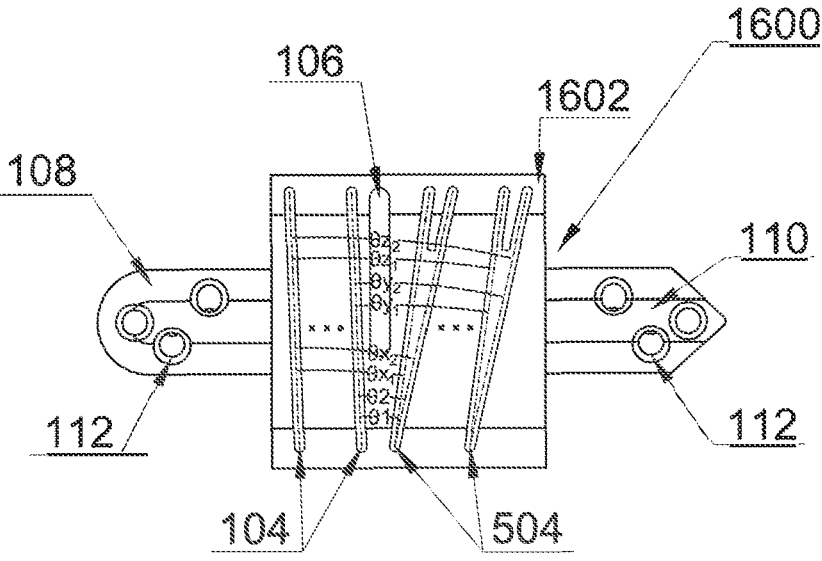
FIG. 16 is a diagram illustrating another embodiment of a surgical cutting block including a plurality of double cut guides and a plurality of single cut guides.

FIG. 16 is a diagram illustrating another embodiment of a surgical cutting block 1600 including a plurality of double cut guides 504 and a plurality of single cut guides 104. In this embodiment, the plurality of double cut guides 504 are located/positioned on a cutting platform 1602 toward the metatarsal fixation platform 110 and the plurality of single cut guides 104 are located/positioned on the cutting platform 1602 toward the cuneiform fixation platform 108.

In some embodiments, the plurality of double cut guides 504 and the plurality of single cut guides 104 are angled in the same direction (e.g., angled toward the left or toward the right with respect to the user (e.g., a medical professional)). In the illustrated embodiment, the plurality of double cut guides 504 and the plurality of single cut guides 104 are angled in different directions.

In additional or alternative embodiments, the plurality of double cut guides 504 and the plurality of single cut guides 104 are positioned on the cutting platform 1402 such that there is an angle $(\theta_1)$, $(\theta_2)$, $(\theta_{x1})$, $(\theta_{x2})$, $(\theta_{y1})$, $(\theta_{y2})$, $(\theta_{z1})$, and $(\theta_{z2})$ created between the plurality of single cut guides 104 and the plurality of double cut guides 504, which may be any suitable angle. In various embodiments, the respective angles $(\theta_1)$, $(\theta_2)$, $(\theta_{x1})$, $(\theta_{x2})$, $(\theta_{y1})$, $(\theta_{y2})$, $(\theta_{z1})$, and $(\theta_{x2})$ may each be in the range of about 15° to about 75°.

Figure 17:
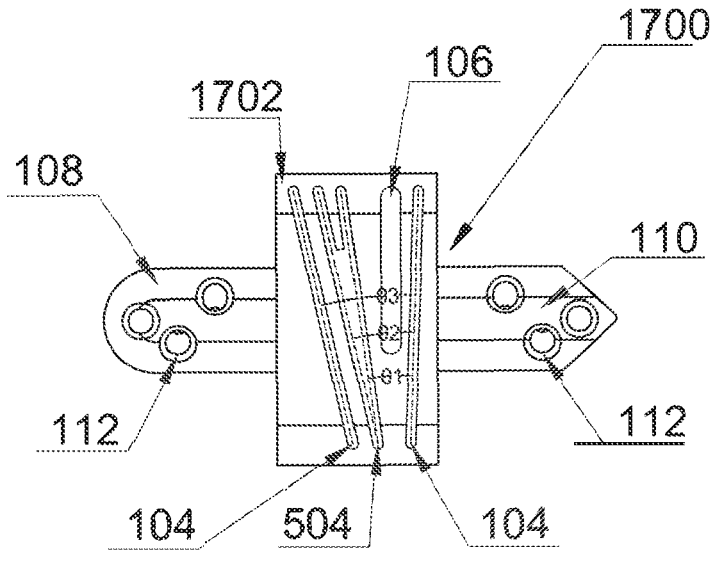
FIG. 17 is a diagram illustrating one embodiment of a surgical cutting block including a double cut guide and a plurality of single cut guides.

FIG. 17 is a diagram illustrating one embodiment of a surgical cutting block 1700 including a double cut guide 504 and a plurality of single cut guides 104. In this embodiment, the double cut guide 504 and one single cut guide 104 are located/positioned on a cutting platform 1702 toward the cuneiform fixation platform 108 and one single cut guide 104 is located/positioned on the cutting platform 1702 toward the metatarsal fixation platform 110. Further, the double cut guide 504 is located/positioned to the right of the single cut guide 104 on the cuneiform fixation platform 108 side of the cutting platform 102.

In some embodiments, the double cut guide 504 and the single cut guides 104 are angled in the same direction (e.g., angled toward the left or toward the right with respect to the user (e.g., a medical professional)). In the illustrated embodiment, the double cut guide 504 and the single cut guide 104 on the same side of the positioning slot 106 are angled in the same direction and the single cut guide 104 on the opposite side of the positioning slot 106 is angled in a different direction.

In additional or alternative embodiments, the double cut guide 504 and the single cut guide 104 are positioned on the cutting platform 1402 such that there is an angle $(\theta_1)$, $(\theta_2)$, and $(\theta_3)$ created between the double cut guide 504 and the single cut guide 104 and the other single cut guide 104, which may be any suitable angle. In various embodiments, the respective angles $(\theta_1)$, $(\theta_2)$, and $(\theta_3)$ may each be in the range of about 15° to about 75°.

Figure 18:
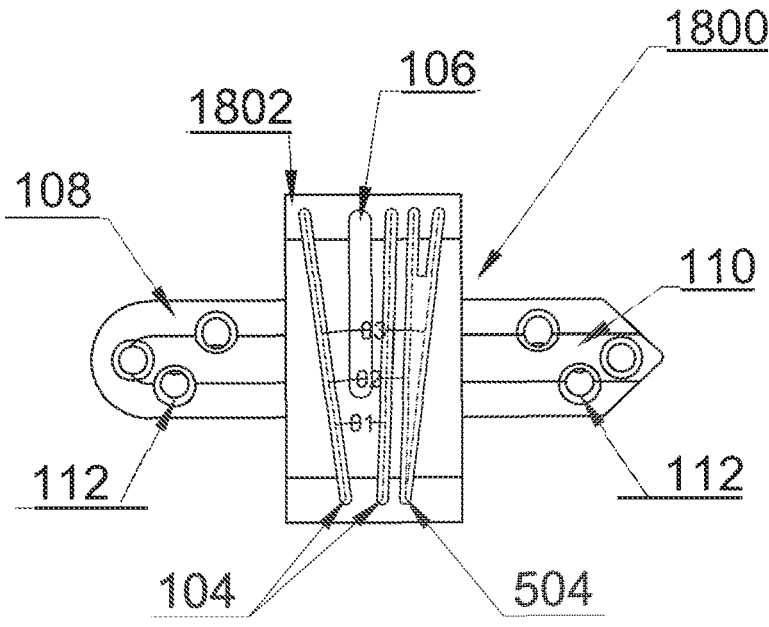
FIG. 18 is a diagram illustrating another embodiment of a surgical cutting block including a double cut guide and a plurality of single cut guides.

FIG. 18 is a diagram illustrating another embodiment of a surgical cutting block 1800 including a double cut guide 504 and a plurality of single cut guides 104. In this embodiment, the double cut guide 504 and one single cut guide 104 are located/positioned on a cutting platform 1802 toward the metatarsal fixation platform 110 and one single cut guide 104 is located/positioned on the cutting platform 1802 toward the cuneiform fixation platform 108. Further, the double cut guide 504 is located/positioned to the right of the single cut guide 104 on the metatarsal fixation platform 110 side of the cutting platform 1802.

In some embodiments, the double cut guide 504 and the single cut guides 104 are angled in the same direction (e.g., angled toward the left or toward the right with respect to the user (e.g., a medical professional)). In the illustrated embodiment, the double cut guide 504 and the single cut guide 104 on the same side of the positioning slot 106 are angled in the same direction and the single cut guide 104 on the opposite side of the positioning slot 106 is angled in a different direction.

In additional or alternative embodiments, the double cut guide 504 and the single cut guide 104 are positioned on the cutting platform 1402 such that there is an angle $(\theta_1)$, $(\theta_2)$, and $(\theta_3)$ created between the double cut guide 504 and the single cut guide 104 and the other single cut guide 104, which may be any suitable angle. In various embodiments, the respective angles $(\theta_1)$, $(\theta_2)$, and $(\theta_3)$ may each be in the range of about 15° to about 75°.

Figure 19:
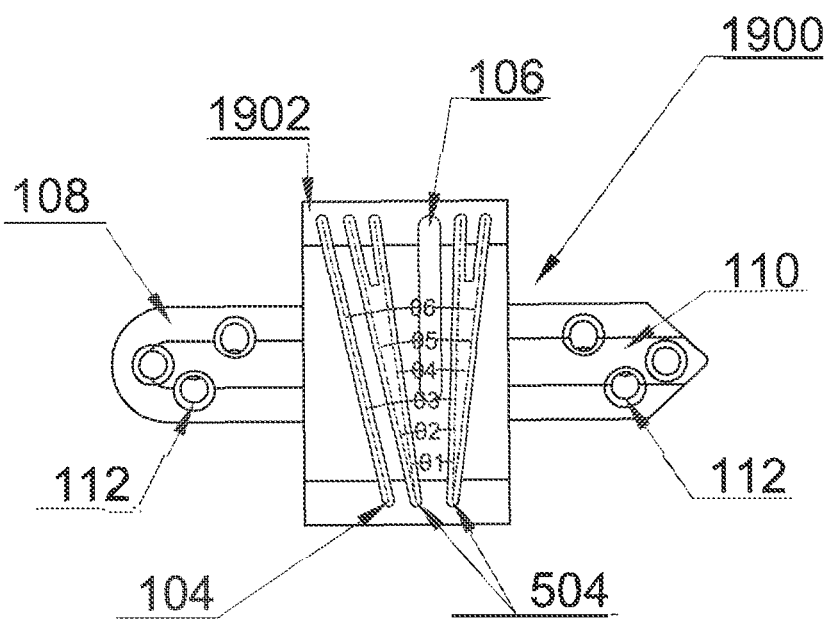
FIG. 19 is a diagram illustrating one embodiment of a surgical cutting block including a plurality of double cut guides and a single cut guide.

FIG. 19 is a diagram illustrating one embodiment of a surgical cutting block 1900 including a plurality of double cut guides 504 and a single cut guide 104. In this embodiment, one double cut guide 504 and the single cut guide 104 are located/positioned on a cutting platform 1902 toward the cuneiform fixation platform 108 and one double cut guide 504 is located/positioned on the cutting platform 1902 toward the metatarsal fixation platform 110. Further, the double cut guide 504 is located/positioned to the right of the single cut guide 104 on the cuneiform fixation platform 108 side of the cutting platform 1902.

In some embodiments, the double cut guides 504 and the single cut guide 104 are angled in the same direction (e.g., angled toward the left or toward the right with respect to the user (e.g., a medical professional)). In the illustrated embodiment, the double cut guide 504 and the single cut guide 104 on the same side of the positioning slot 106 are angled in the same direction and the double cut guide 504 on the opposite side of the positioning slot 106 is angled in a different direction.

In additional or alternative embodiments, the double cut guide 504 and the single cut guide 104 are positioned on the cutting platform 1402 such that there is an angle $(\theta_1)$, $(\theta_2)$, $(\theta_3)$, $(\theta_4)$, $(\theta_5)$, and $(\theta_6)$ created between the double cut guide 504 and the single cut guide 104 and the other double cut guide 504, which may be any suitable angle. In various embodiments, the respective angles $(\theta_1)$, $(\theta_2)$, $(\theta_3)$, $(\theta_4)$, $(\theta_5)$, and $(\theta_6)$ may each be in the range of about 15° to about 75°.

Figure 20:
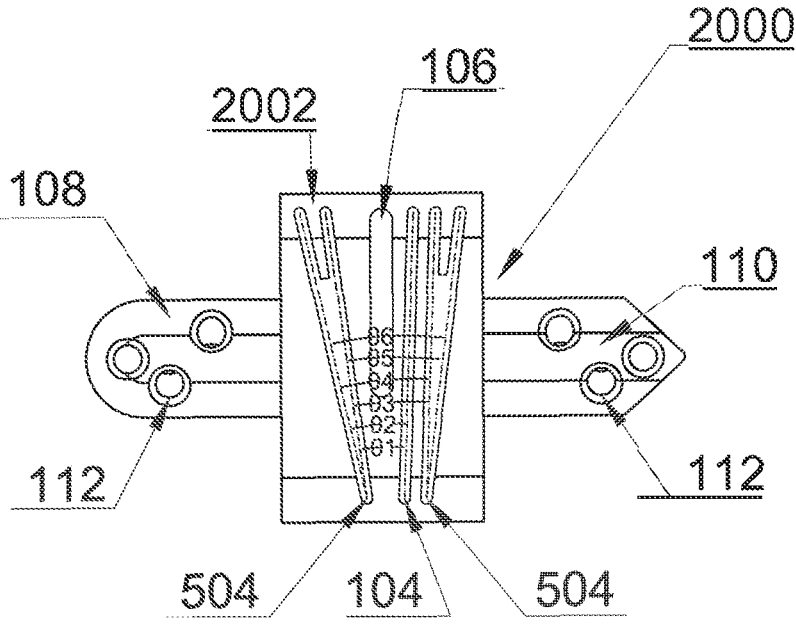
FIG. 20 is a diagram illustrating another embodiment of a surgical cutting block including a plurality of double cut guides and a single cut guide.

FIG. 20 is a diagram illustrating another embodiment of a surgical cutting block 2000 including a plurality of double cut guides 504 and a single cut guide 104. In this embodiment, one double cut guide 504 and the single cut guide 104 are located/positioned on a cutting platform 2002 toward the metatarsal fixation platform 110 and one double cut guide 504 is located/positioned on the cutting platform 2002 toward the cuneiform fixation platform 108. Further, the double cut guide 504 is located/positioned to the right of the single cut guide 104 on the metatarsal fixation platform 110 side of the cutting platform 2002.

In some embodiments, the double cut guides 504 and the single cut guide 104 are angled in the same direction (e.g., angled toward the left or toward the right with respect to the user (e.g., a medical professional)). In the illustrated embodiment, the double cut guide 504 and the single cut guide 104 on the same side of the positioning slot 106 are angled in the same direction and the double cut guide 504 on the opposite side of the positioning slot 106 is angled in a different direction.

In additional or alternative embodiments, the double cut guide 504 and the single cut guide 104 are positioned on the cutting platform 1402 such that there is an angle $(\theta_1)$, $(\theta_2)$, $(\theta_3)$, $(\theta_4)$, $(\theta_5)$, and $(\theta_6)$ created between the double cut guide 504 and the single cut guide 104 and the other double cut guide 504, which may be any suitable angle. In various embodiments, the respective angles $(\theta_1)$, $(\theta_2)$, $(\theta_3)$, $(\theta_4)$, $(\theta_5)$, and $(\theta_6)$ may each be in the range of about 15° to about 75°.

Figure 21:
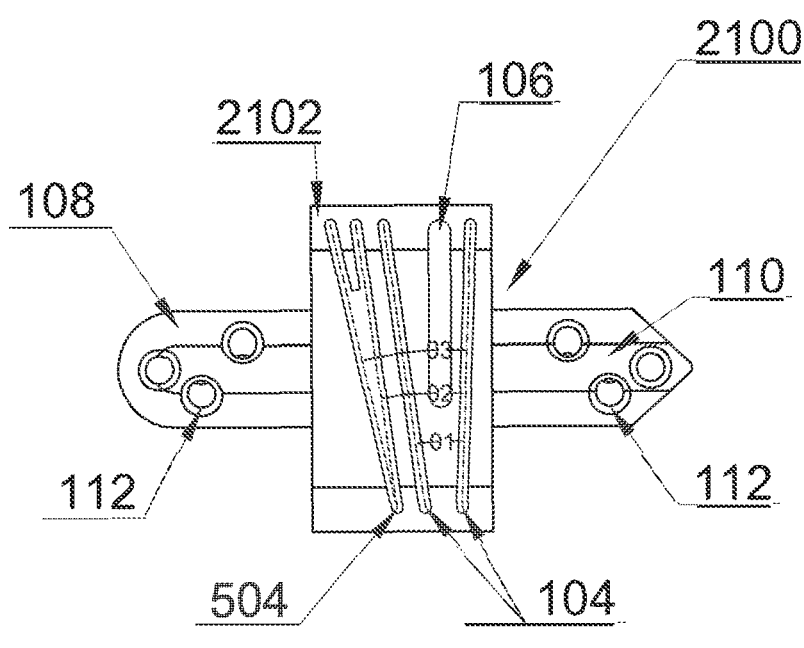
FIG. 21 is a diagram illustrating one embodiment of a surgical cutting block including a double cut guide and a plurality of single cut guides.

FIG. 21 is a diagram illustrating one embodiment of a surgical cutting block 2100 including a double cut guide 504 and a plurality of single cut guides 104. In this embodiment, the double cut guide 504 and one single cut guide 104 are located/positioned on a cutting platform 2102 toward the cuneiform fixation platform 108 and one single cut guide 104 is located/positioned on the cutting platform 2102 toward the metatarsal fixation platform 110. Further, the double cut guide 504 is located/positioned to the left of the single cut guide 104 on the cuneiform fixation platform 108 side of the cutting platform 2102.

In some embodiments, the double cut guide 504 and the single cut guides 104 are angled in the same direction (e.g., angled toward the left or toward the right with respect to the user (e.g., a medical professional)). In the illustrated embodiment, the double cut guide 504 and the single cut guide 104 on the same side of the positioning slot 106 are angled in the same direction and the single cut guide 104 on the opposite side of the positioning slot 106 is angled in a different direction.

In additional or alternative embodiments, the double cut guide 504 and the single cut guide 104 are positioned on the cutting platform 1402 such that there is an angle $(\theta_1)$, $(\theta_2)$, and $(\theta_3)$ created between the double cut guide 504 and the single cut guide 104 and the other single cut guide 104, which may be any suitable angle. In various embodiments, the respective angles $(\theta_1)$, $(\theta_2)$, and $(\theta_3)$ may each be in the range of about 15° to about 75°.

Figure 22:
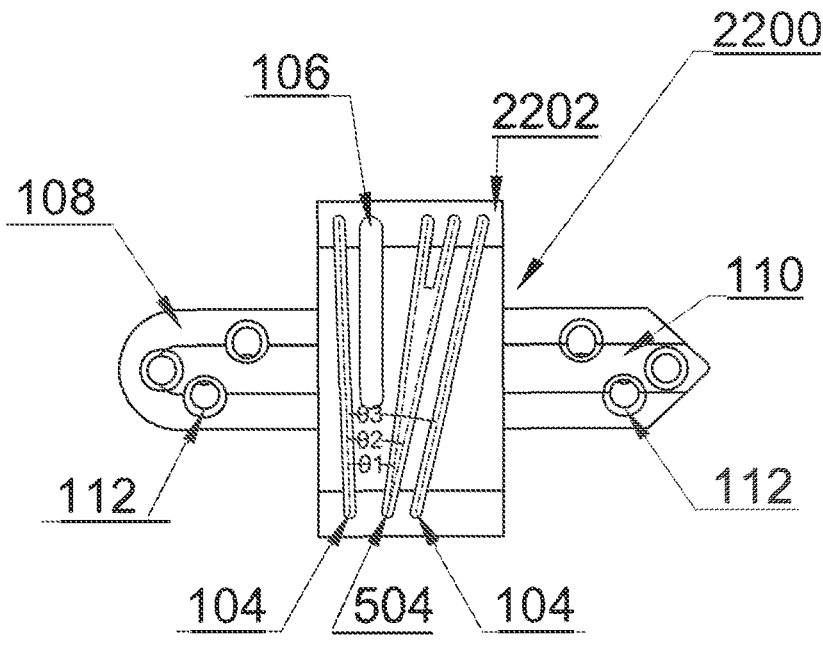
FIG. 22 is a diagram illustrating another embodiment of a surgical cutting block including a double cut guide and a plurality of single cut guides.

FIG. 22 is a diagram illustrating another embodiment of a surgical cutting block 2200 including a double cut guide 504 and a plurality of single cut guides 104. In this embodiment, the double cut guide 504 and one single cut guide 104 are located/positioned on a cutting platform 2202 toward the metatarsal fixation platform 110 and one single cut guide 104 is located/positioned on the cutting platform 2202 toward the cuneiform fixation platform 108. Further, the double cut guide 504 is located/positioned to the left of the single cut guide 104 on the metatarsal fixation platform 110 side of the cutting platform 2202.

In some embodiments, the double cut guide 504 and the single cut guides 104 are angled in the same direction (e.g., angled toward the left or toward the right with respect to the user (e.g., a medical professional)). In the illustrated embodiment, the double cut guide 504 and the single cut guide 104 on the same side of the positioning slot 106 are angled in the same direction and the single cut guide 104 on the opposite side of the positioning slot 106 is angled in a different direction.

In additional or alternative embodiments, the double cut guide 504 and the single cut guide 104 are positioned on the cutting platform 1402 such that there is an angle $(\theta_1)$, $(\theta_2)$, and $(\theta_3)$ created between the double cut guide 504 and the single cut guide 104 and the other single cut guide 104, which may be any suitable angle. In various embodiments, the respective angles $(\theta_1)$, $(\theta_2)$, and $(\theta_3)$ may each be in the range of about 15° to about 75°.

Figure 23:
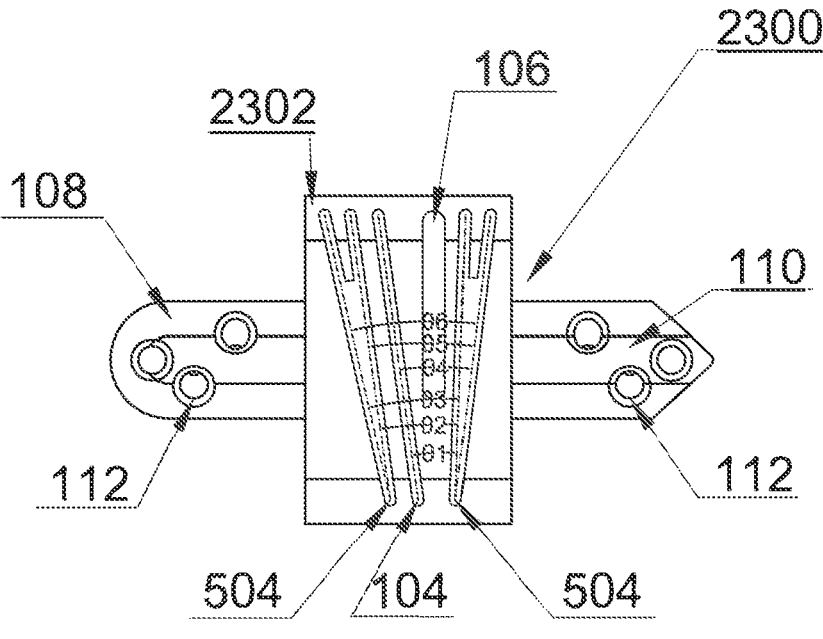
FIG. 23 is a diagram illustrating an embodiment of a surgical cutting block including a plurality of double cut guides and a single cut guide.

FIG. 23 is a diagram illustrating one embodiment of a surgical cutting block 2300 including a plurality of double cut guides 504 and a single cut guide 104. In this embodiment, one double cut guide 504 and the single cut guide 104 are located/positioned on a cutting platform 2302 toward the cuneiform fixation platform 108 and one double cut guide 504 is located/positioned on the cutting platform 2302 toward the metatarsal fixation platform 110. Further, the double cut guide 504 is located/positioned to the left of the single cut guide 104 on the cuneiform fixation platform 108 side of the cutting platform 2302.

In some embodiments, the double cut guides 504 and the single cut guide 104 are angled in the same direction (e.g., angled toward the left or toward the right with respect to the user (e.g., a medical professional)). In the illustrated embodiment, the double cut guide 504 and the single cut guide 104 on the same side of the positioning slot 106 are angled in the same direction and the double cut guide 504 on the opposite side of the positioning slot 106 is angled in a different direction.

In additional or alternative embodiments, the double cut guide 504 and the single cut guide 104 are positioned on the cutting platform 1402 such that there is an angle $(\theta_1)$, $(\theta_2)$, $(\theta_3)$, $(\theta_4)$, $(\theta_5)$, and $(\theta_6)$ created between the double cut guide 504 and the single cut guide 104 and the other double cut guide 504, which may be any suitable angle. In various embodiments, the respective angles $(\theta_1)$, $(\theta_2)$, $(\theta_3)$, $(\theta_4)$, $(\theta_5)$, and $(\theta_6)$ may each be in the range of about 15° to about 75°.

Figure 24:
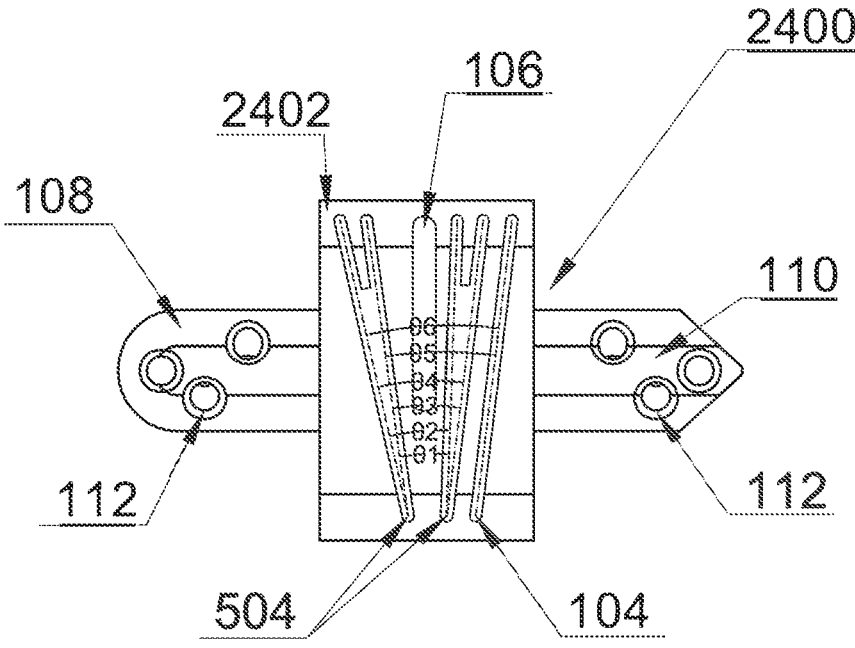
FIG. 24 is a diagram illustrating another embodiment of a surgical cutting block including a plurality of double cut guides and a single cut guide.

FIG. 24 is a diagram illustrating another embodiment of a surgical cutting block 2400 including a plurality of double cut guides 504 and a single cut guide 104. In this embodiment, one double cut guide 504 and the single cut guide 104 are located/positioned on a cutting platform 2402 toward the metatarsal fixation platform 110 and one double cut guide 504 is located/positioned on the cutting platform 2402 toward the cuneiform fixation platform 108. Further, the double cut guide 504 is located/positioned to the left of the single cut guide 104 on the metatarsal fixation platform 110 side of the cutting platform 2402.

In some embodiments, the double cut guides 504 and the single cut guide 104 are angled in the same direction (e.g., angled toward the left or toward the right with respect to the user (e.g., a medical professional)). In the illustrated embodiment, the double cut guide 504 and the single cut guide 104 on the same side of the positioning slot 106 are angled in the same direction and the double cut guide 504 on the opposite side of the positioning slot 106 is angled in a different direction.

In additional or alternative embodiments, the double cut guide 504 and the single cut guide 104 are positioned on the cutting platform 1402 such that there is an angle $(\theta_1)$, $(\theta_2)$, $(\theta_3)$, $(\theta_4)$, $(\theta_5)$, and $(\theta_6)$ created between the double cut guide 504 and the single cut guide 104 and the other double cut guide 504, which may be any suitable angle. In various embodiments, the respective angles $(\theta_1)$, $(\theta_2)$, $(\theta_3)$, $(\theta_4)$, $(\theta_5)$, and $(\theta_6)$ may each be in the range of about 15° to about 75°.

Figure 25:
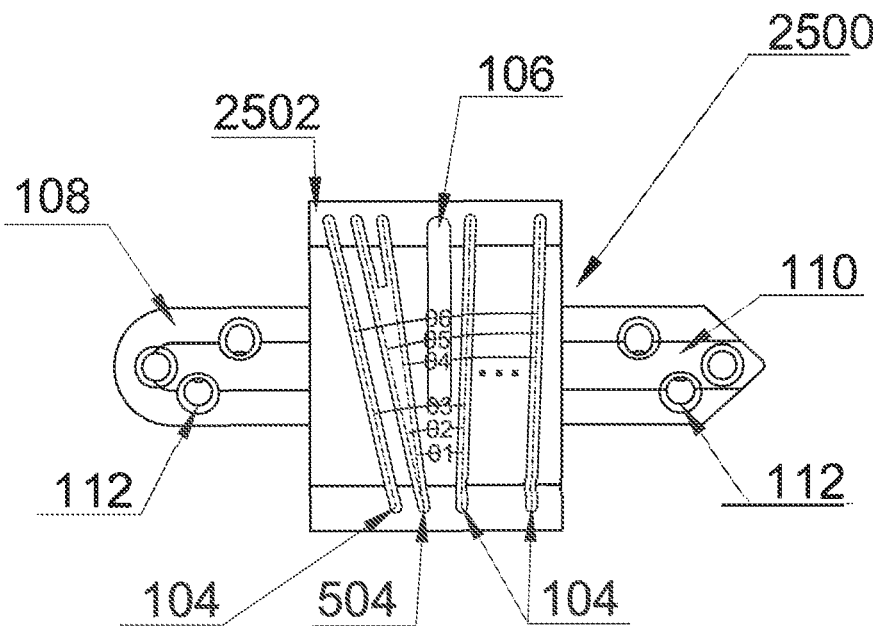
FIG. 25 is a diagram illustrating another embodiment of a surgical cutting block including a double cut guide and a plurality of single cut guides.

FIG. 25 is a diagram illustrating another embodiment of a surgical cutting block 2500 including a double cut guide 504 and a plurality of single cut guides 104. In this embodiment, the double cut guide 504 and one single cut guide 104 are located/positioned on a cutting platform 2502 toward the cuneiform fixation platform 108 and a plurality of single cut guides 104 are located/positioned on the cutting platform 2502 toward the metatarsal fixation platform 110. Further, the double cut guide 504 is located/positioned to the right of the single cut guide 104 on the cuneiform fixation platform 108 side of the cutting platform 2502.

In some embodiments, the double cut guide 504 and the single cut guides 104 are angled in the same direction (e.g., angled toward the left or toward the right with respect to the user (e.g., a medical professional)). In the illustrated embodiment, the double cut guide 504 and the single cut guide 104 on the same side of the positioning slot 106 are angled in the same direction and the plurality of single cut guides 104 on the opposite side of the positioning slot 106 are angled in the direction as one another and a different direction than the double cut guide 504 and the single cut guide 104.

In additional or alternative embodiments, the double cut guide 504 and the single cut guide 104 are positioned on the cutting platform 1402 such that there is an angle $(\theta_1)$, $(\theta_2)$, $(\theta_3)$, $(\theta_4)$, $(\theta_5)$, and $(\theta_6)$ created between the double cut guide 504 and the single cut guide 104 and the other plurality of single cut guides 104, which may be any suitable angle. In various embodiments, the respective angles $(\theta_1)$, $(\theta_2)$, $(\theta_3)$, $(\theta_4)$, $(\theta_5)$, and $(\theta_6)$ may each be in the range of about 15° to about 75°.

Figure 26:
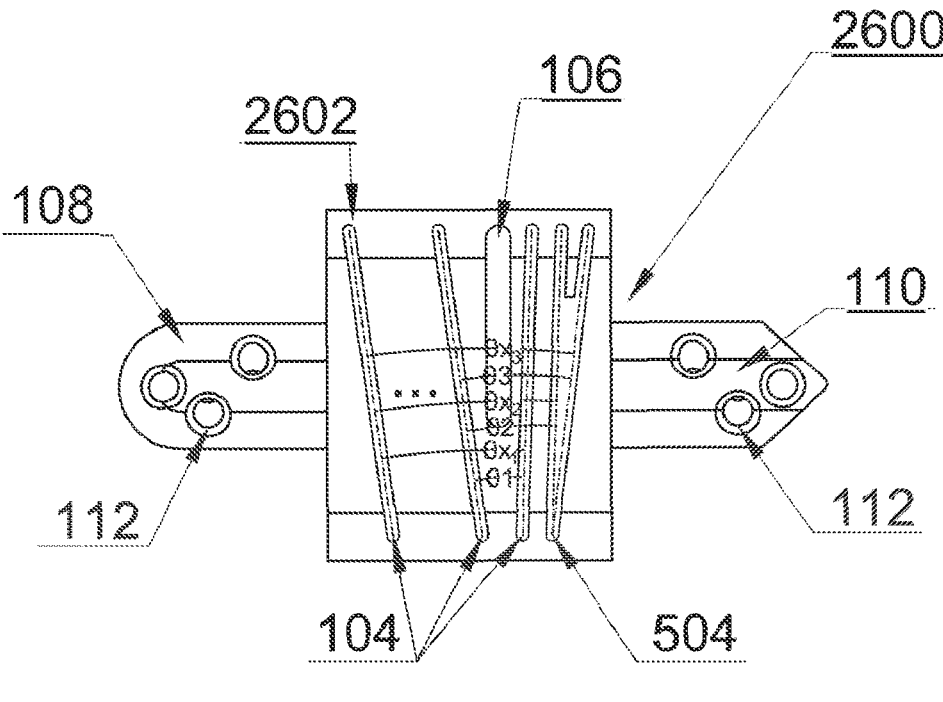
FIG. 26 is a diagram illustrating still another embodiment of a surgical cutting block including a double cut guide and a plurality of single cut guides.

FIG. 26 is a diagram illustrating another embodiment of a surgical cutting block 2600 including a double cut guide 504 and a plurality of single cut guides 104. In this embodiment, the double cut guide 504 and one single cut guide 104 are located/positioned on a cutting platform 2602 toward the metatarsal fixation platform 110 and a plurality of single cut guides 104 are located/positioned on the cutting platform 2602 toward the cuneiform fixation platform 108. Further, the double cut guide 504 is located/positioned to the right of the single cut guide 104 on the metatarsal fixation platform 110 side of the cutting platform 2602.

In some embodiments, the double cut guide 504 and the single cut guides 104 are angled in the same direction (e.g., angled toward the left or toward the right with respect to the user (e.g., a medical professional)). In the illustrated embodiment, the double cut guide 504 and the single cut guide 104 on the same side of the positioning slot 106 are angled in the same direction, the plurality of single cut guides 104 on the opposite side of the positioning slot 106 are angled in the direction as one another and a different direction than the double cut guide 504 and the single cut guide 104.

In additional or alternative embodiments, the double cut guide 504 and the single cut guide 104 are positioned on the cutting platform 1402 such that there is an angle ($\theta_1$), ($\theta_2$), ($\theta_3$), ($\theta_{x1}$), ($\theta_{x2}$), and ($\theta_{x3}$) created between the double cut guide 504 and the single cut guide 104 and the other plurality of single cut guides 104, which may be any suitable angle. In various embodiments, the respective angles ($\theta_1$), ($\theta_2$), ($\theta_3$), ($\theta_{x1}$), ($\theta_{x2}$), and ($\theta_{x3}$) may each be in the range of about 15° to about 75°.

Figure 27:
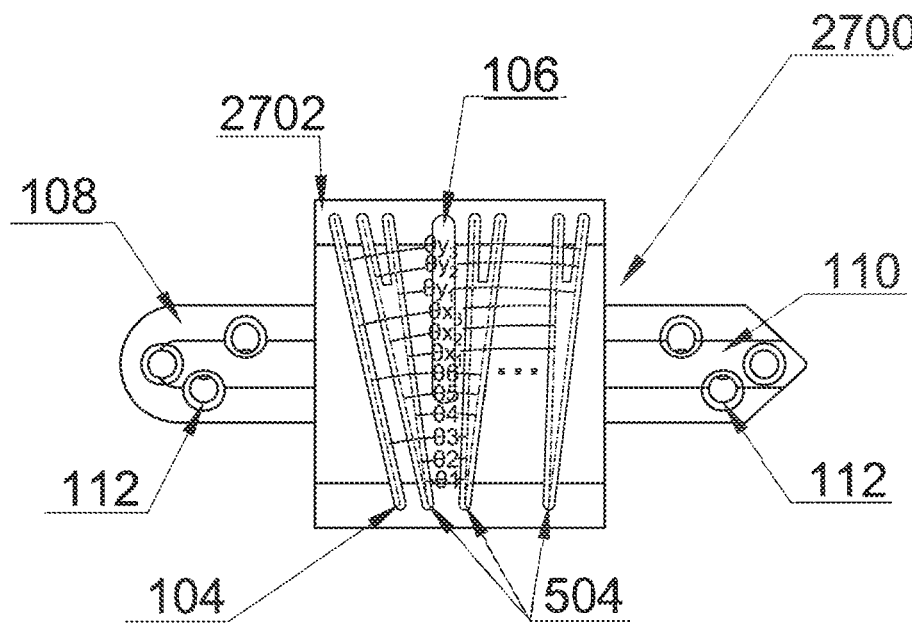
FIG. 27 is a diagram illustrating another embodiment of a surgical cutting block including a plurality of double cut guides and a single cut guide.

FIG. 27 is a diagram illustrating one embodiment of a surgical cutting block 2700 including a plurality of double cut guides 504 and a single cut guide 104. In this embodiment, one double cut guide 504 and the single cut guide 104 are located/positioned on a cutting platform 2702 toward the cuneiform fixation platform 108 and a plurality of double cut guides 504 are located/positioned on the cutting platform 2702 toward the metatarsal fixation platform 110. Further, the double cut guide 504 is located/positioned to the right of the single cut guide 104 on the cuneiform fixation platform 108 side of the cutting platform 2702.

In some embodiments, the double cut guides 504 and the single cut guide 104 are angled in the same direction (e.g., angled toward the left or toward the right with respect to the user (e.g., a medical professional)). In the illustrated embodiment, the double cut guide 504 and the single cut guide 104 on the same side of the positioning slot 106 are angled in the same direction and the plurality of double cut guides 504 on the opposite side of the positioning slot 106 are angled in a different direction.

In additional or alternative embodiments, the double cut guide 504 and the single cut guide 104 are positioned on the cutting platform 1402 such that there is an angle ($\theta_1$), ($\theta_2$), ($\theta_3$), ($\theta_4$), ($\theta_5$), ($\theta_6$), ($\theta_{x1}$), ($\theta_{x2}$), ($\theta_{x3}$), ($\theta_{y1}$), ($\theta_{y2}$), and ($\theta_{y3}$) created between the double cut guide 504 and the single cut guide 104 and the plurality of double cut guides 504, which may be any suitable angle. In various embodiments, the respective angles ($\theta_1$), ($\theta_2$), ($\theta_3$), ($\theta_4$), ($\theta_5$), ($\theta_6$), ($\theta_{x1}$), ($\theta_{x2}$), ($\theta_{x3}$), ($\theta_{y1}$), ($\theta_{y2}$), and ($\theta_{y3}$) may each be in the range of about 15° to about 75°.

Figure 28:
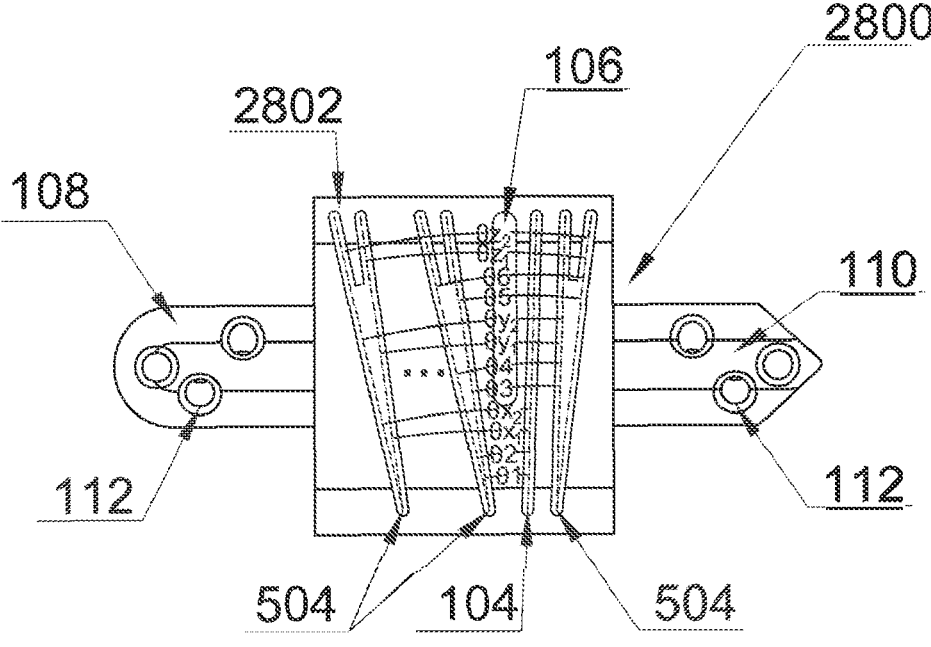
FIG. 28 is a diagram illustrating still another embodiment of a surgical cutting block including a plurality of double cut guides and a single cut guide.

FIG. 28 is a diagram illustrating another embodiment of a surgical cutting block 2800 including a plurality of double cut guides 504 and a single cut guide 104. In this embodiment, one double cut guide 504 and the single cut guide 104 are located/positioned on a cutting platform 2802 toward the metatarsal fixation platform 110 and a plurality of double cut guides 504 are located/positioned on the cutting platform 2802 toward the cuneiform fixation platform 108. Further, the double cut guide 504 is located/positioned to the right of the single cut guide 104 on the metatarsal fixation platform 110 side of the cutting platform 2802.

In some embodiments, the double cut guides 504 and the single cut guide 104 are angled in the same direction (e.g., angled toward the left or toward the right with respect to the user (e.g., a medical professional)). In the illustrated embodiment, the double cut guide 504 and the single cut guide 104 on the same side of the positioning slot 106 are angled in the same direction and the plurality of double cut guides 504 on the opposite side of the positioning slot 106 are angled in a different direction.

In additional or alternative embodiments, the double cut guide 504 and the single cut guide 104 are positioned on the cutting platform 1402 such that there is an angle ($\theta_1$), ($\theta_2$), ($\theta_3$), ($\theta_4$), ($\theta_5$), ($\theta_6$), ($\theta_{x1}$), ($\theta_{x2}$), ($\theta_{y1}$), ($\theta_{y2}$), ($\theta_{z1}$), and ($\theta_{z2}$) created between the double cut guide 504 and the single cut guide 104 and the plurality of double cut guides 504, which may be any suitable angle. In various embodiments, the respective angles ($\theta_1$), ($\theta_2$), ($\theta_3$), ($\theta_4$), ($\theta_5$), ($\theta_6$), ($\theta_{x1}$), ($\theta_{x2}$), ($\theta_{y1}$), ($\theta_{y1}$), ($\theta_{z1}$), and ($\theta_{z2}$) may each be in the range of about 15° to about 75°.

Figure 29:
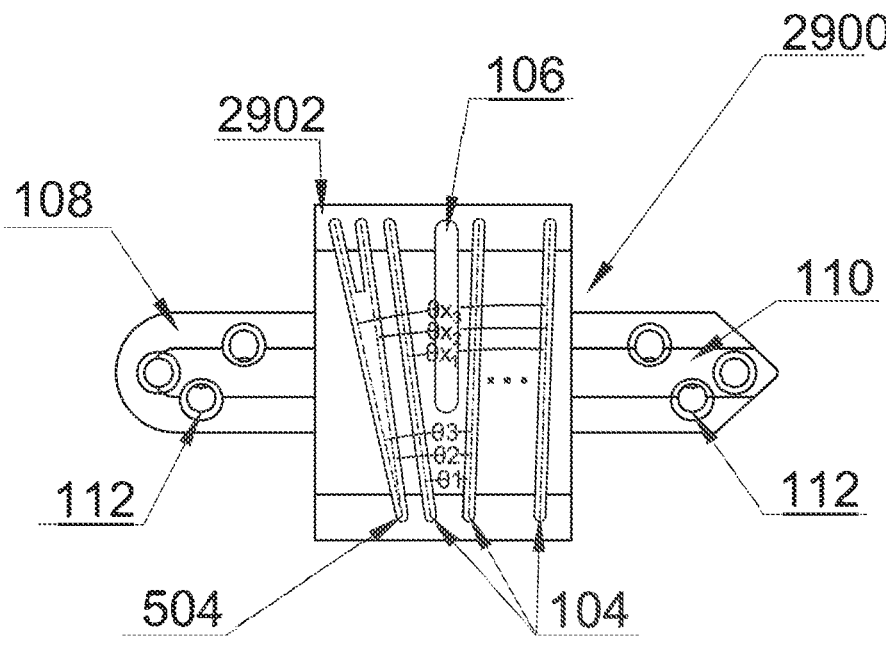
FIG. 29 is a diagram illustrating another embodiment of a surgical cutting block including a double cut guide and a plurality of single cut guides.

FIG. 29 is a diagram illustrating another embodiment of a surgical cutting block 2900 including a double cut guide 504 and a plurality of single cut guides 104. In this embodiment, the double cut guide 504 and one single cut guide 104 are located/positioned on a cutting platform 2902 toward the cuneiform fixation platform 108 and a plurality of single cut guides 104 are located/positioned on the cutting platform 2902 toward the metatarsal fixation platform 110. Further, the double cut guide 504 is located/positioned to the left of the single cut guide 104 on the cuneiform fixation platform 108 side of the cutting platform 2902.

In some embodiments, the double cut guide 504 and the single cut guides 104 are angled in the same direction (e.g., angled toward the left or toward the right with respect to the user (e.g., a medical professional)). In the illustrated embodiment, the double cut guide 504 and the single cut guide 104 on the same side of the positioning slot 106 are angled in the same direction, the plurality of single cut guides 104 on the opposite side of the positioning slot 106 are angled in the direction as one another and a different direction than the double cut guide 504 and the single cut guide 104.

In additional or alternative embodiments, the double cut guide 504 and the single cut guide 104 are positioned on the cutting platform 1402 such that there is an angle ($\theta_1$), ($\theta_2$), ($\theta_3$), ($\theta_{x1}$), ($\theta_{x2}$), and ($\theta_{x3}$) created between the double cut guide 504 and the single cut guide 104 and the other plurality of single cut guides 104, which may be any suitable angle. In various embodiments, the respective angles ($\theta_1$), ($\theta_2$), ($\theta_3$), ($\theta_{x1}$), ($\theta_{x2}$), and ($\theta_{x3}$) may each be in the range of about 15° to about 75°.

Figure 30:
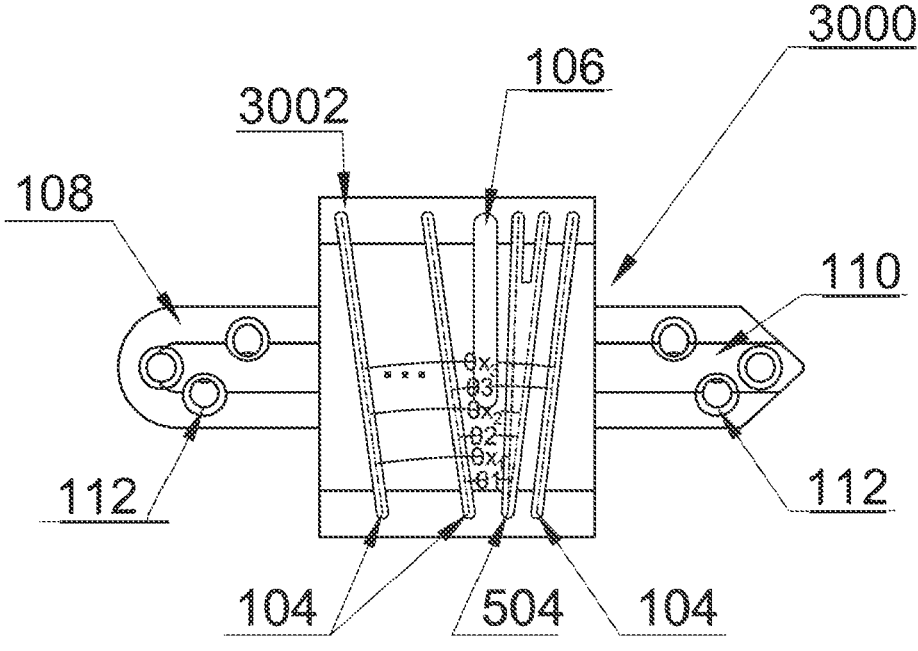
FIG. 30 is a diagram illustrating still another embodiment of a surgical cutting block including a double cut guide and a plurality of single cut guides.

FIG. 30 is a diagram illustrating another embodiment of a surgical cutting block 3000 including a double cut guide 504 and a plurality of single cut guides 104. In this embodiment, the double cut guide 504 and one single cut guide 104 are located/positioned on a cutting platform 3002 toward the metatarsal fixation platform 110 and a plurality of single cut guides 104 are located/positioned on the cutting platform 3002 toward the cuneiform fixation platform 108. Further, the double cut guide 504 is located/positioned to the left of the single cut guide 104 on the metatarsal fixation platform 110 side of the cutting platform 3002.

In some embodiments, the double cut guide 504 and the single cut guides 104 are angled in the same direction (e.g., angled toward the left or toward the right with respect to the user (e.g., a medical professional)). In the illustrated embodiment, the double cut guide 504 and the single cut guide 104 on the same side of the positioning slot 106 are angled in the same direction, the plurality of single cut guides 104 on the opposite side of the positioning slot 106 are angled in the direction as one another and a different direction than the double cut guide 504 and the single cut guide 104.

In additional or alternative embodiments, the double cut guide 504 and the single cut guide 104 are positioned on the cutting platform 1402 such that there is an angle ($\theta_1$), ($\theta_2$), ($\theta_3$), ($\theta_{x1}$), ($\theta_{x2}$), and ($\theta_{x3}$) created between the double cut guide 504 and the single cut guide 104 and the other plurality of single cut guides 104, which may be any suitable angle. In various embodiments, the respective angles ($\theta_1$), ($\theta_2$), ($\theta_3$), ($\theta_{x1}$), ($\theta_{x2}$), and ($\theta_{x3}$) may each be in the range of about 15° to about 75°.

Figure 31:
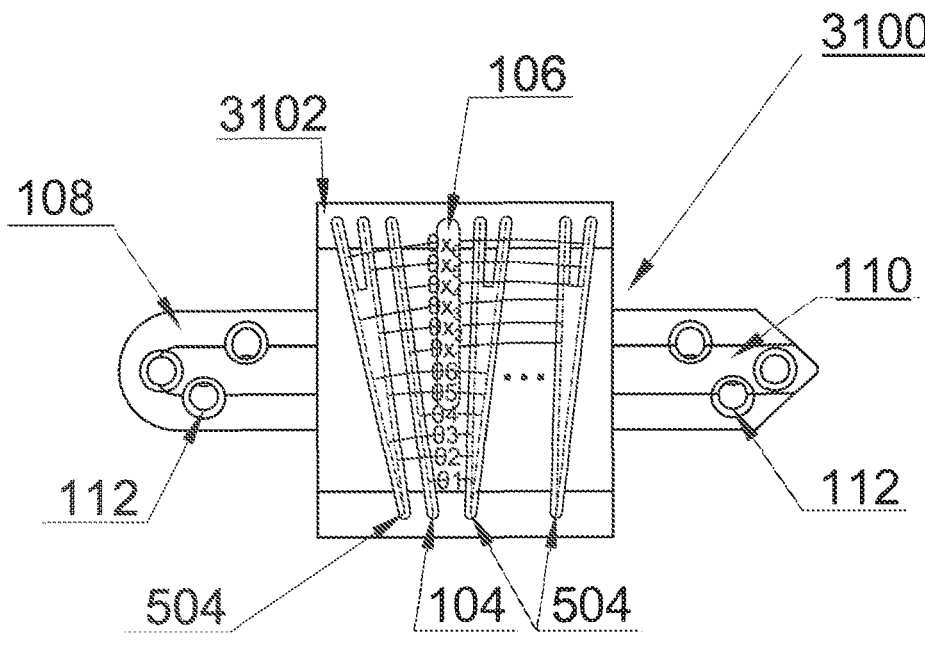
FIG. 31 is a diagram illustrating another embodiment of a surgical cutting block including a plurality of double cut guides and a single cut guide.

FIG. 31 is a diagram illustrating one embodiment of a surgical cutting block 3100 including a plurality of double cut guides 504 and a single cut guide 104. In this embodiment, one double cut guide 504 and the single cut guide 104 are located/positioned on a cutting platform 3102 toward the cuneiform fixation platform 108 and a plurality of double cut guides 504 are located/positioned on the cutting platform 3102 toward the metatarsal fixation platform 110. Further, the double cut guide 504 is located/positioned to the left of the single cut guide 104 on the cuneiform fixation platform 108 side of the cutting platform 3102.

In some embodiments, the double cut guides 504 and the single cut guide 104 are angled in the same direction (e.g., angled toward the left or toward the right with respect to the user (e.g., a medical professional)). In the illustrated embodiment, the double cut guide 504 and the single cut guide 104 on the same side of the positioning slot 106 are angled in the same direction and the plurality of double cut guides 504 on the opposite side of the positioning slot 106 are angled in a different direction.

In additional or alternative embodiments, the double cut guide 504 and the single cut guide 104 are positioned on the cutting platform 1402 such that there is an angle $(\theta_1)$, $(\theta_2)$, $(\theta_3)$, $(\theta_4)$, $(\theta_5)$, $(\theta_6)$, $(\theta_{x1})$, $(\theta_{x2})$, $(\theta_{x3})$, $(\theta_{x4})$, $(\theta_{x5})$, and $(\theta_{x6})$ created between the double cut guide 504 and the single cut guide 104 and the plurality of double cut guides 504, which may be any suitable angle. In various embodiments, the respective angles $(\theta_1)$, $(\theta_2)$, $(\theta_3)$, $(\theta_4)$, $(\theta_5)$, $(\theta_6)$, $(\theta_{x1})$, $(\theta_{x2})$, $(\theta_{x3})$, $(\theta_{x4})$, $(\theta_{x5})$, and $(\theta_{x6})$ may each be in the range of about 15° to about 75°.

Figure 32:
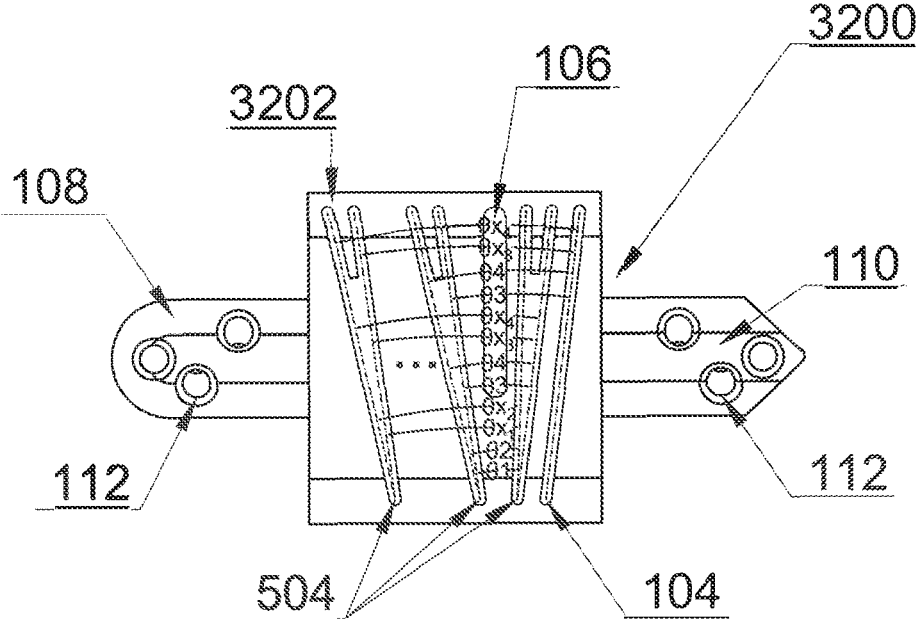
FIG. 32 is a diagram illustrating still another embodiment of a surgical cutting block including a plurality of double cut guides and a single cut guide.

FIG. 32 is a diagram illustrating another embodiment of a surgical cutting block 3200 including a plurality of double cut guides 504 and a single cut guide 104. In this embodiment, one double cut guide 504 and the single cut guide 104 are located/positioned on a cutting platform 3202 toward the metatarsal fixation platform 110 and a plurality of double cut guides 504 are located/positioned on the cutting platform 3202 toward the cuneiform fixation platform 108. Further, the double cut guide 504 is located/positioned to the left of the single cut guide 104 on the metatarsal fixation platform 110 side of the cutting platform 3202.

In some embodiments, the double cut guides 504 and the single cut guide 104 are angled in the same direction (e.g., angled toward the left or toward the right with respect to the user (e.g., a medical professional)). In the illustrated embodiment, the double cut guide 504 and the single cut guide 104 on the same side of the positioning slot 106 are angled in the same direction and the plurality of double cut guides 504 on the opposite side of the positioning slot 106 are angled in a different direction.

In additional or alternative embodiments, the double cut guide 504 and the single cut guide 104 are positioned on the cutting platform 1402 such that there is an angle $(\theta_1)$, $(\theta_2)$, $(\theta_3)$, $(\theta_4)$, $(\theta_5)$, $(\theta_6)$, $(\theta_{x1})$, $(\theta_{x2})$, $(\theta_{x3})$, $(\theta_{x4})$, $(\theta_{x5})$, and $(\theta_{x6})$ created between the double cut guide 504 and the single cut guide 104 and the plurality of double cut guides 504, which may be any suitable angle. In various embodiments, the respective angles $(\theta_1)$, $(\theta_2)$, $(\theta_3)$, $(\theta_4)$, $(\theta_5)$, $(\theta_6)$, $(\theta_{x1})$, $(\theta_{x2})$, $(\theta_{x3})$, $(\theta_{x4})$, $(\theta_{x5})$, and $(\theta_{x6})$ may each be in the range of about 15° to about 75°.

Figure 33:
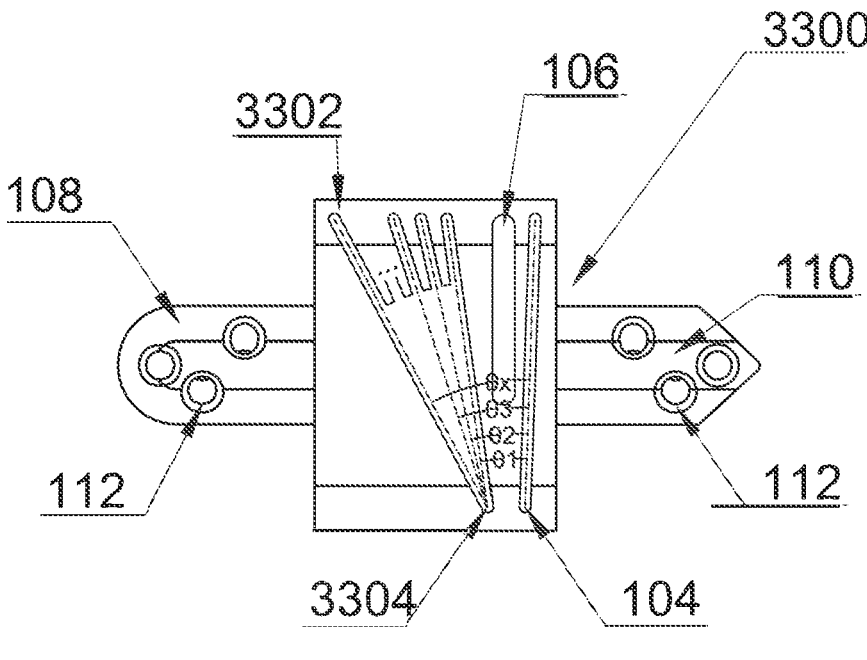
FIG. 33 is a diagram illustrating one embodiment of a surgical cutting block including a multi-cut guide and a single cut guide.

FIG. 33 is a diagram illustrating one embodiment of a surgical cutting block 3300 including a multi-cut guide 3304 and a single cut guide 104. In this embodiment, the multi-cut guide 3304 is located/positioned on the cutting platform 102 toward the cuneiform fixation platform 108 and the single cut guide 104 is located/positioned on a cutting platform 3202 toward the metatarsal fixation platform 110.

The multi-cut guide 3304 includes three or more paths that can include any suitable size and/or width capable of accepting a surgical cutting tool (e.g., a scalpel, surgical knife, etc.) and provide a respective path for the surgical cutting tool to follow while the surgical cutting tool is being used to produce an incision in a patient. The multi-cut guide 3304 includes an angle, which can be any suitable angle (e.g., an angle in the range of about one degree (1°) to about 90 degrees)(90°) with respect to any suitable reference point that can provide a predetermined and/or target path for the surgical cutting tool to follow while the surgical cutting tool is cutting a patient and/or performing a surgical procedure. Further, the angle between each respective pair of paths may be any suitable angle.

In some embodiments, the multi-cut guide 3304 and the single cut guide 104 are angled in the same direction (e.g., angled toward the left or toward the right with respect to the user (e.g., a medical professional)). In the illustrated embodiment, the multi-cut guide 3304 and the single cut guide 104 are angled in different directions.

In additional or alternative embodiments, the multi-cut guide 3304 and the single cut guide 104 are positioned on the cutting platform 1402 such that there is an angle $(\theta_1)$, $(\theta_2)$, and $(\theta_x)$ created between the multi-cut guide 3304 and the single cut guide 104, which may be any suitable angle. In various embodiments, the respective angles $(\theta_1)$, $(\theta_2)$, and $(\theta_x)$ may each be in the range of about 15° to about 75°.

Figure 34:
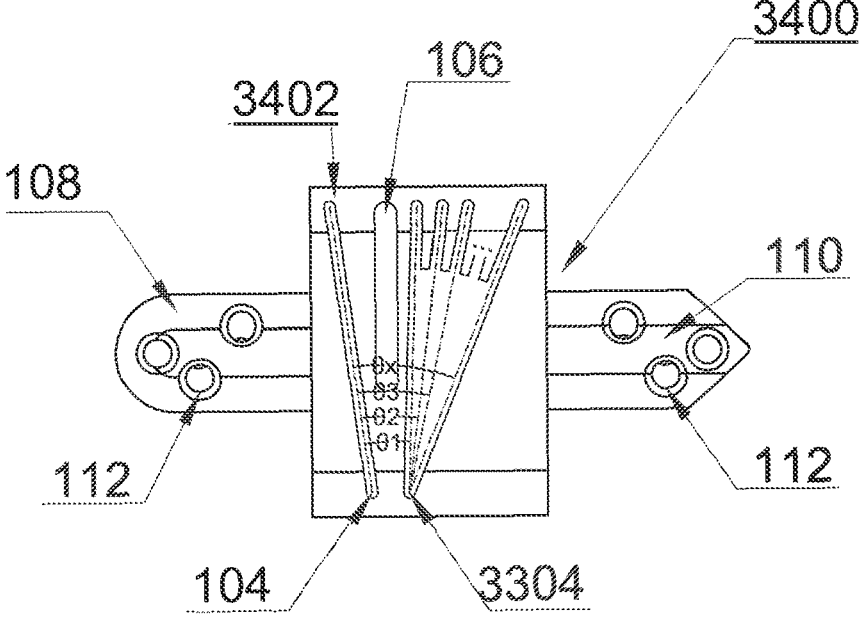
FIG. 34 is a diagram illustrating another embodiment of a surgical cutting block including a multi-cut guide and a single cut guide.

FIG. 34 is a diagram illustrating another embodiment of a surgical cutting block 3400 including a multi-cut guide 3304 and a single cut guide 104. In this embodiment, the multi-cut guide 3304 is located/positioned on a cutting platform 3402 toward the metatarsal fixation platform 110 and the single cut guide 104 is located/positioned on the cutting platform 3402 toward the cuneiform fixation platform 108.

In some embodiments, the multi-cut guide 3304 and the single cut guide 104 are angled in the same direction (e.g., angled toward the left or toward the right with respect to the user (e.g., a medical professional)). In the illustrated embodiment, the multi-cut guide 3304 and the single cut guide 104 are angled in different directions.

In additional or alternative embodiments, the multi-cut guide 3304 and the single cut guide 104 are positioned on the cutting platform 1402 such that there is an angle $(\theta_1)$, $(\theta_2)$, and $(\theta_x)$ created between the multi-cut guide 3304 and the single cut guide 104, which may be any suitable angle. In various embodiments, the respective angles $(\theta_1)$, $(\theta_2)$, and $(\theta_x)$ may each be in the range of about 15° to about 75°.

Figure 35:
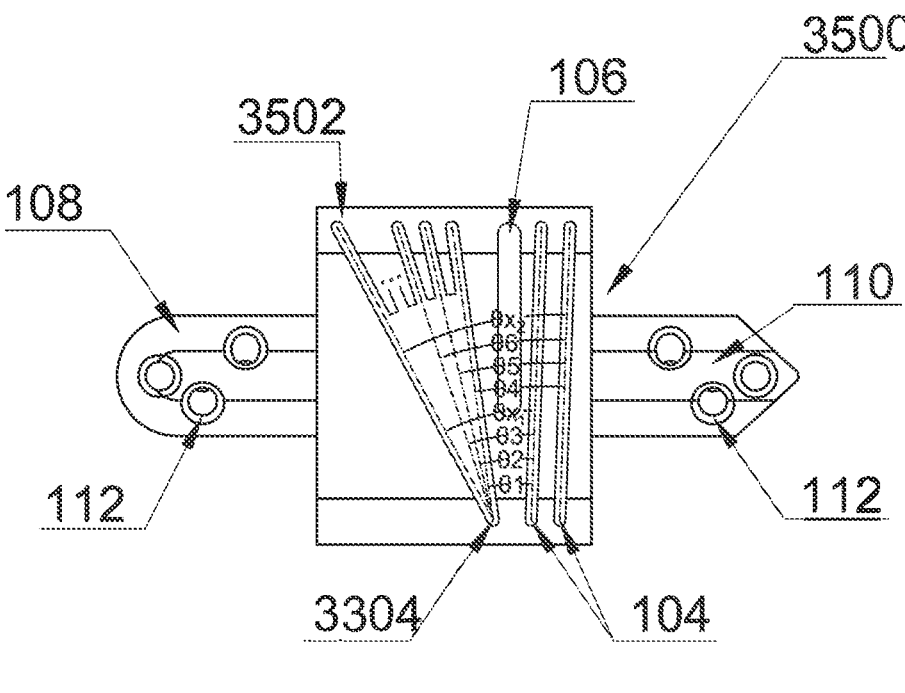
FIG. 35 is a diagram illustrating one embodiment of a surgical cutting block including a multi-cut guide and a plurality of single cut guides.

FIG. 35 is a diagram illustrating one embodiment of a surgical cutting block 3500 including a multi-cut guide 3304 and a plurality of single cut guides 104. In this embodiment, the multi-cut guide 3304 is located/positioned on a cutting platform 3502 toward the cuneiform fixation platform 108 and the plurality of single cut guides 104 are located/positioned on the cutting platform 3502 toward the metatarsal fixation platform 110.

In some embodiments, the multi-cut guide 3304 and the plurality of single cut guides 104 are angled in the same direction (e.g., angled toward the left or toward the right with respect to the user (e.g., a medical professional)). In the illustrated embodiment, the multi-cut guide 3304 and the plurality of single cut guides 104 are angled in different directions.

In additional or alternative embodiments, the multi-cut guide 3304 and the plurality of single cut guides 104 are positioned on the cutting platform 1402 such that there is an angle $(\theta_1)$, $(\theta_2)$, $(\theta_3)$, $(\theta_4)$, $(\theta_{x1})$, and $(\theta_{x2})$ created between the multi-cut guide 3304 and the plurality of single cut guides 104, which may be any suitable angle. In various embodiments, the respective angles $(\theta_1)$, $(\theta_2)$, $(\theta_3)$, $(\theta_4)$, $(\theta_{x1})$, and $(\theta_{x2})$ may each be in the range of about 15° to about 75°.

Figure 36:
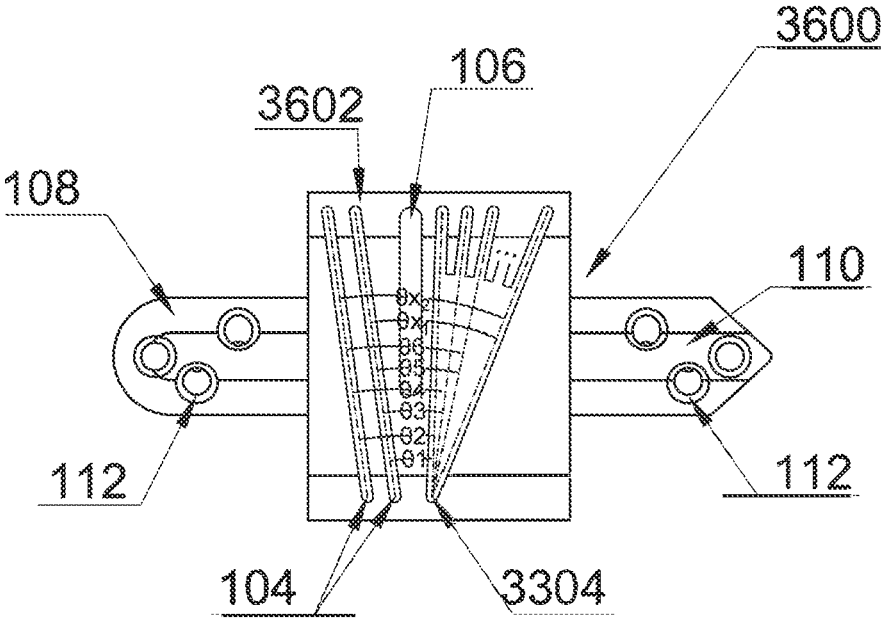
FIG. 36 is a diagram illustrating another embodiment of a surgical cutting block including a multi-cut guide and a plurality of single cut guides.

FIG. 36 is a diagram illustrating another embodiment of a surgical cutting block 3600 including a multi-cut guide 3304 and a plurality of single cut guides 104. In this embodiment, the multi-cut guide 3304 is located/positioned on a cutting platform 3602 toward the metatarsal fixation platform 110 and the plurality of single cut guides 104 are located/positioned on the cutting platform 3602 toward the cuneiform fixation platform 108.

In some embodiments, the multi-cut guide 3304 and the plurality of single cut guides 104 are angled in the same direction (e.g., angled toward the left or toward the right with respect to the user (e.g., a medical professional)). In the illustrated embodiment, the multi-cut guide 3304 and the plurality of single cut guides 104 are angled in different directions.

In additional or alternative embodiments, the multi-cut guide 3304 and the plurality of single cut guides 104 are positioned on the cutting platform 1402 such that there is an angle $(\theta_1)$, $(\theta_2)$, $(\theta_3)$, $(\theta_4)$, $(\theta_{x1})$, and $(\theta_{x2})$ created between the multi-cut guide 3304 and the plurality of single cut guides 104, which may be any suitable angle. In various embodiments, the respective angles $(\theta_1)$, $(\theta_2)$, $(\theta_3)$, $(\theta_4)$, $(\theta_{x1})$, and $(\theta_{x2})$ may each be in the range of about 15° to about 75°.

Figure 37:
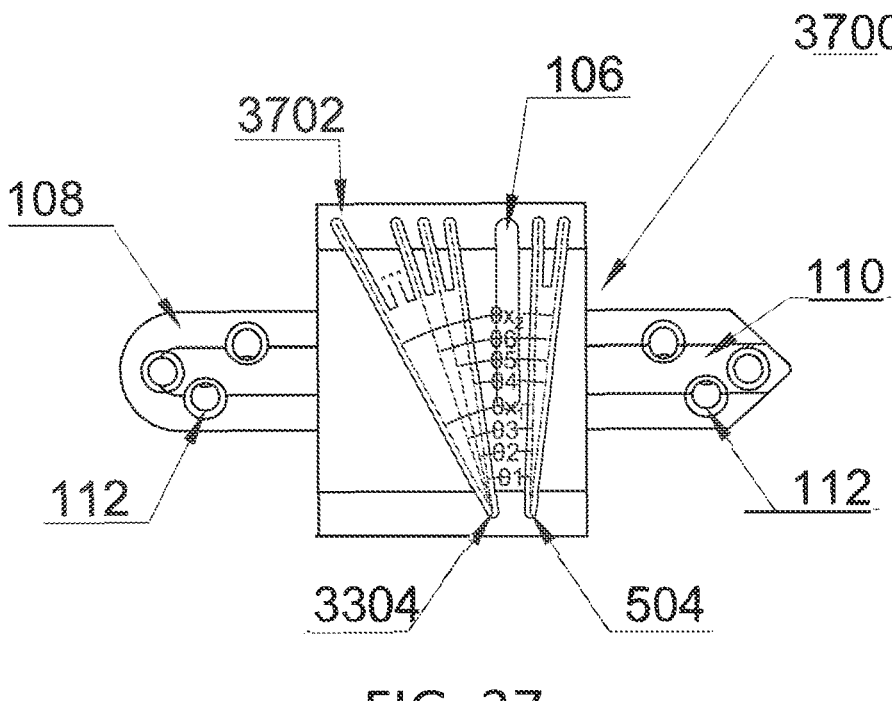
FIG. 37 is a diagram illustrating one embodiment of a surgical cutting block including a multi-cut guide and a double cut guide.

FIG. 37 is a diagram illustrating one embodiment of a surgical cutting block 3700 including a multi-cut guide 3304 and a double cut guide 504. In this embodiment, the multi-cut guide 3304 is located/positioned on a cutting platform 3702 toward the cuneiform fixation platform 108 and the double cut guide 504 is located/positioned on the cutting platform 3702 toward the metatarsal fixation platform 110.

In some embodiments, the multi-cut guide 3304 and the double cut guide 504 are angled in the same direction (e.g., angled toward the left or toward the right with respect to the user (e.g., a medical professional)). In the illustrated embodiment, the multi-cut guide 3304 and the double cut guide 504 are angled in different directions.

In additional or alternative embodiments, the multi-cut guide 3304 and the double cut guide 504 are positioned on the cutting platform 1402 such that there is an angle $(\theta_1)$, $(\theta_2)$, $(\theta_3)$, $(\theta_4)$, $(\theta_{x1})$, and $(\theta_{x2})$ created between the multi-cut guide 3304 and the double cut guide 504, which may be any suitable angle. In various embodiments, the respective angles $(\theta_1)$, $(\theta_2)$, $(\theta_3)$, $(\theta_4)$, $(\theta_{x1})$, and $(\theta_{x2})$ may each be in the range of about 15° to about 75°.

Figure 38:
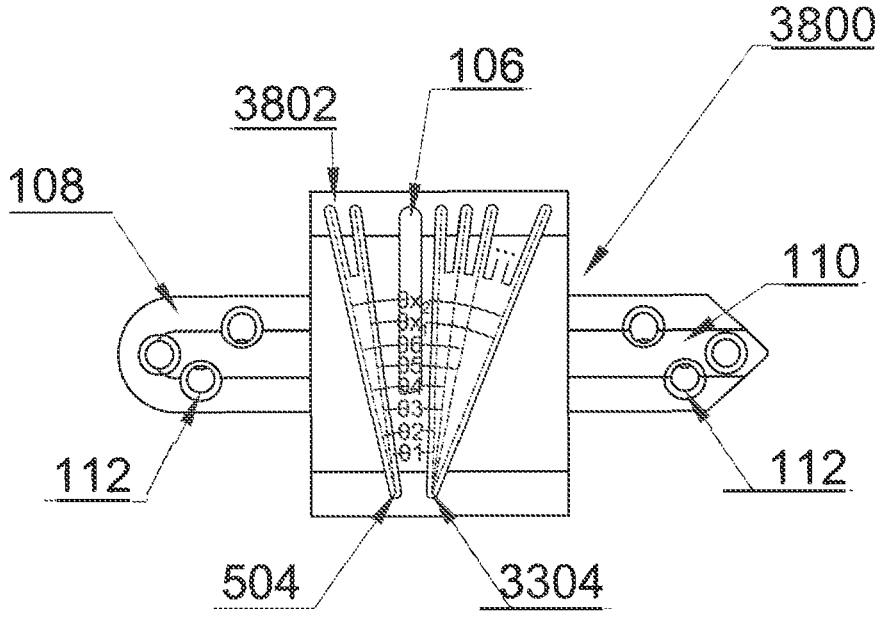
FIG. 38 is a diagram illustrating another embodiment of a surgical cutting block including a multi-cut guide and a double cut guide.

FIG. 38 is a diagram illustrating another embodiment of a surgical cutting block 3800 including a multi-cut guide 3304 and a double cut guide 504. In this embodiment, the multi-cut guide 3304 is located/positioned on a cutting platform 3802 toward the metatarsal fixation platform 110 and the double cut guide 504 is located/positioned on the cutting platform 3802 toward the cuneiform fixation platform 108.

In some embodiments, the multi-cut guide 3304 and the double cut guide 504 are angled in the same direction (e.g., angled toward the left or toward the right with respect to the user (e.g., a medical professional)). In the illustrated embodiment, the multi-cut guide 3304 and the double cut guide 504 are angled in different directions.

In additional or alternative embodiments, the multi-cut guide 3304 and the double cut guide 504 are positioned on the cutting platform 1402 such that there is an angle $(\theta_1)$, $(\theta_2)$, $(\theta_3)$, $(\theta_4)$, $(\theta_{x1})$, and $(\theta_{x2})$ created between the multi-cut guide 3304 and the double cut guide 504, which may be any suitable angle. In various embodiments, the respective angles $(\theta_1)$, $(\theta_2)$, $(\theta_3)$, $(\theta_4)$, $(\theta_{x1})$, and $(\theta_{x2})$ may each be in the range of about 15° to about 75°.

Figure 39:
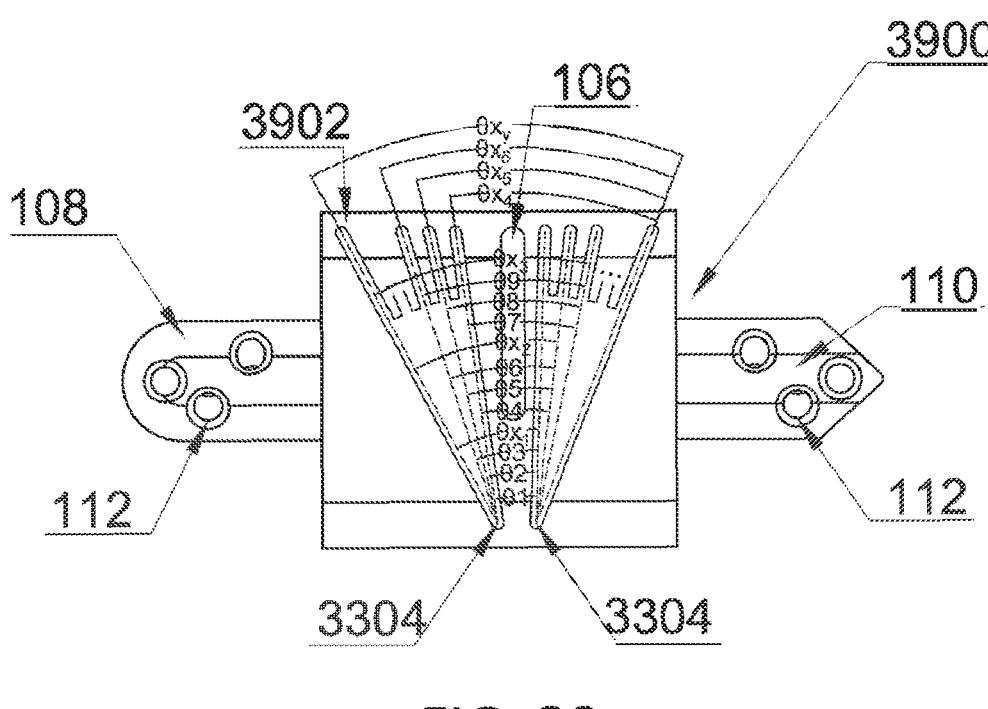
FIG. 39 is a diagram illustrating one embodiment of a surgical cutting block including a plurality of multi-cut guides.

FIG. 39 is a diagram illustrating one embodiment of a surgical cutting block 3900 including a plurality of multi-cut guides 3304. In this embodiment, a multi-cut guide 3304 is located/positioned on a cutting platform 3902 on both sides of the positioning slot 106.

In some embodiments, the multi-cut guides 3304 are angled in the same direction (e.g., angled toward the left or toward the right with respect to the user (e.g., a medical professional)). In the illustrated embodiment, the multi-cut guides 3304 are angled in different directions.

In additional or alternative embodiments, the multi-cut guides 3304 are positioned on the cutting platform 1402 such that there is an angle $(\theta_1)$, $(\theta_2)$, $(\theta_3)$, $(\theta_4)$, $(\theta_{x1})$, $(\theta_{x2})$, $(\theta_{x3})$, $(\theta_{x4})$, and $(\theta_{x5})$ created between the multi-cut guides 3304, which may be any suitable angle. In various embodiments, the respective angles $(\theta_1)$, $(\theta_2)$, $(\theta_3)$, $(\theta_4)$, $(\theta_{x1})$, $(\theta_{x2})$, $(\theta_{x3})$, $(\theta_{x4})$, and $(\theta_{x5})$ may each be in the range of about 15° to about 75°.

Figure 40A:
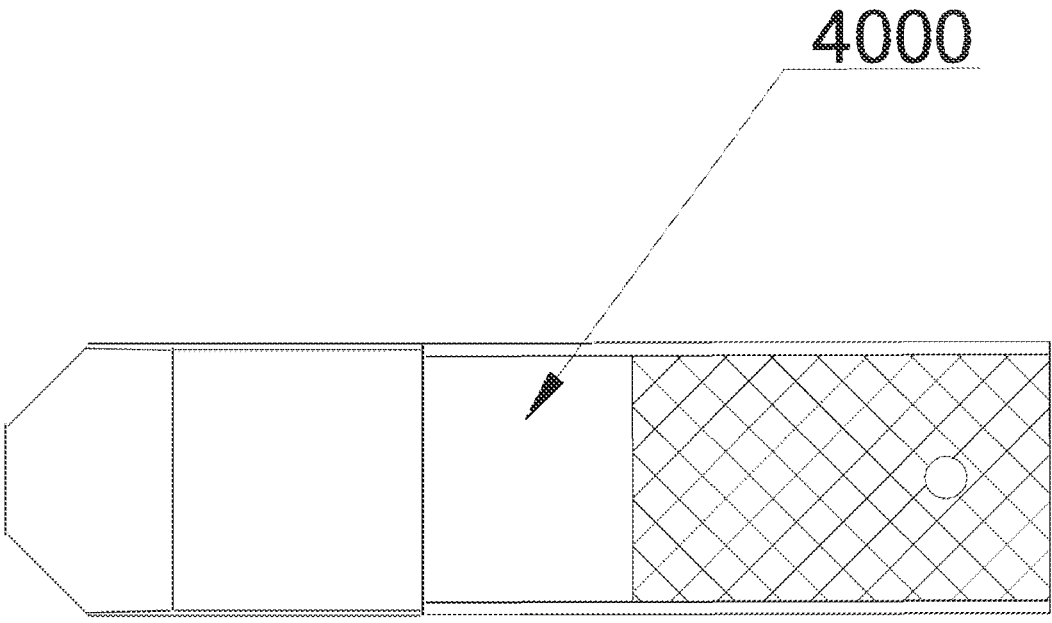
FIG. 40A is a diagram illustrating one embodiment of a positioning fin.

FIG. 40A is a diagram illustrating one embodiment of a positioning fin 4000. The positioning guide 4000 may include any shape and/or size that can be accommodated by a positioning slot 106.

Further, the positioning guide 4000 may include and/or be formed of any suitable material. In some embodiments, the positioning guide 4000 includes a sterilizable material.

Figure 40B:
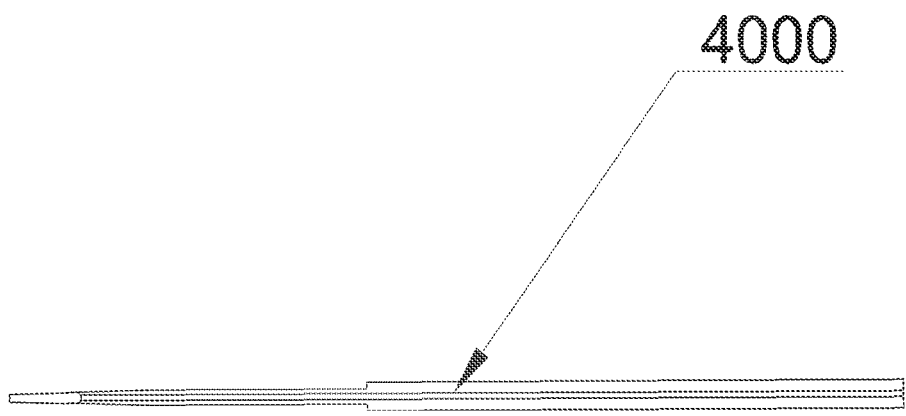
FIG. 40B is a diagram illustrating a profile view of the positioning fin illustrated in FIG. 40A.
Figure 41:
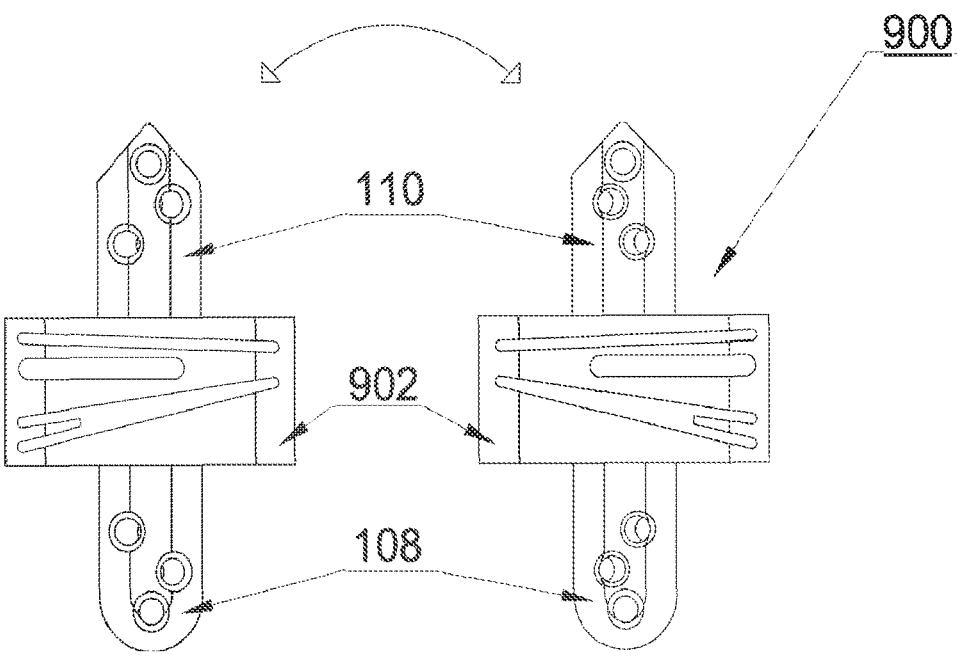
FIG. 41 is a diagram illustrating that opposite sides of a surgical cutting block can be used on the left foot and the right foot of a patient.

FIG. 40B is a diagram illustrating a profile view of the positioning fin illustrated in FIG. 40A. FIG. 41 is a diagram illustrating that opposite sides of surgical cutting blocks 100 through 3900 can be used on the left foot and/or the right foot of a patient.

The positioning guide 4000 and the positioning slot 106 are configured to cooperatively prepare a cuneiform-metatarsal joint for a surgical procedure. In some embodiments, the positioning guide 4000 and the positioning slot 106 are configured to cooperatively guide the positioning of a surgical cutting block (e.g., surgical cutting blocks 100 through 3900) at a cuneiform-metatarsal joint in preparation for a surgical procedure (e.g., a surgery to correct a bunion).

Figure 42A:
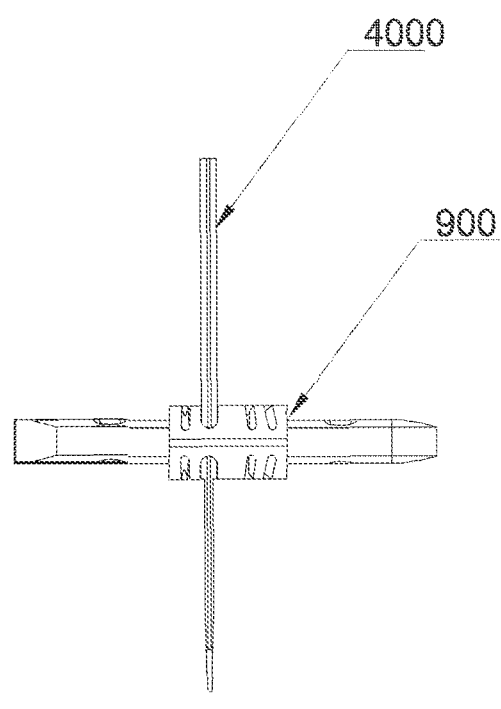
FIG. 42A is a diagram illustrating a profile view of one embodiment of a positioning fin and a surgical cutting board engaged with one another.
Figure 42B:
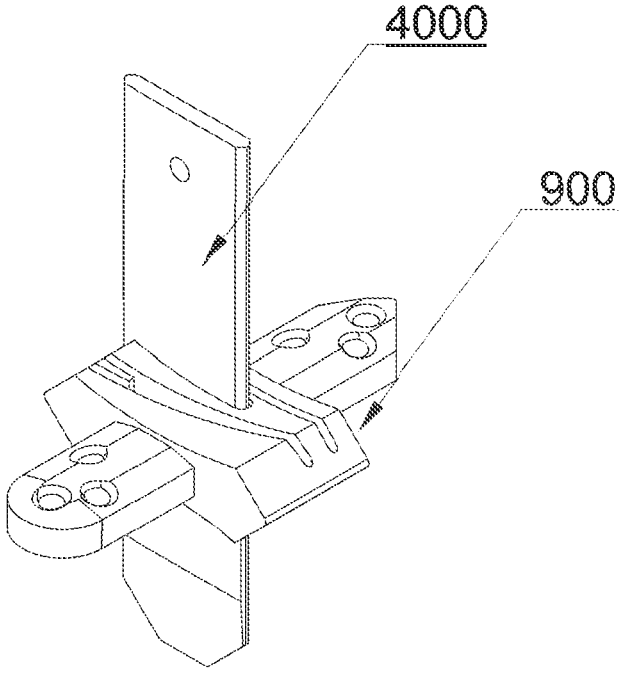
FIG. 42B is a diagram illustrating a closer view of the positioning fin and surgical cutting board illustrated in FIG. 42A.

A cutting platform (e.g., cutting platforms 102 through 3902) allows a cut guide (e.g., single cut guide(s) 104, double cut guide(s) 504, and/or multi-cut guide(s) 3304) to sit close to a bone surface. Surgical cutting blocks 100 through 3900 may be placed in the correct position by placing the positioning fin 4000 through the positioning slot 106 in the cutting portion (see, e.g., FIGS. 42A & 42B). The positioning fin 4000 is placed through the positioning slot 106 to allow the cut guide to placed centrally on a joint.

The cut guides are held in place using pins driven through the wire holes 112 into the cuneiform and metatarsal. Some wire holes 112 may include an angle while others are perpendicular to the surface of a cut guide.

Figure 43A:
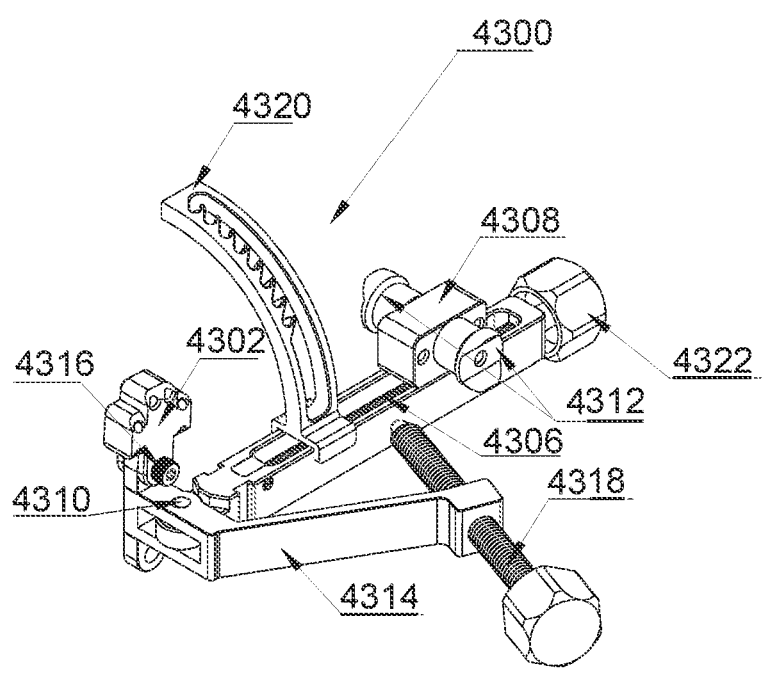
FIG. 43A is a diagram illustrating a non-planar view of one embodiment of a surgical jig.
Figure 43B:
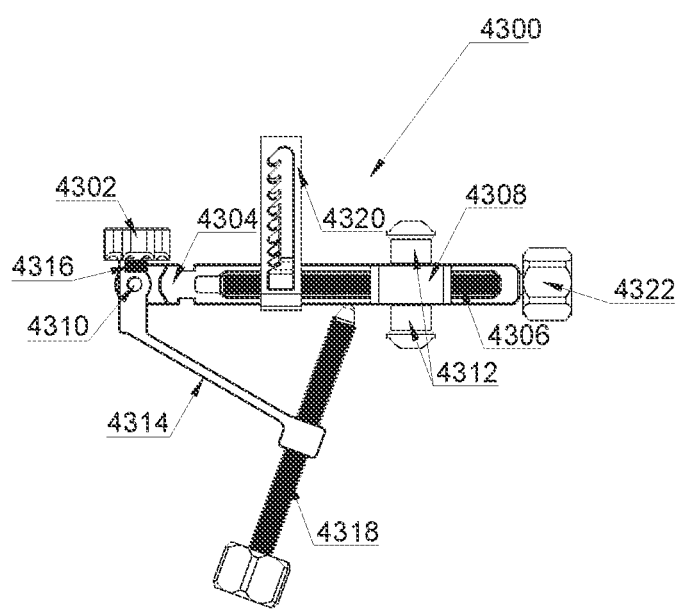
FIG. 43B is a diagram illustrating a top view of the surgical jig illustrated on FIG. 43A.

FIG. 43A is a diagram illustrating a non-planar view of one embodiment of a surgical jig 4300 and FIG. 43B is a diagram illustrating a top view of the surgical jig 4300. At least in the illustrated embodiment, the surgical jig 4300 includes, among other components, an attachment body 4302, a rail body 4304, a distraction body 4308 coupled to a set of distraction threads 4306, a rail hinge 4310, a metatarsal contact 4312, an arm 4314, an attachment screw 4316, a rail adjustment screw 4318, and a rotation guide 4320.

The surgical jig 4300 may be formed of any suitable material (e.g., a metal, an alloy, a plastic, a composite, and/or a graphite material, etc., among other materials that are possible and contemplated herein). In certain embodiments, the material included in and/or forming the surgical jig 4300 is sterilizable.

In certain embodiments, the attachment body 4302, rail body 4304, set of distraction threads 4306, distraction body 4308, rail hinge 4310, metatarsal contact 4312, arm 4314, attachment screw 4316, rail adjustment screw 4318, and rotation guide 4320 all include and/or are formed of the same or substantially the same material(s). In other embodiments, at least two of the attachment body 4302, rail body 4304, set of distraction threads 4306, distraction body 4308, rail hinge 4310, metatarsal contact 4312, arm 4314, attachment screw 4316, rail adjustment screw 4318, and rotation guide 4320 include and/or are formed of the same or substantially the same material(s).

In some embodiments, the attachment body 4302, rail body 4304, set of distraction threads 4306, distraction body 4308, rail hinge 4310, metatarsal contact 4312, arm 4314, attachment screw 4316, rail adjustment screw 4318, and rotation guide 4320 all include and/or are formed of different materials. In other embodiments, at least two of the attachment body 4302, rail body 4304, set of distraction threads 4306, distraction body 4308, rail hinge 4310, metatarsal contact 4312, arm 4314, attachment screw 4316, rail adjustment screw 4318, and rotation guide 4320 include and/or are formed of different materials.

The surgical jig 4300 may include any suitable dimensions capable of facilitating its various functions in performing an osteotomy. That is, the surgical jig 4300 and/or its various components may include any suitable length, width, height, and/or diameter, etc., among other dimensions that are possible and contemplated herein.

In various embodiments, the attachment body 4302 is configured to attach the surgical jig 4300 to a cuneiform of a patient. The attachment body 4302 includes a set of apertures in which one or more of the apertures are angled apertures and one or more of the apertures are straight apertures. Surgical pins can be inserted through the apertures and into the patient's cuneiform to attach the surgical jig 4300 to the cuneiform.

The rail body 4304, in certain embodiments, includes a shape configured to run adjacent to a first metatarsal of the patient. Movement of the rail body 4304 is controlled by the rail adjustment screw 4318 so that the distraction body 4308 and/or the metatarsal contact 4312 can apply force on the patient's metatarsal to correct its position. The rail body 4304 can also act as a housing for the set of distraction threads 4306 so that when a knob 4322 coupled to the set of distraction threads 4306 is turned, the distraction body 4308 to move to compress and compact the patient's cuneiform-metatarsal joint.

The function of the rotation guide 4320 may also be dependent on the distraction body 4308. Here, as the distraction body 4308 moves along the rail body 4304, the distraction body 4308 provides stability to the rotation guide 4320 to hold any rotation created by the rotation guide in a patient's metatarsal. In some embodiments, the rail body 4304 includes a set of notches that allow for the removal of the rotation guide 4320.

The knob 4322, the set of distraction threads 4306, and the distraction body 4308 are configured to cooperatively function to compress or distract the cuneiform-metatarsal joint of a patient. The rotation of the knob 4322 rotates the set of distraction threads 4306, which are coupled to the distraction body 4308, and moves the distraction body 4308 along the rail body 4304. When pins are placed through the distraction body 4308 and into the patient's metatarsal, movement of the distraction body 4308 along the rail body 4304 will result in the joint being compressed or distracted.

As shown, the distraction body 4308 is threaded onto the set of distraction threads 4306 and the set of distraction threads 4306 use the length of the rail body 4304 as a path to move along when the knob 4322 is turned. A set of holes through the distraction body 4308 allow for a set of pins to be placed into the patient's metatarsal for compaction and/or distraction.

The rail hinge 4310 may include any suitable hinging mechanism that can allow the rail body 4304 to pivot laterally. In certain embodiments, the rail hinge 4310 includes a bolt attaching the rail body 4304 and the arm 4314, which can allow the arm 4314 to rotate and/or pivot freely. In some embodiments, the arm 4314 can be removed so that the surgical jig 4300 can be reassembled into a right or left configuration for performing a procedure on a right foot or a left foot, as discussed in greater detail below with reference to FIG. 44.

A metatarsal contact 4312 includes a rotating piece and/or mechanism with a shape configured to match the curvature of a patient's metatarsal. The curvature is configured to prevent slipping when correcting the position and/or angle of the patient's metatarsal. The rotation allows the curvature of the metatarsal contact 4312 to wrap around at least a portion of the target bone for various placements of the surgical jig 4300.

The arm 4314 is configured to hold the rail adjustment screw 4318 so that the rail adjustment screw 4318 can push the rail body 4304 when the rail adjustment screw 4318 is rotated. The arm 4314 is a structural piece that is coupled to the attachment body 4302, rail body 4304, and rail adjustment screw 4318. The arm 4314, in some embodiments, is further configured for use in switching between the left and right configurations illustrated in FIG. 44.

The attachment screw 4316 is configured to lock the rotation of the arm 4314 around the attachment body 4302. The attachment screw 4316 may include any suitable mechanism capable of locking the rotation of the arm 4314 around the attachment body 4302.

The rail adjustment screw 4318 is configured to apply a force to the rail body 4304 to push/move the rail body 4304 laterally. Laterally pushing and/or moving the rail body 4304, in turn, causes the rail body 4304 to laterally push and/or move the patient's metatarsal.

The rotation guide 4320 is configured to hold any amount of rotation applied to the patient's metatarsal. The rotation guide 4320, in various embodiments, includes a set of slots or notches through which a wire may be placed therethrough. The wire can be rotated and locked into the desired slot to hold a target amount of rotation applied to the patient's metatarsal. Alternatively, a wire can be placed through a sliding construct on the rotation guide 4320 and the patient's metatarsal can be locked into a target rotated position when the wire is at its desired rotated position.

Figure 44:
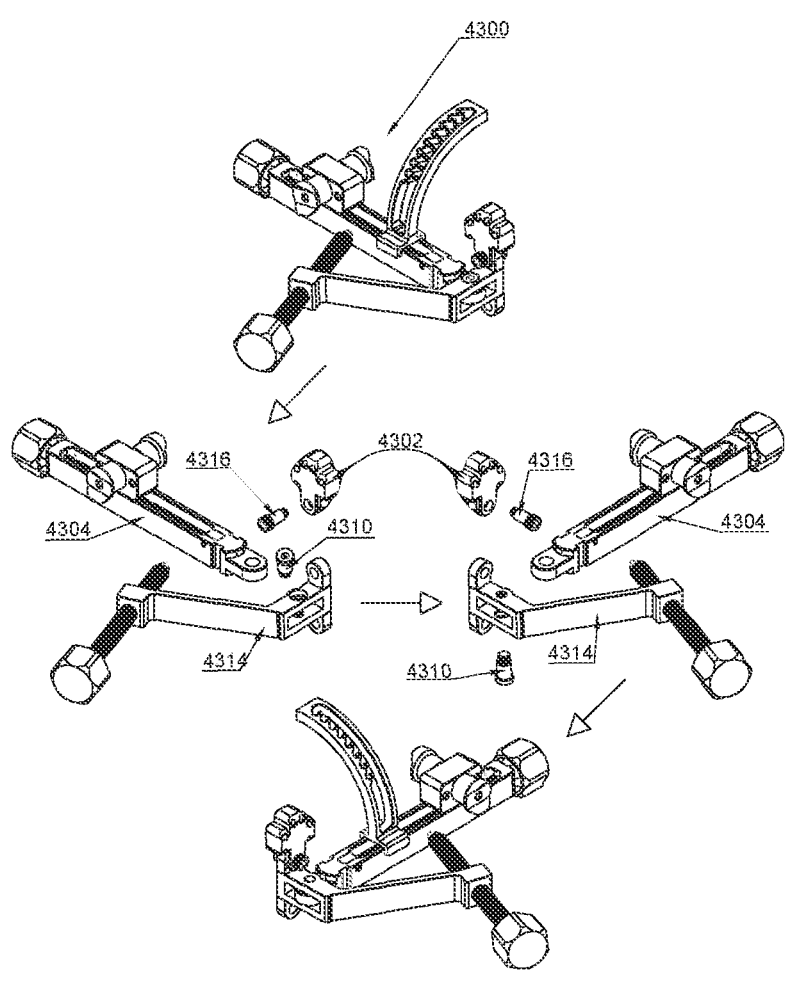
FIG. 44 is a diagram illustrating one embodiment of a surgical jig that is adjustable for performing an osteotomy on a left foot and/or a right foot.

Referring to FIG. 44, FIG. 44 is a diagram illustrating an embodiment of an adjustable surgical jig 4300. At least in the illustrated embodiment, the surgical jig 4300 is configured for use in performing an osteotomy on a left foot and/or a right foot.

The surgical jig 4300 can be adjusted by removing the rail screw 4310 and the attachment screw 4316 so that the orientation of the arm 4314 can be changed (e.g., turned over) to the desired orientation. In this embodiment, a metatarsal contact 4312 is included on both sides of the distraction body 4308. Here, a single surgical jig 4300 can be utilized to perform an osteotomy on both feet of a patient.

Figure 45:
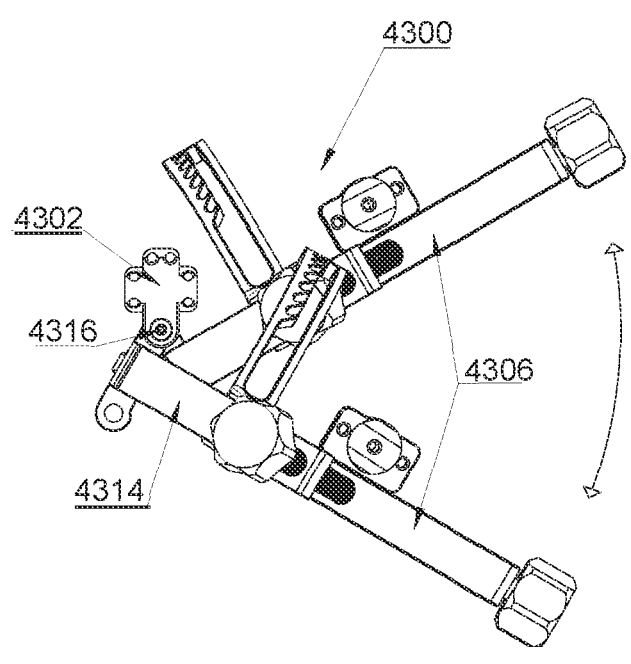
FIG. 45 is a diagram illustrating an embodiment of a surgical jig configured to vertically adjust.

FIG. 45 is a diagram illustrating an embodiment of a surgical jig 4300 configured to adjust vertically (e.g., from the cuneiform). The rotation at the junction of the attachment body 4302 and the arm 4314 allows and/or enables the surgical jig 4300 to be vertically positioned so that the patient's metatarsal rests in the curvature and/or groove of the metatarsal contact 4312. The rotation created at the junction of the attachment body 4302 and the arm 4314 can be locked by tightening the attachment screw 4316.

Figure 46:
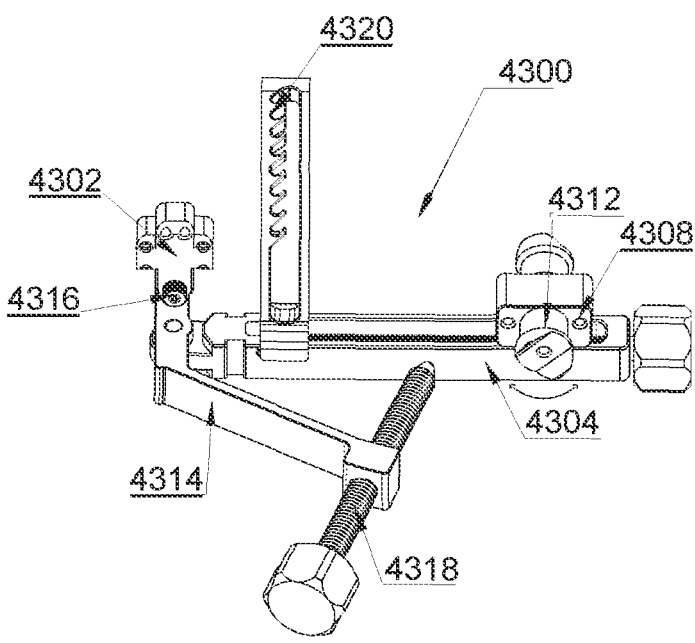
FIG. 46 is a diagram illustrating one embodiment of a surgical jig including a rotating metatarsal contact.

FIG. 46 is a diagram illustrating one embodiment of a surgical jig including a rotatable metatarsal contact 4312. In various embodiments, the metatarsal contact 4312, in addition to the positional function of the metatarsal contact 4312 discussed above, is configured to freely rotate. Rotating the metatarsal contact 4312 can allow/enable the best and/or proper fitment of the metatarsal contact 4312 with the patient's metatarsal.

Figure 47A:
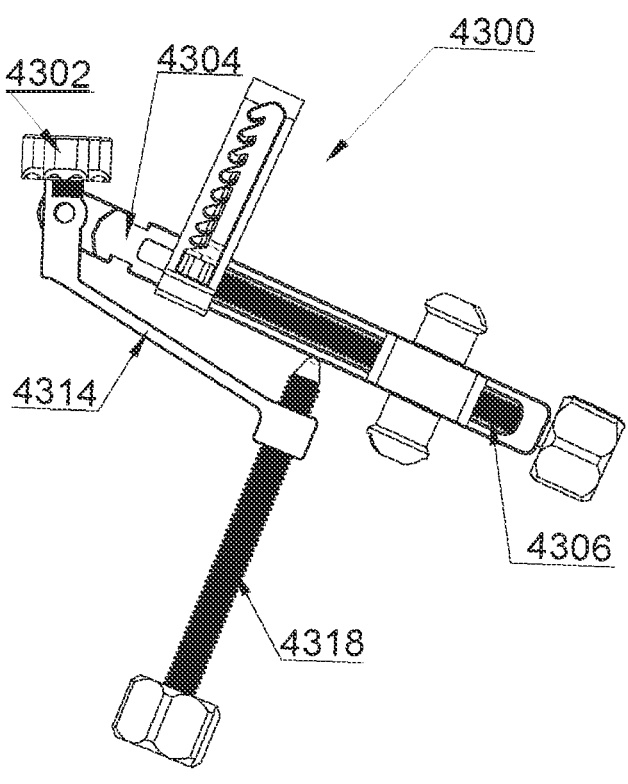
FIG. 47A is a diagram illustrating a first position of an embodiment of a surgical jig configured to laterally move a metatarsal.
Figure 47B:
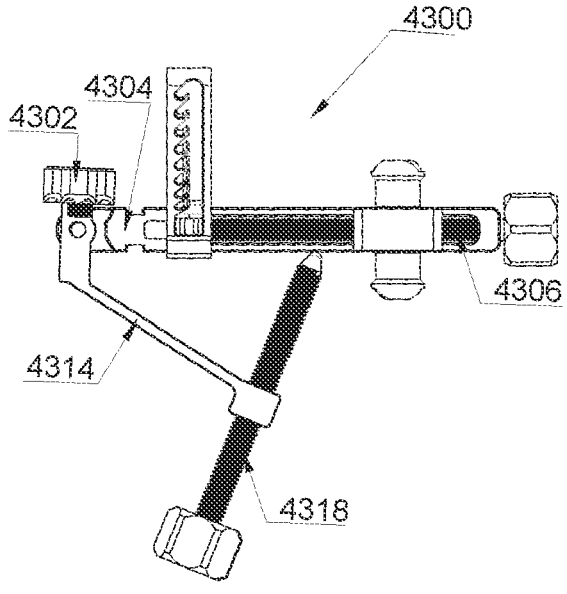
FIG. 47B is a diagram illustrating the surgical jig illustrated in FIG. 47A moved laterally to a second position.

FIGS. 47A and 47B are diagram illustrating an embodiment of the surgical jig 4300 configured to laterally move a patient's metatarsal (e.g., adjust the intermetatarsal (IM) angle) between various positions. Here, the attachment body 4302 is fixed and/or attached to the patient's cuneiform. The angle of the patient's metatarsal can be corrected by turning the rail adjustment screw 4318. The rail adjustment screw 4318 applies force to and pushes the rail body 4304 from a first position (see, e.g., FIG. 47A) to a second position (see, e.g., FIG. 47B), which in turn can cause the patient's metatarsal to change positions because the patient's metatarsal is in contact with the moving rail body 4304 via the metatarsal contact 4312.

Figure 48A:
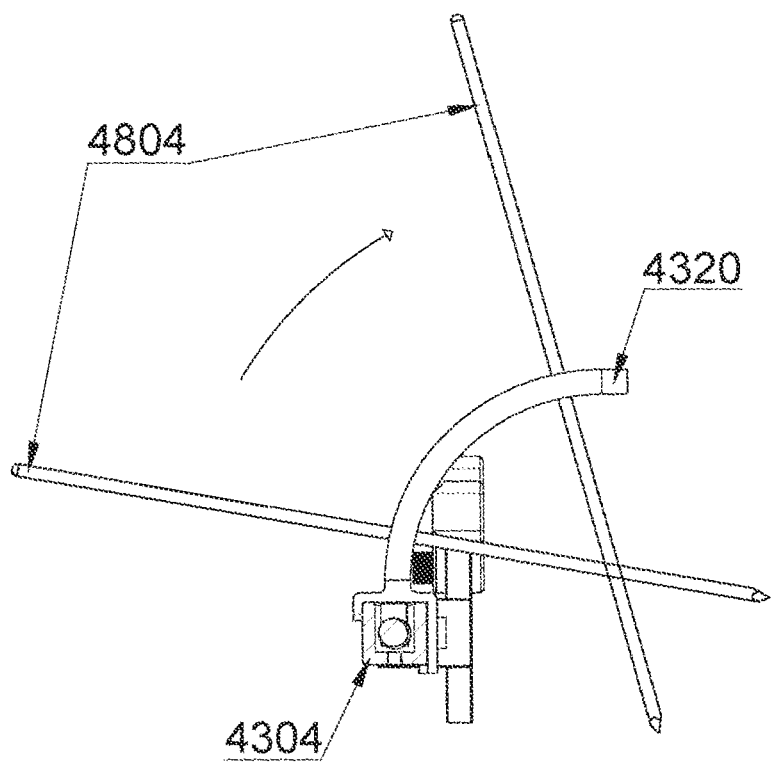
FIG. 48A is a diagram illustrating one embodiment of a surgical jig configured to rotate a metatarsal.
Figure 48B:
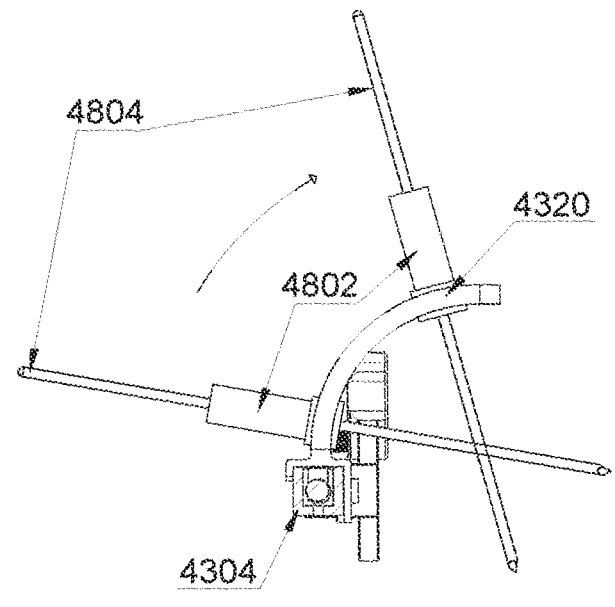
FIG. 48B is a diagram illustrating the surgical jig illustrated in FIG. 48A including a locking mechanism for at least temporarily locking a rotated position of the metatarsal.

FIG. 48A is a diagram illustrating one embodiment of a surgical jig 4300 configured to rotate a patient's metatarsal. Further, FIG. 48B is a diagram illustrating a surgical jig 4300 including a locking mechanism 4802 for at least temporarily locking a rotated position of the patient's metatarsal.

A wire 4804 or other suitable type of lever is placed through a slot in the rotation guide 4320 and into the patient's metatarsal. The wire 4804 can then be used to rotate the patient's metatarsal to a target rotational position. The rotation of the patient's metatarsal can then be locked into place (e.g., into one or the slots) via coupling the locking mechanism 4802 to the rotation guide 4320.

Figure 49A:
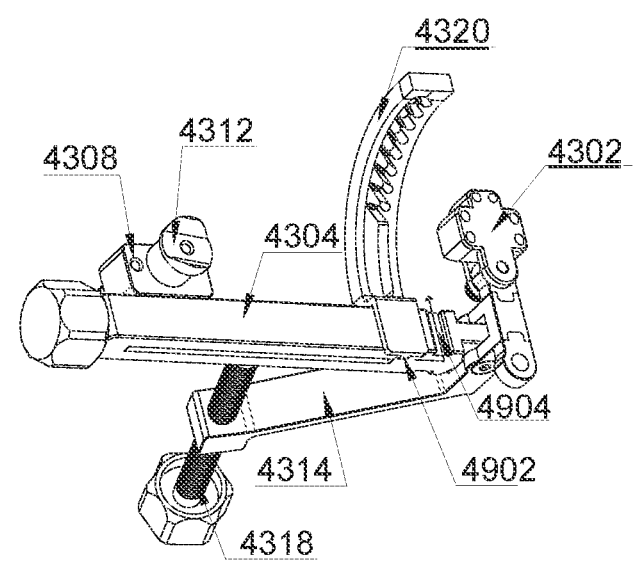
FIGS. 49A and 49B are diagrams illustrating an embodiment of removal of a rotation guide from a surgical jig.
Figure 49B:
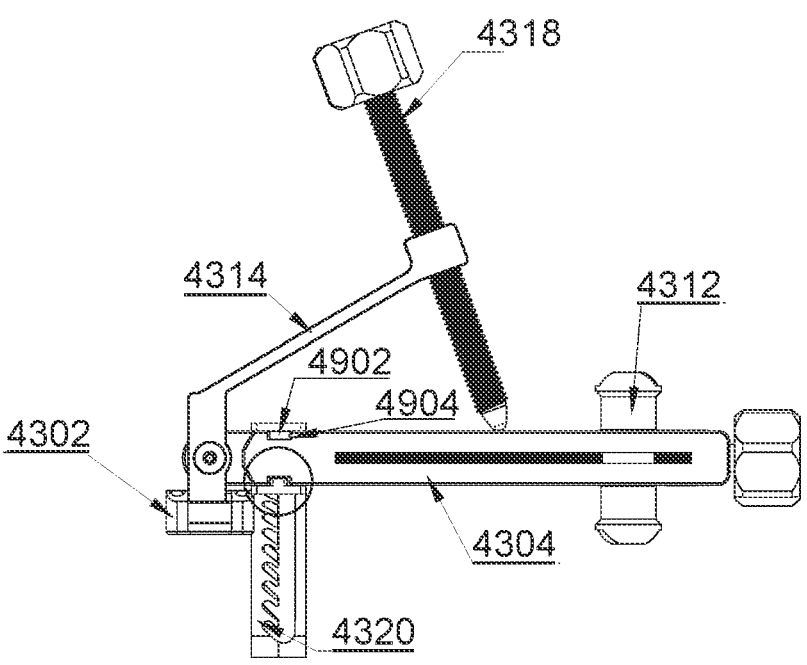

FIGS. 49A and 49B are diagram illustrating an embodiment of removal of a rotation guide 4320 from a surgical jig 4300. After the locking mechanism 4802, wire 4804, and rotation guide 4320 rotate the patient's metatarsal to the target rotational position, a set of pins are placed through a set of apertures formed in the distraction body 4308 to further lock the patient's metatarsal in its rotational position. The wire 4804 used in the rotation guide 4320 can then be removed from the rotation guide 4320 and the set of pins through the distraction body 4308 can hold the patient's metatarsal in place. The rotation guide 4320 can then be removed or left in place.

To remove rotation guide 4320, a tab 4902 on the bottom of the rotation guide 4320 can be aligned with a notch 4904 in the rail body 4304, as shown in FIG. 49A. Once the tab 4902 and the notch 4904 are aligned, the rotation guide 4320 can be removed by pulling up on the rotation guide 4320.

Figure 50A:
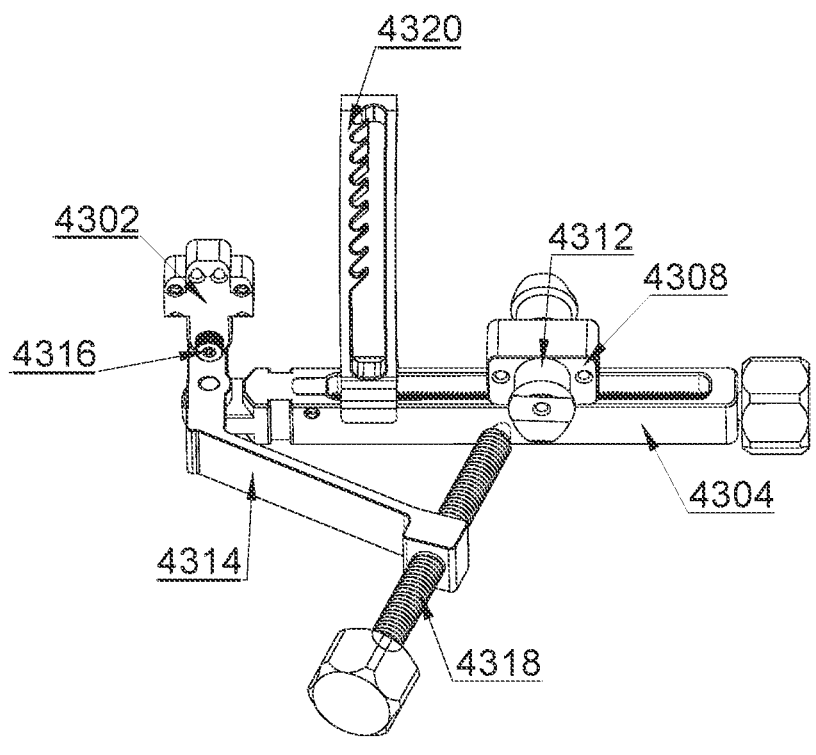
FIGS. 50A and 50B are diagrams illustrating one embodiment of a surgical jig including a distraction body configured to compress and/or distract a cuneiform-metatarsal joint.
Figure 50B:
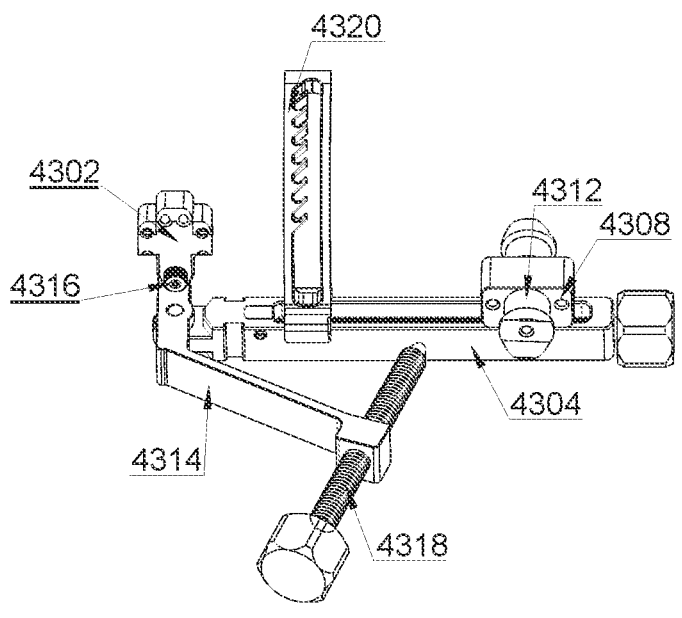

FIGS. 50A and 50B are diagrams illustrating one embodiment of a surgical jig 4300 including a distraction body 4308 configured to compress and/or distract the cuneiform-metatarsal joint of a patient. During operation, the knob 4322 coupled to the set of distraction threads 4306 can be rotated to move the distraction body 4308 along the rail body 4304, which acts as a rail and/or path. When one or more pins are placed through one or more apertures formed on the distraction body 4308 and into a patient's metatarsal, the turning of the knob 4322 (and the set of distraction threads 4306) causes the distraction body 4308 to move, which causes compression or distraction of the patient's cuneiform-metatarsal joint depending on the direction that the distraction body 4308 is moving. That is, the patient's cuneiform-metatarsal joint is compressed when the distraction body 4308 is moved along the rail body 4304 toward the rotation guide 4320 (see, e.g., FIG. 50A) and distracted when the distraction body 4308 is moved along the rail body 4304 away from the rotation guide 4320 (see, e.g., FIG. 50B).

Figure 51:
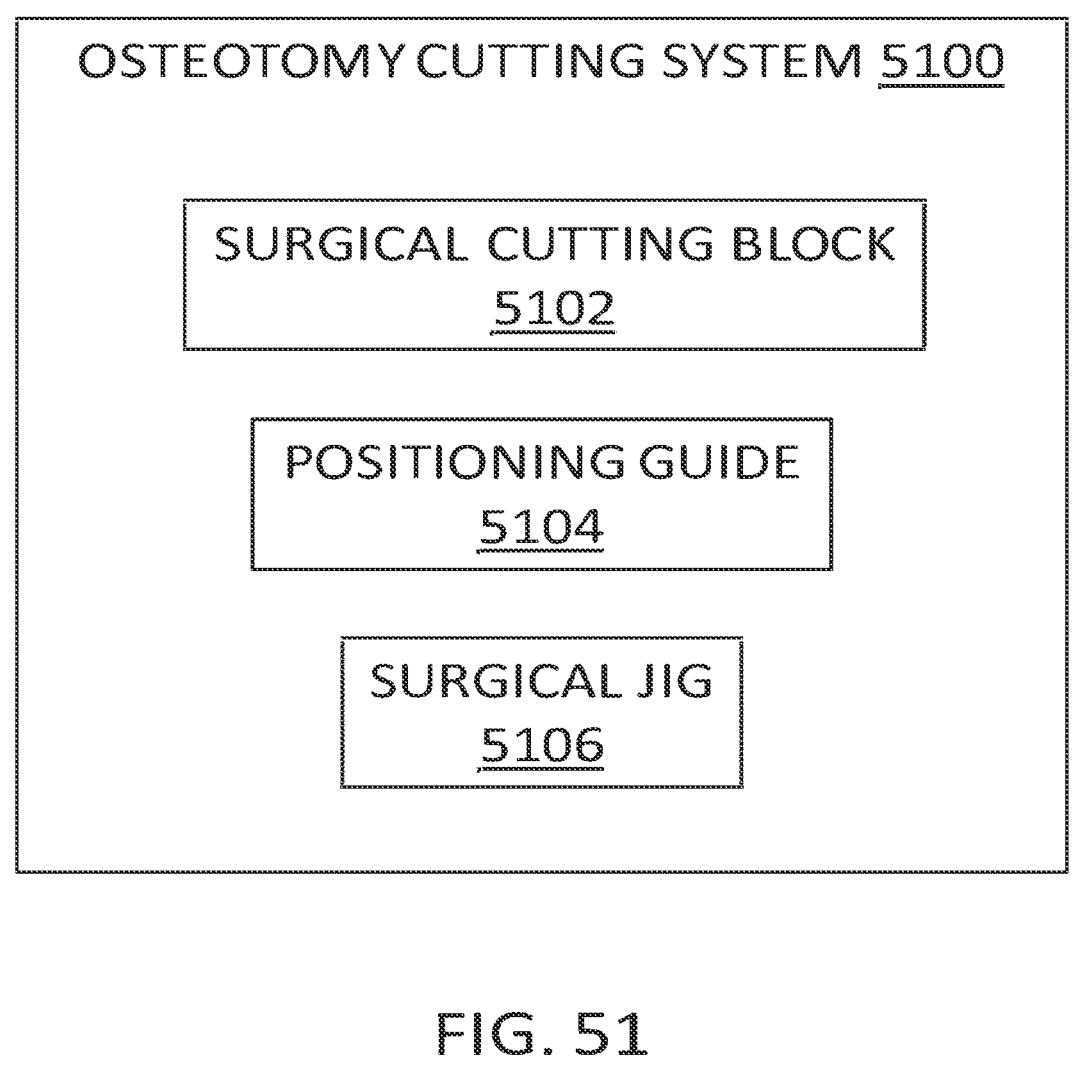

FIG. 51 is a block diagram of one embodiment of an osteotomy cutting system 5100. At least in the illustrated embodiment, the osteotomy cutting system 5100 includes, among other components, a surgical cutting block 5102, a positioning guide 5104, and a surgical jig 5106.

In various embodiments, the surgical cutting block 5102 can include any of the surgical cutting blocks 100 through 3900 discussed above with reference to FIGS. 1 through 39. Similarly, various embodiments of the positioning guide 5104 can include any of the positioning guides 4000 discussed above with reference to FIGS. 40A and 40B. Further, various embodiments of the surgical jig 5106 can include any of the surgical jigs 4300 discussed above with reference to FIGS. 43 through 50B.

Figure 52A:
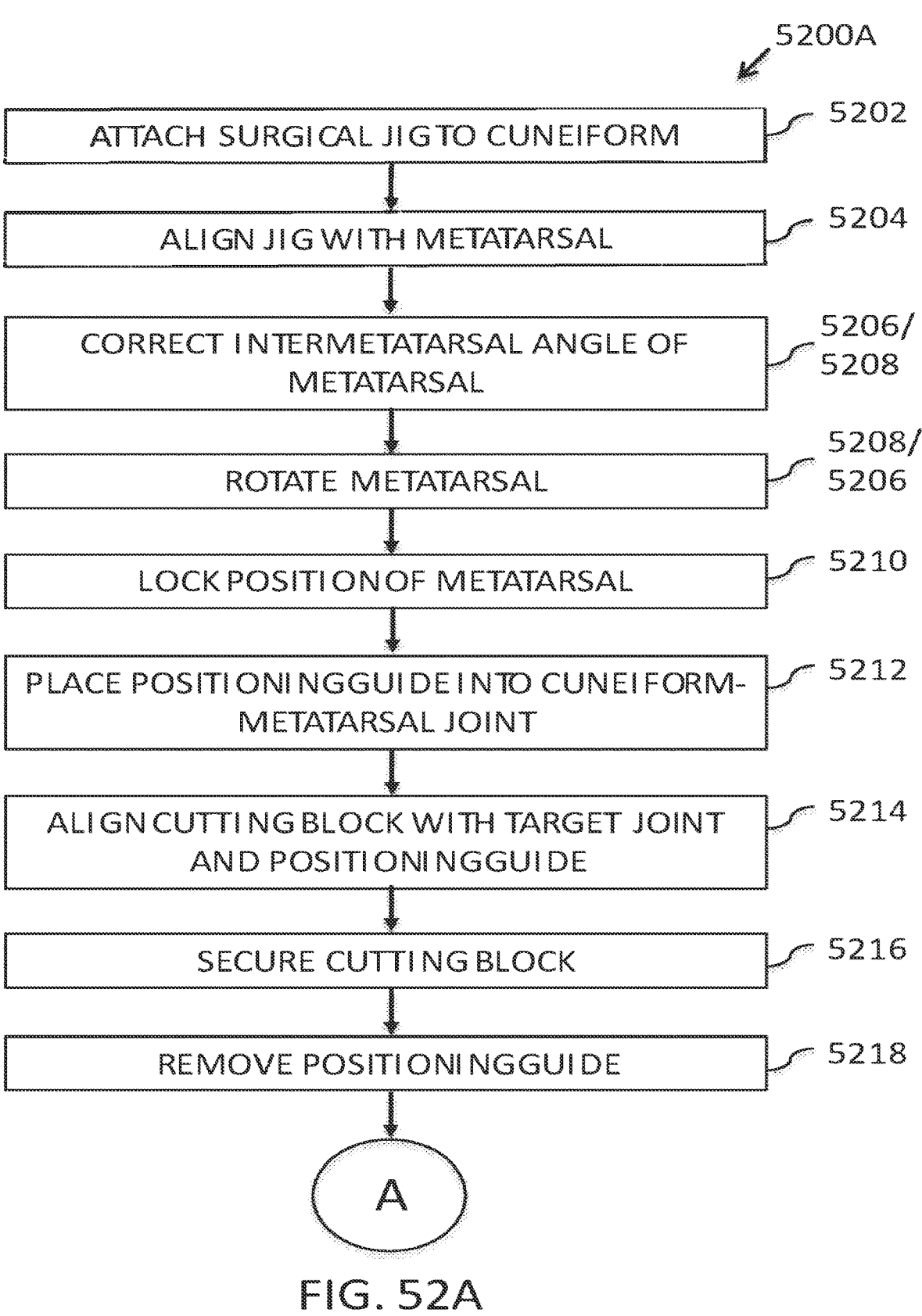
FIG. 52A is a flow diagram illustrating one embodiment of a method for performing an osteotomy.
Figure 52A:
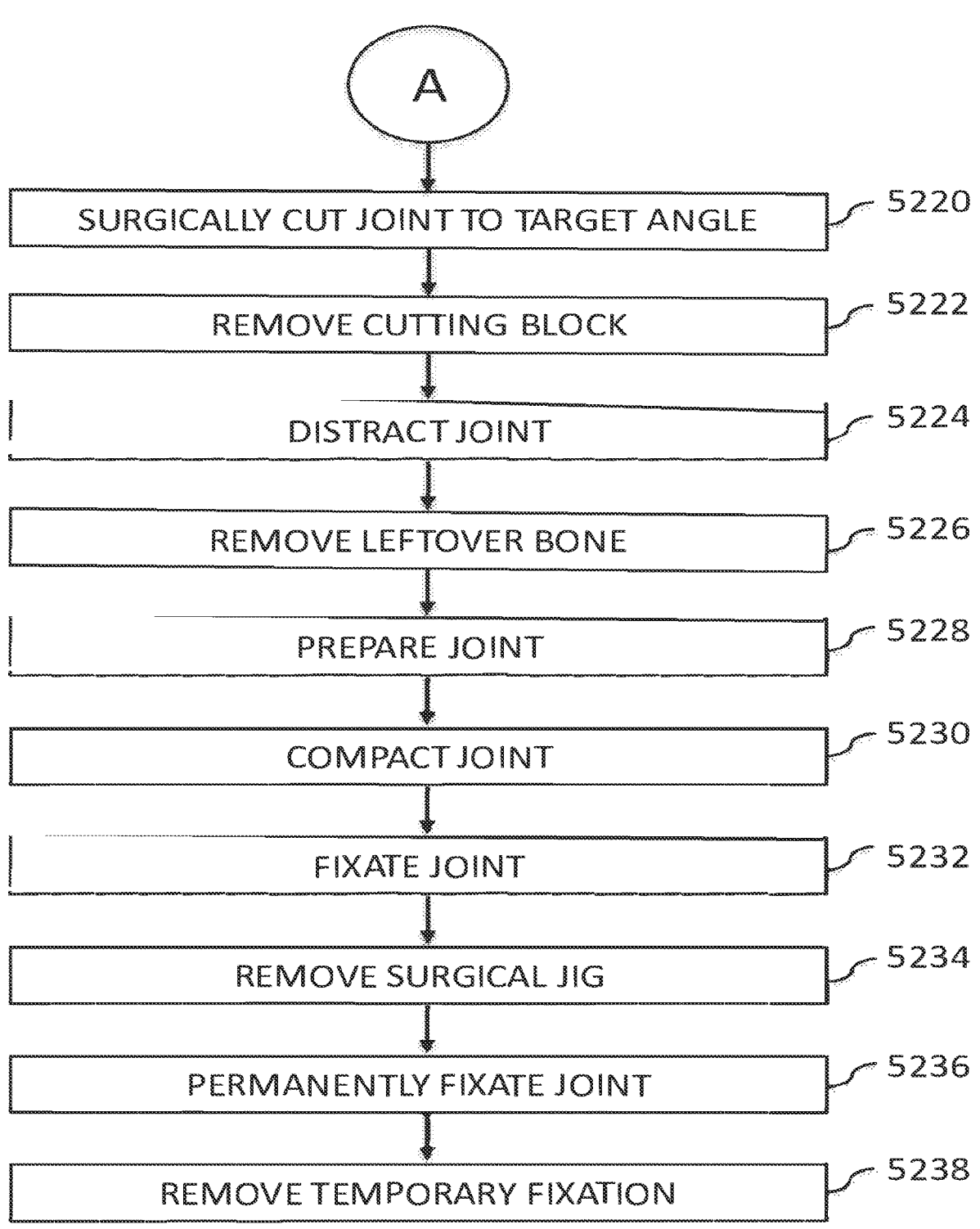

FIG. 52A is a flow diagram illustrating one embodiment of a technique or method 5200A for performing an osteotomy. At least in the illustrated embodiment, method 5200A begins by a medical professional (e.g., a surgeon) attaching a surgical jig 5106 (e.g., any of the surgical jigs 4300 discussed above with reference to FIGS. 43 through 50B) to a patient's cuneiform (block 5202). The surgical jig 5106 can be attached by placing one or more surgical pins through the designated aperture(s) in the attachment body 4302 of the surgical jig 5106.

The surgical jig 5106 is then aligned with the patient's metatarsal (block 5204). Alignment can be achieved by rotating the surgical jig 5106 at the joint between the attachment body 4302 and the arm 4314 until the metatarsal contact 4312 fits around the curvature of the metatarsal. This rotation can then be locked in place by tightening the rail hinge 4310.

Next, the intermetatarsal (IM) angle of the patient's metatarsal is corrected (block 5206). The IM angle of the patient's metatarsal is corrected with respect to the midline of the cuneiform by turning the rail adjustment screw 4318. The patient's metatarsal is then rotated utilizing a wire 4804 placed through the rotation guide 4320 (block 5208).

In some embodiments, the order of blocks 5206 and 5208 are reversed. That is, the patient's metatarsal is rotated utilizing the wire 4804 placed through the rotation guide 4320 (block 5208) and then the IM angle of the patient's metatarsal is corrected (block 5206).

The rotated position of the patient's metatarsal is locked using a surgical pin through the distraction body 4308 (block 5210). The rotation guide 4320 can be removed once the position is locked if more visibility is needed.

A positioning guide 5104 (e.g., positioning guide 4000) is placed into the patient's cuneiform-metatarsal joint (block 5212). A surgical cutting block 5102 (e.g., surgical cutting blocks 100 through 3900) is aligned and placed over the joint with the positioning guide 5104 sliding through the positioning slot 106 (block 5214). The surgical cutting block 5102 is then secured to the bone (block 5216) and the positioning guide 5104 removed (block 5218).

The patient's joint is surgically cut to a target angle (block 5220) and the surgical cutting block 5102 is removed (block 5222). The patient's joint is then distracted (block 5224). Distraction can be achieved by rotating the distraction threads 4306 to move the distraction body 4308 in the distraction direction.

Any leftover bone from the cutting may then be removed (block 5226). The joint is then prepared to surgeons' preference (block 5228).

Next, the patient's joint is compacted (block 5230). Compaction is achieved by rotating the distraction threads 4306 to move the distraction body 4308 in the compaction direction, which is the opposite direction of distraction, until the desired compression is obtained.

The joint is then fixated (block 5232). The joint can be permanently or temporarily fixated in block 5232 and the surgical jig 5106 is then removed (block 5234).

If the joint is temporarily fixated in block 5232, the joint is permanently fixated (block 5236). After the joint is permanently fixated, the temporary fixation can be removed (block 5238).

Figure 52B:
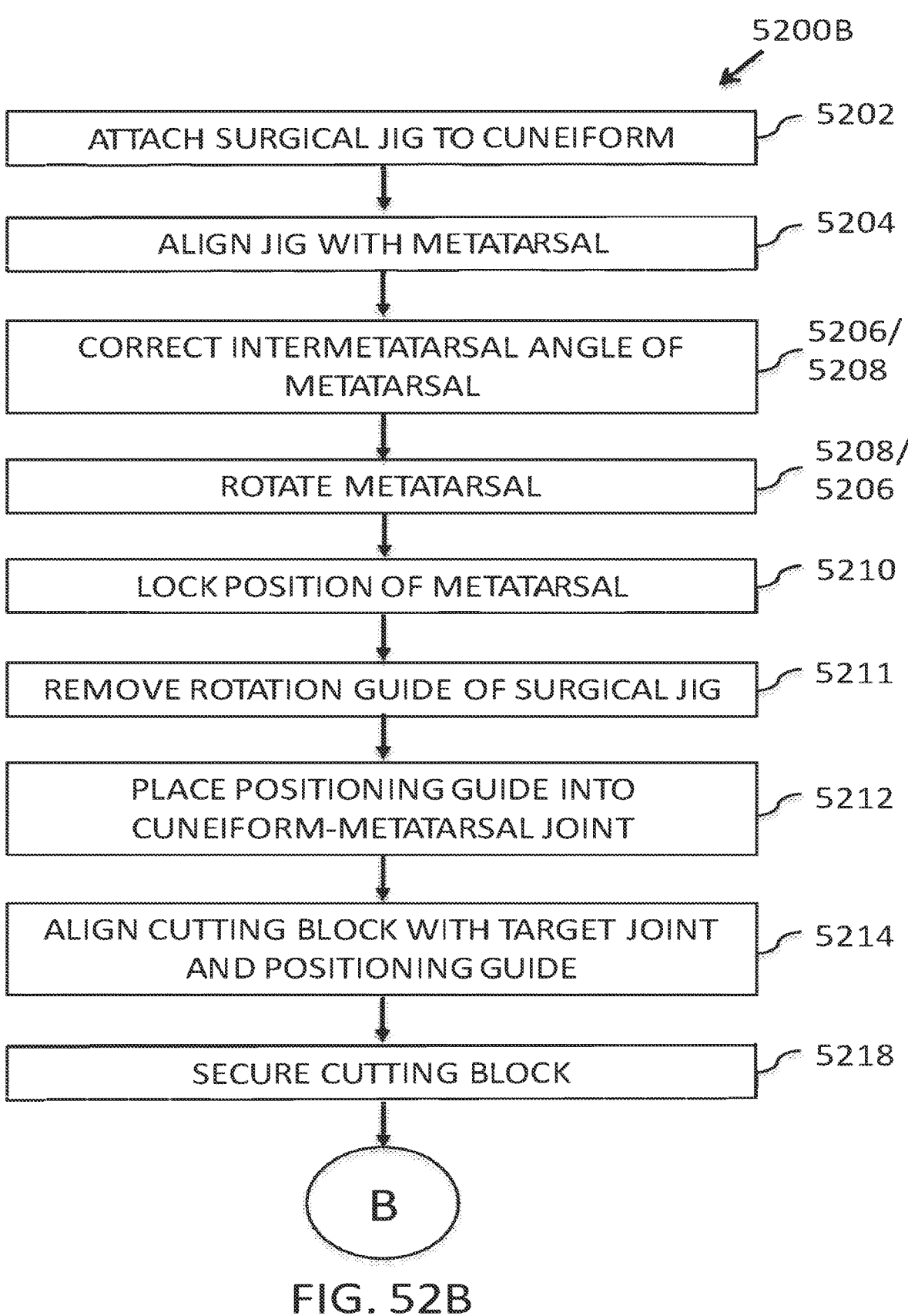
FIG. 52B is a flow diagram illustrating another embodiment of a method for performing an osteotomy.
Figure 52B:
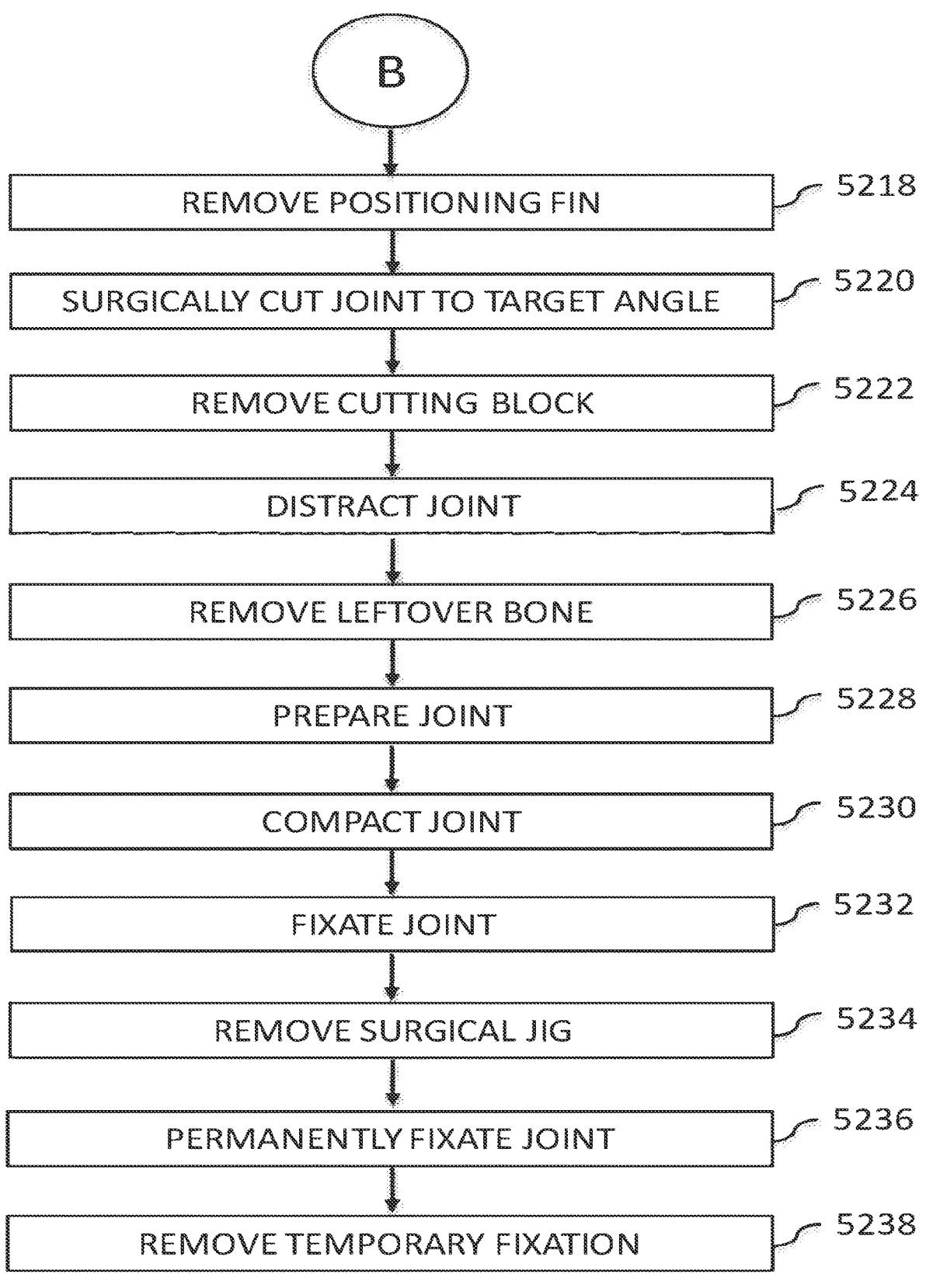

FIG. 52B is a flow diagram illustrating another embodiment of a method 5200B for performing an osteotomy. In various embodiments, method 5200B includes blocks 5202, 5204, 5206/5208, 5208/5206, 5210, 5212, 5214, 5216, 5218, 5220, 5222, 5224, 5226, 5228, 5230, 5232, 5234, 5236, and 5238 similar to the method 5200A discussed above.

In addition, the method 5200B includes removing the rotation guide 4320 once the position of the patient's metatarsal is locked in block 5210 (block 5211). The rotation guide 4320 may be removed if more visibility is needed.

Figure 53A:
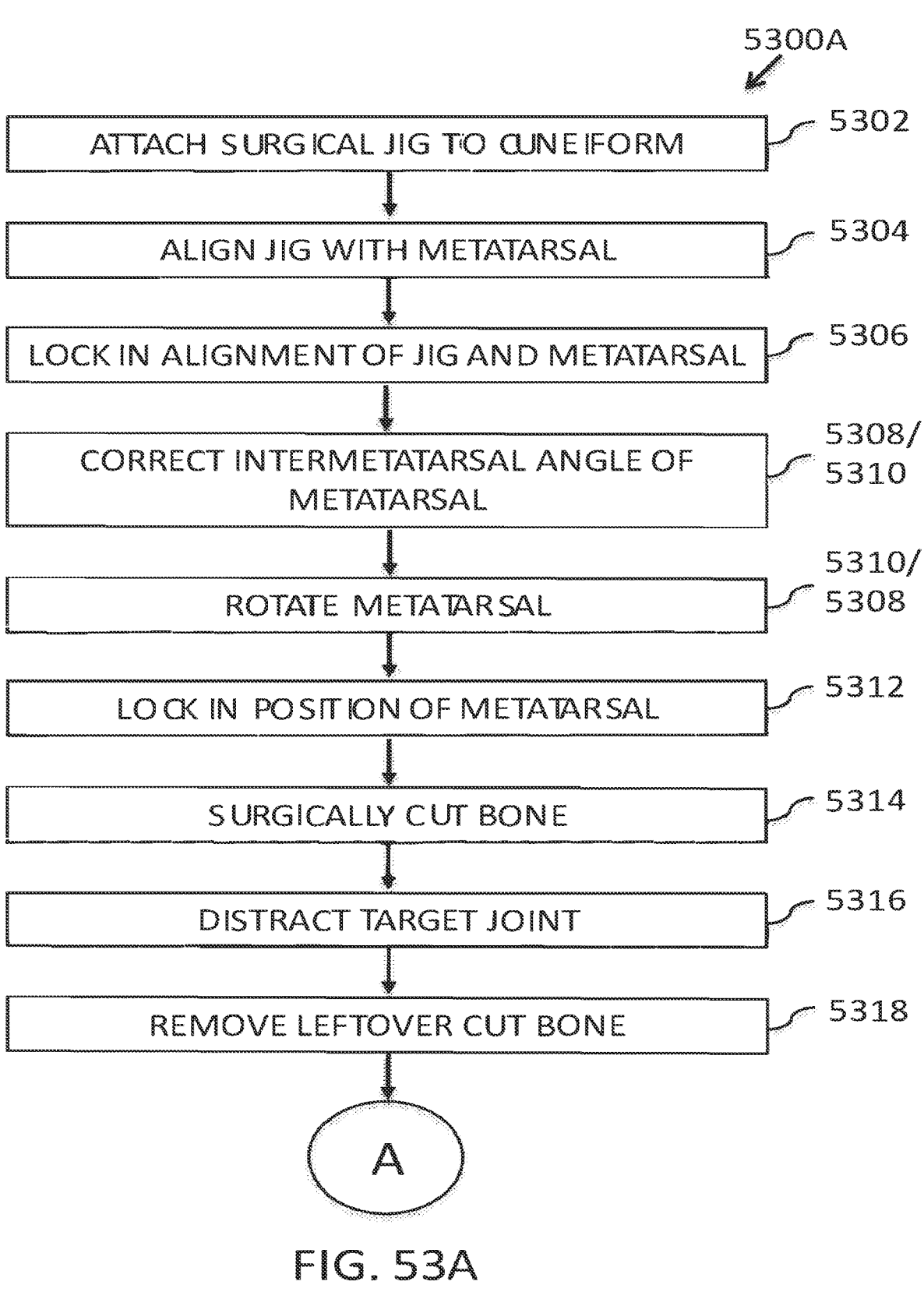
FIG. 53A is a flow diagram illustrating yet another embodiment of a method for performing an osteotomy.
Figure 53A:
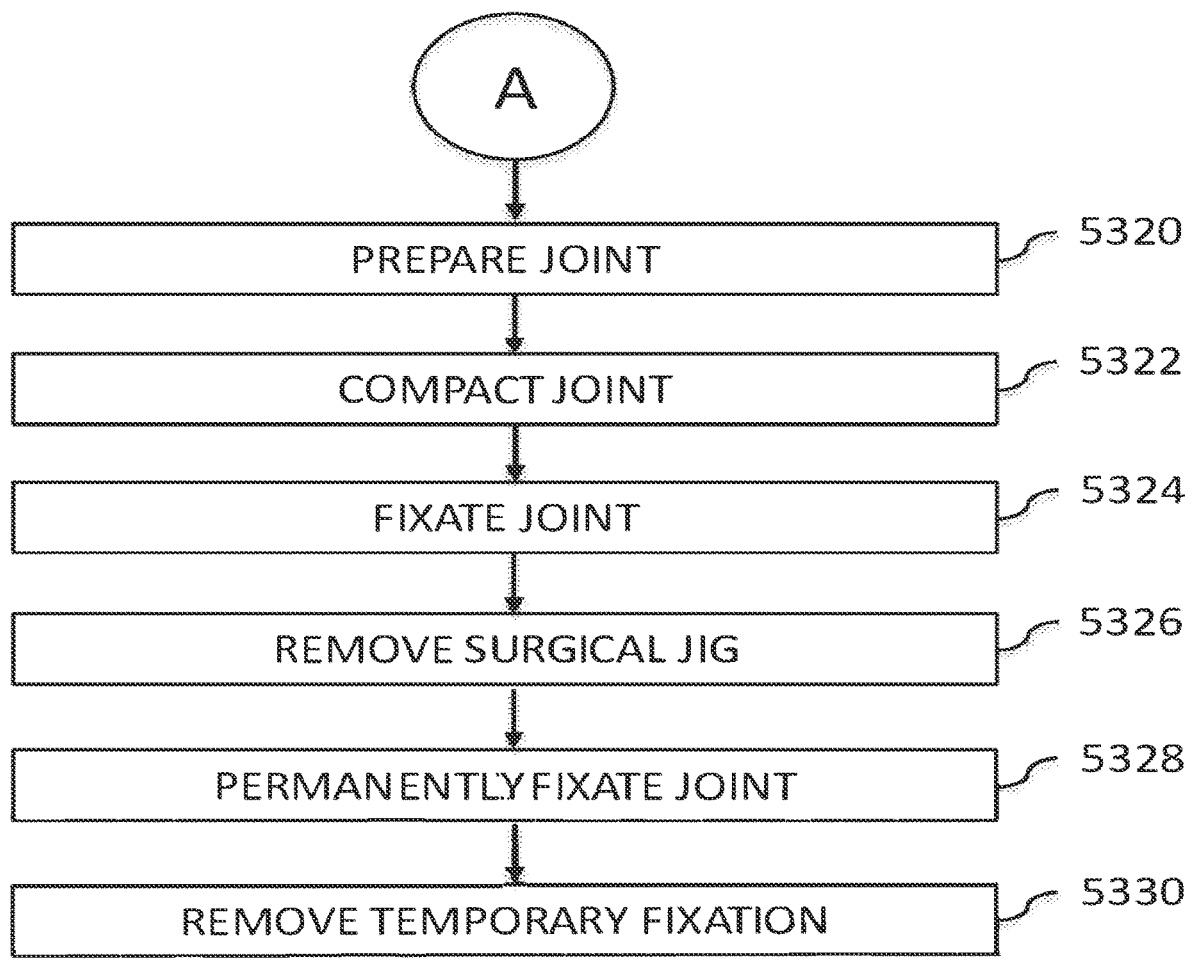
Figure 53B:
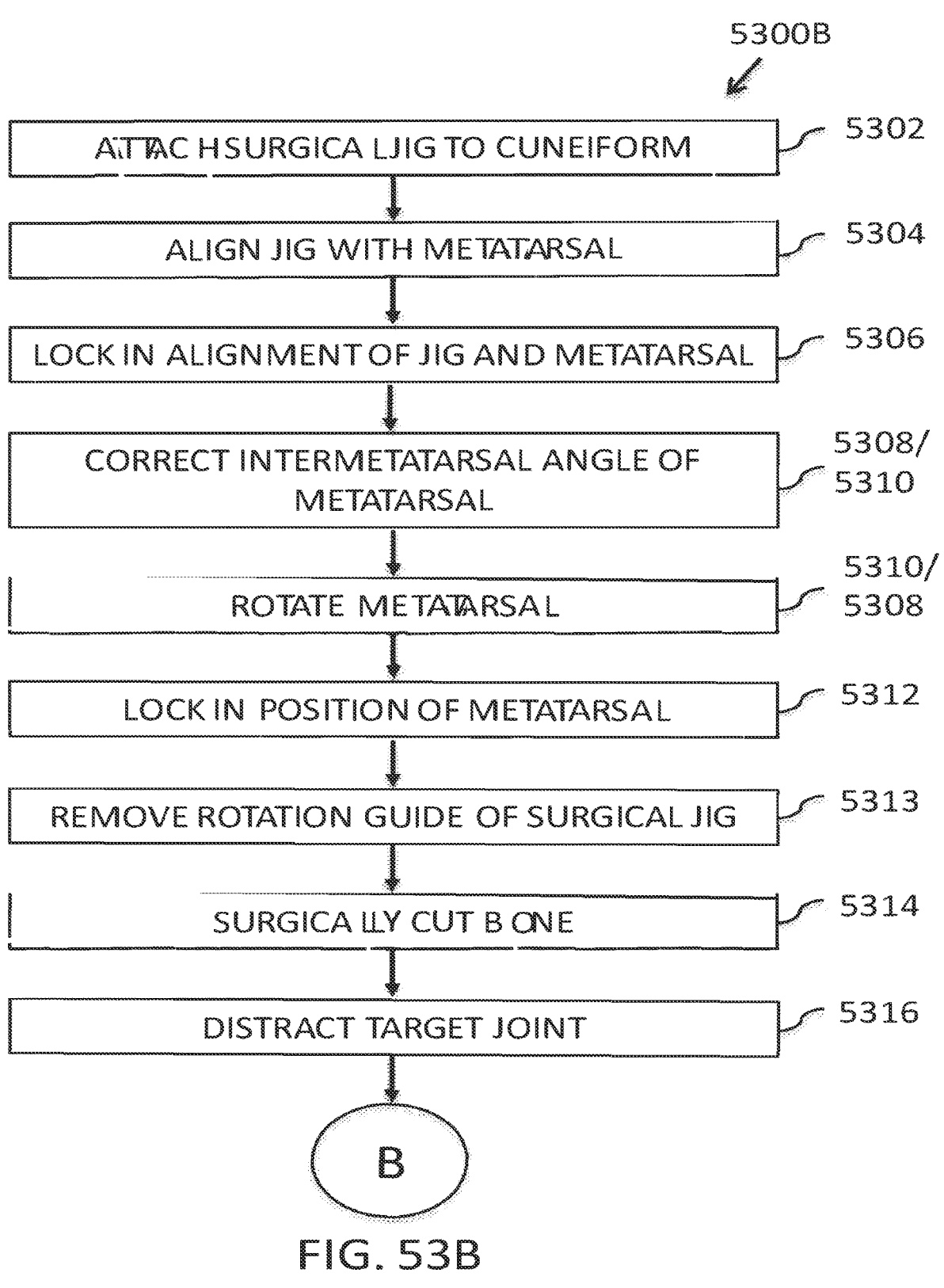
FIG. 53B is a flow diagram illustrating still another embodiment of a method for performing an osteotomy.
Figure 53B:
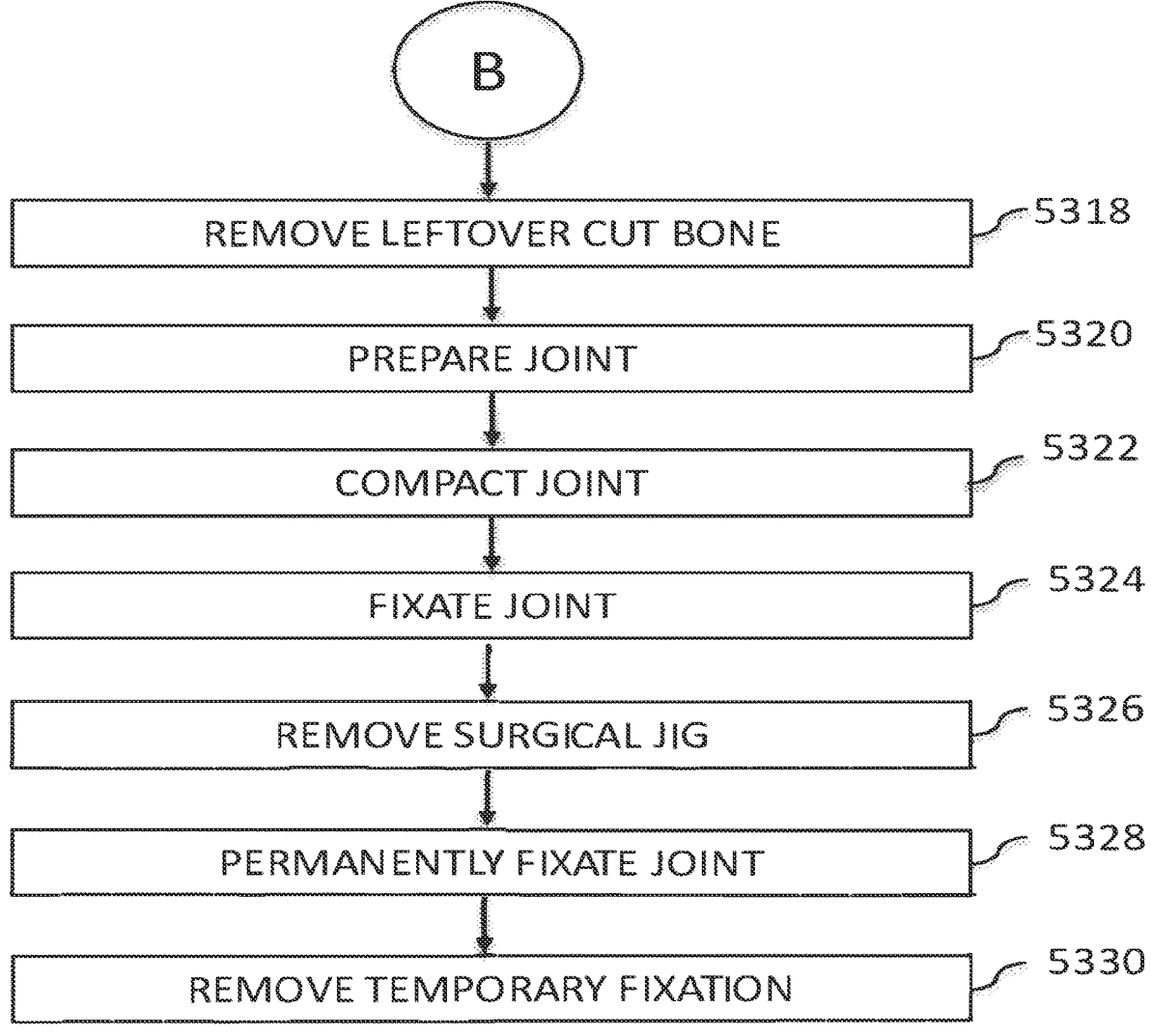

FIG. 53A is a flow diagram illustrating another embodiment of a method 5300A for performing an osteotomy. At least in the illustrated embodiment, method 5300A begins by a medical professional (e.g., a surgeon) attaching a surgical jig 5106 (e.g., any of the surgical jigs 4300 discussed above with reference to FIGS. 43 through 50B) to a patient's cuneiform (block 5302). The surgical jig 5106 can be attached by placing one or more surgical pins through the designated aperture(s) in the attachment body 4302 of the surgical jig 5106.

The surgical jig 5106 is then aligned with the patient's metatarsal (block 5304) and the alignment is locked in place (block 5306). Alignment can be achieved by rotating the surgical jig 5106 at the joint between the attachment body 4302 and the arm 4314 until the metatarsal contact 4312 fits around the curvature of the metatarsal. This rotation can then be locked in place by tightening the rail hinge 4310.

Next, the intermetatarsal (IM) angle of the patient's metatarsal is corrected (block 5308). The IM angle of the patient's metatarsal is corrected with respect to the midline of the cuneiform by turning the rail adjustment screw 4318. The patient's metatarsal is rotated utilizing a wire 4804 placed through the rotation guide 4320 (block 5310).

In some embodiments, the order of blocks 5308 and 5310 are reversed. That is, the patient's metatarsal is rotated utilizing the wire 4804 placed through the rotation guide 4320 (block 5310) and then the IM angle of the patient's metatarsal is corrected (block 5308).

The rotated position of the patient's metatarsal is locked using a surgical pin through the distraction body 4308 (block 5312). The rotation guide 4320 can be removed once the position is locked if more visibility is needed.

The medical professional can then surgically cut the bone (block 5314). The bone can be surgically cut using a surgical instrument (e.g., a cutting guide) and/or done free handedly.

The patient's joint is then distracted (block 5316). Distraction can be achieved by rotating the distraction threads 4306 to move the distraction body 4308 in the distraction direction.

Any leftover bone from the cutting may then be removed (block 5318). The joint is then prepared to surgeons' preference (block 5320).

Next, the patient's joint is compacted (block 5322). Compaction is achieved by rotating the distraction threads 4306 to move the distraction body 4308 in the compaction direction, which is the opposite direction of distraction, until the desired compression is obtained.

The joint is then fixated (block 5324). The joint can be permanently or temporarily fixated in block 5324 and the surgical jig 5106 is then removed (block 5326).

If the joint is temporarily fixated in block 5324, the joint is permanently fixated (block 5328). After the joint is permanently fixated, the temporary fixation can be removed (block 5330).

FIG. 52B is a flow diagram illustrating another embodiment of a method 5200B for performing an osteotomy. In various embodiments, method 5200B includes blocks 5302, 5304, 5306, 5308/5310, 5310/5308, 5312, 5314, 5316, 5318, 5320, 5322, 5324, 5326, 5328, and 5330 similar to the method 5300A discussed above.

In addition, the method 5300B includes removing the rotation guide 4320 once the position of the patient's metatarsal is locked in block 5312 (block 5313). The rotation guide 4320 may be removed if more visibility is needed.

Figure 54A:
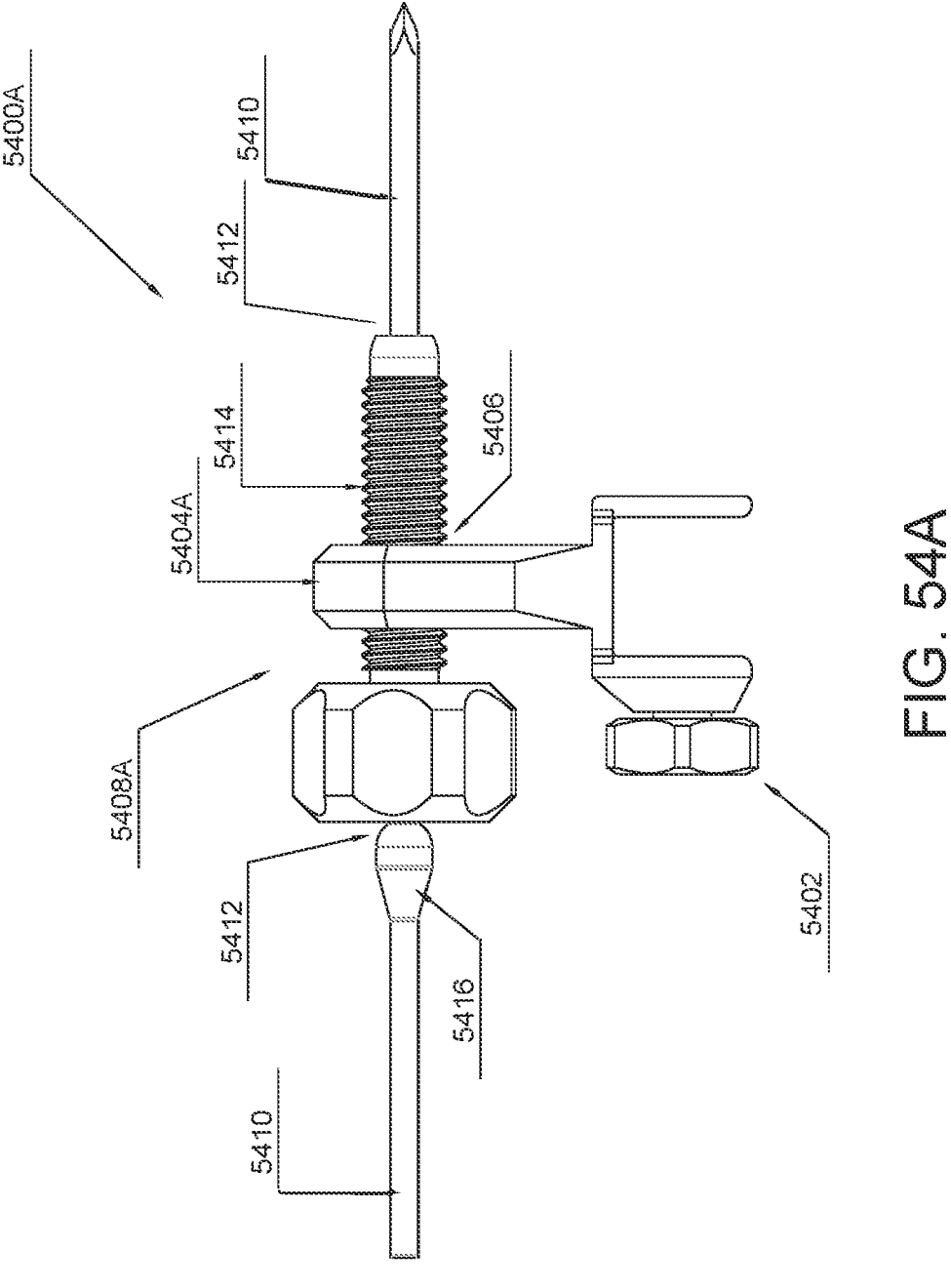
FIGS. 54A through 54C are diagrams illustrating various embodiments of a positioning device.

FIG. 54A is a diagram of one embodiment of a positioning device 5400A (or positioner 5400A). The positioning device 5400A, in some embodiments, is an independent device that is capable of being attached and detached (e.g., is detachably coupleable) to a surgical device and/or instrument (e.g., surgical jig 4300). In additional or alternative embodiments, the positioning device 5400A is fixed, coupled to, and/or forms at least a portion of a surgical jig 4300.

The positioning device 5400A and/or each portion of the positioning device 5400A may be formed of any suitable material and/or combination of materials that is/are known or developed in the future. In certain embodiments, the material(s) included in and/or forming the positioning device 5400A and/or portion(s) thereof is/are sterilizable.

At least in the embodiment illustrated in FIG. 54A, the positioning device 5400A includes, among other features, elements, and/or components, a securing device 5402, a body 5404A, and a tuner 5408A that is/are configured to be operable with one or more fixation devices 5410.

A securing device 5402 may include any suitable device/apparatus/system and/or component(s) capable of fixedly and/or detachably coupling the positioning device 5400A to a surgical jig 4300. At least in the illustrated embodiment, the securing device 5402 includes a clamp (e.g., a C-clamp, etc.), which can include a knob for tightening/loosening the clamp.

While the securing device 5402 is shown as including a C-clamp, the various embodiments are not limited to a C-clamp. That is, various other embodiments can include other securing mechanisms and/or types of securing mechanisms (e.g., a spring clamp, bench clamp, G-clamp, strap clamp, pipe clamp, wire rope clamp, action clamp, locking clamp, hose clamp, screw clamp, hand screw clamp, and a fastener, etc., among other device/apparatus/system and/or component(s) capable or coupling the positioning device 5400A to a surgical jig 4300 that are possible and contemplated herein).

A body 5404A may include any suitable structure (e.g., size, shape, and/or dimension(s) that is/are known or developed in the future capable of performing the functions discussed herein. In various embodiments, the body 5404A (or housing) may include an inner wall defining a boundary of an aperture 5406 configured to house the tuner 5408A.

In various embodiments, the inner wall of the body 5404A includes a set of grooves. As such, the grooved inner wall of the body 5404A and aperture 5406 are suitable for housing a threaded tuner 5408A, as discussed elsewhere herein. Further, the grooved inner wall of the body 5404A and aperture 5406 are configured to suitably enable/allow a threaded tuner 5408A to rotate clockwise and counterclockwise therewith (e.g., screw in and screw out), as further discussed elsewhere herein.

A tuner 5408A may include any suitable device, apparatus, and/or structure capable of at least temporarily housing one or more fixation devices 5410. Further, a tuner 5408A may include any suitable device, apparatus, and/or structure that can enable and/or facilitate enabling the fixation device 5410 to connect and/or couple to a bone of a subject. In various embodiments, the tuner 5408A comprises a rotational actuator.

In various embodiments, the tuner 5408A includes an aperture 5412 and/or includes a hollow portion 5412 for at least temporarily housing one or more fixation devices 5410. In various embodiments, the aperture/hollow portion 5412 is configured to enable/allow the fixation device(s) 5410 to be inserted in and removed from the tuner 5408A.

In some embodiments, the tuner 5408A includes a locking mechanism to lock and/or hold the fixation device(s) 5410 in place in the aperture/hollow portion 5412 after insertion and during use. In further embodiments, the tuner 5408A includes a releasing mechanism to release and/or unlock the fixation device(s) 5410 so that the fixation device(s) 5410 can be removed from the aperture/hollow portion 5412 after use.

In additional or alternative embodiments, the tuner 5408A is threaded and/or includes a threaded portion 5414 to define a threaded tuner. The threads of the tuner 5408A function in cooperation/conjunction with the threaded inner wall of the body 5404A to enable/allow the tuner 5408A to tune and/or adjust the depth of the fixation device 5410 inserted in the bone of a subject and/or to adjust and/or facilitate adjusting the position and/or location of the bone within which the fixation device 5410 is inserted.

For example, the tuner 5408A can be rotated clockwise (or counterclockwise) so that the threads of the tuner 5408A interact with the grooves in the inner wall of the body 5404A to insert (e.g., screw, push, etc.) the fixation device 5410 into the bone and/or to move the bone laterally. In other words, the tuner 5408A can apply a force on the fixation device 5410 in a positive direction (e.g., a positive force) to insert the fixation device 5410 into a bone (e.g., a metatarsal and/or the first metatarsal) and/or to move the bone laterally and/or along a transverse plan. In some embodiments, the bone is a first metatarsal, and the positive direction is a direction toward another bone (e.g., a metatarsal and/or the second metatarsal) along the transverse plane. In this manner, space between the first and second metatarsals can be reduced and/or eliminated.

Additionally, the tuner 5408A can be rotated counterclockwise (or clockwise) so that the threads of the tuner 5408A interact with the grooves in the inner wall of the body 5404A to remove (e.g., unscrew, pull, etc.) the fixation device 5410 from the bone and/or to move the bone laterally in the opposite direction. In other words, the tuner 5408A can apply a force on the fixation device 5410 in a negative direction (e.g., a negative force) to remove the fixation device 5410 from a bone (e.g., a metatarsal and/or the first metatarsal) and/or to move the bone laterally and/or along a transverse plan. In some embodiments, the bone is a first metatarsal, and the negative direction is a direction away from another bone (e.g., a metatarsal and/or the second metatarsal) along the transverse plane. In this manner, space can be created between the first and second metatarsals and/or the space between the first and second metatarsals can be increased.

The tuner 5408A can be rotated using any suitable device, mechanism, and/or structure that is known or developed in the future. At least in the illustrated embodiment, the tuner 5408A includes a knob, among other devices, mechanisms, and/or structures that are possible, each or which is contemplated herein.

A fixation device 5410 may include any device, apparatus, and/or structure that is capable of performing the functions of a fixation device 5410 discussed herein. As such, a fixation device 5410 may include any suitable fixation device that is known or developed in the future. In various embodiments, a fixation device 5410 is configured for insertion into and removal from a bone (e.g., a metatarsal and/or the first metatarsal, etc.) and for moving the bone from a first position to a second position, which can include from an original position to a new or corrected position.

In some embodiments, the fixation device 5410 includes an olive wire. The olive wire can include an olive or stopper 5416 configured to function as a guide and/or depth gauge when the olive wire is inserted into a bone.

The fixation device 5410, in other embodiments, includes a Kirschner wire or K-wire. In other embodiments, the fixation device 5410 includes a screw, a pin, and/or a nail, etc., among other similar devices, apparatus, and/or structures that are possible, each of which is contemplated herein.

Figures 55A, 55B:
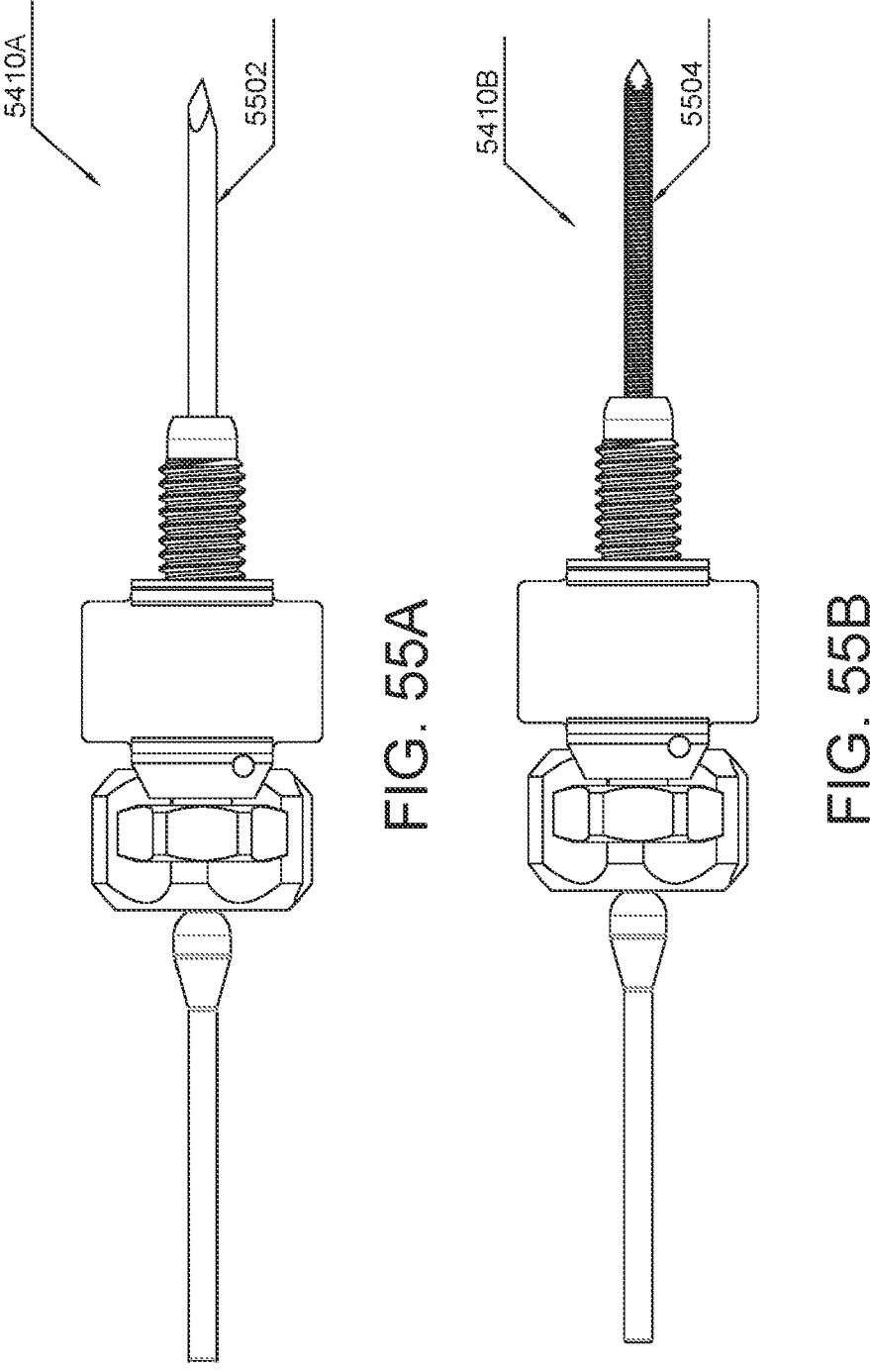
FIGS. 55A and 55B are diagrams illustrating various embodiments of a fixation device for use with the positioning devices of FIGS. 54A through 54C.

With reference to FIG. 55A, in some embodiments, a fixation device 5410A includes an insertion portion 5502 that includes a smooth, substantially smooth, and/or non-threaded surface. In various embodiments, the insertion portion 5502 defines a smooth, substantially smooth, and/or non-threaded insertion portion.

Referring to FIG. 55B, in some embodiments, a fixation device 5410B includes an insertion portion 5504 that includes a threaded surface. In various embodiments, the insertion portion 5504 defines a threaded insertion portion.

Figure 54B:
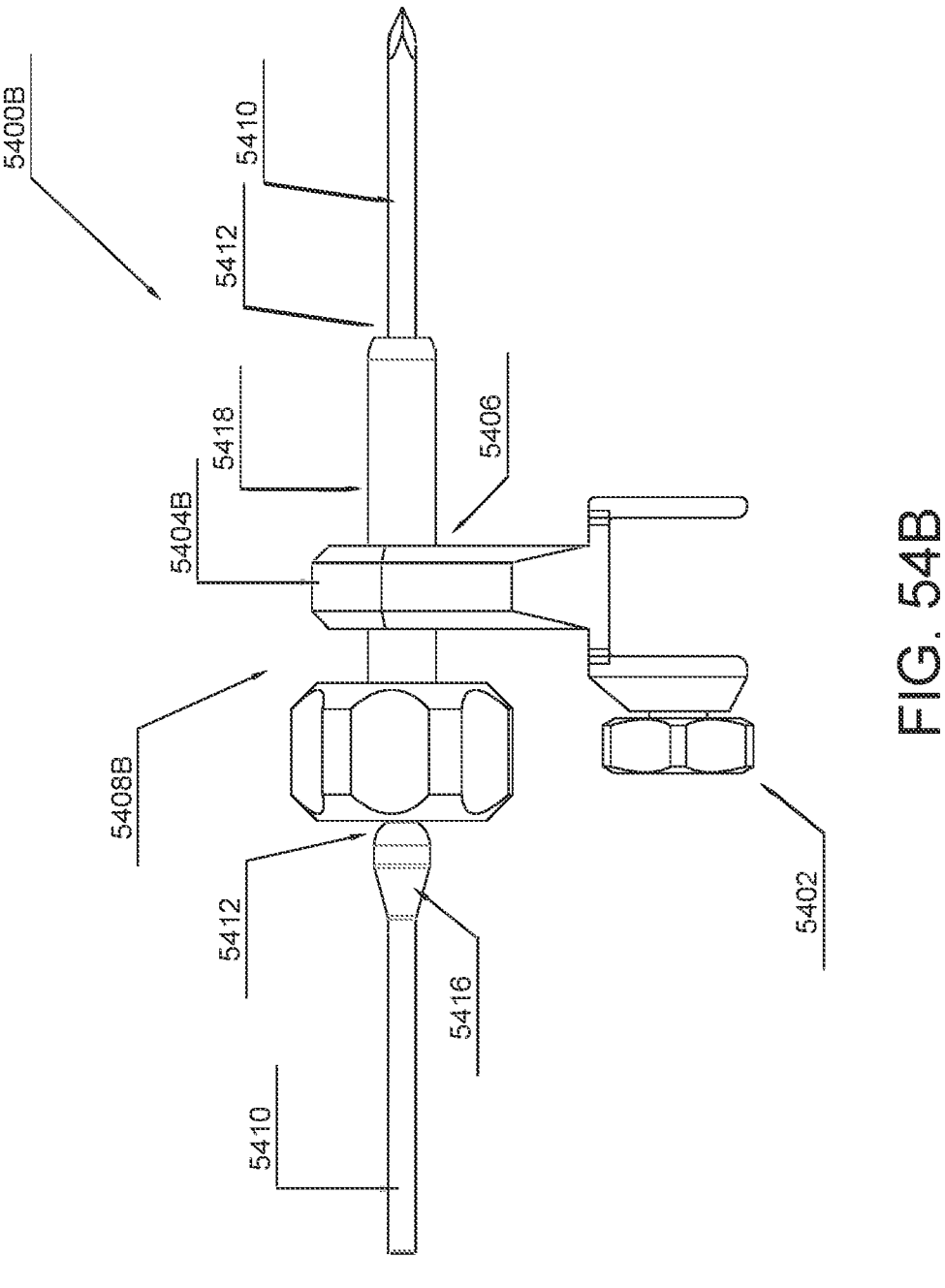

FIG. 54B is a diagram of another embodiment of a positioning device 5400B (or positioner 5400B). The positioning device 5400B, in some embodiments, is an independent device that is capable of being attached and detached (e.g., is detachably coupleable) to a surgical device and/or instrument (e.g., surgical jig 4300). In additional or alternative embodiments, the positioning device 5400B is fixed, coupled to, and/or forms at least a portion of a surgical jig 4300.

The positioning device 5400B and/or each portion of the positioning device 5400B may be formed of any suitable material and/or combination of materials that is/are known or developed in the future. In certain embodiments, the material(s) included in and/or forming the positioning device 5400B and/or portion(s) thereof is/are sterilizable.

The positioning device 5400B includes a securing device 5402 similar to the securing device 5402 discussed with reference to the positioning device 5400A. At least in the embodiment illustrated in FIG. 54B, the positioning device 5400B further includes, among other features, elements, and/or components, a body 5404B and a tuner 5408B that is/are configured to be operable with one or more fixation devices 5410, which fixation device(s) 5410 can each be similar to the fixation device(s) 5410 discussed with reference to the positioning device 5400A.

A body 5404B may include any suitable structure (e.g., size, shape, and/or dimension(s) that is/are known or developed in the future capable of performing the functions discussed herein. In various embodiments, the body 5404B (or housing) may include an inner wall defining a boundary of an aperture 5406 configured to house the tuner 5408B.

In various embodiments, the inner wall of the body 5404B is smooth, substantially smooth, or at least does not include a set of grooves. As such, the inner wall of the body 5404B and aperture 5406 are suitable for housing a smooth, substantially smooth, and/or non-threaded tuner 5408B, as discussed elsewhere herein. Further, the inner wall of the body 5404A and aperture 5406 are configured to suitably enable/allow a tuner 5408B to slide therein (e.g., slide in and slide out), as further discussed elsewhere herein.

A tuner 5408B may include any suitable device, apparatus, and/or structure capable of at least temporarily housing one or more fixation devices 5410. Further, a tuner 5408B may include any suitable device, apparatus, and/or structure that can enable and/or facilitate enabling the fixation device 5410 to connect and/or couple to a bone of a subject. In various embodiments, the tuner 5408B comprises a sliding actuator.

In various embodiments, the tuner 5408B includes an aperture 5412 and/or includes a hollow portion 5412 for at least temporarily housing one or more fixation devices 5410. In various embodiments, the aperture/hollow portion 5412 is configured to enable/allow the fixation device(s) 5410 to be inserted in and removed from the tuner 5408B.

In some embodiments, the tuner 5408B includes a locking mechanism to lock and/or hold the fixation device(s) 5410 in place in the aperture/hollow portion 5412 after insertion and during use. In further embodiments, the tuner 5408B includes a releasing mechanism to release and/or unlock the fixation device(s) 5410 so that the fixation device(s) 5410 can be removed from the aperture/hollow portion 5412 after use.

In additional or alternative embodiments, the tuner 5408B is smooth, substantially smooth, and/or non-threaded and/or includes a smooth, substantially smooth, and/or non-threaded portion 5418 to define a non-threaded tuner. The tuner 5408B functions in cooperation/conjunction with the inner wall of the body 5404B to enable/allow the tuner 5408B to tune and/or adjust the depth of the fixation device 5410 inserted in the bone of a subject and/or to adjust and/or facilitate adjusting the position and/or location of the bone within which the fixation device 5410 is inserted.

For example, the tuner 5408B can be slid laterally (e.g., pushed, etc.) to insert the fixation device 5410 into the bone and/or to move the bone laterally. In other words, the tuner 5408B can apply a force on the fixation device 5410 in a positive direction (e.g., a positive force) to insert the fixation device 5410 into a bone (e.g., a metatarsal and/or the first metatarsal) and/or to move the bone laterally and/or along a transverse plan. In some embodiments, the bone is a first metatarsal, and the positive direction is a direction toward another bone (e.g., a metatarsal and/or the second metatarsal) along the transverse plane. In this manner, space between the first and second metatarsals can be reduced and/or eliminated.

Additionally, the tuner 5408B can be slide laterally (e.g., pulled, etc.) to remove the fixation device 5410 from the bone and/or to move the bone laterally in the opposite direction. In other words, the tuner 5408B can apply a force on the fixation device 5410 in a negative direction (e.g., a negative force) to remove the fixation device 5410 from a bone (e.g., a metatarsal and/or the first metatarsal) and/or to move the bone laterally and/or along a transverse plan. In some embodiments, the bone is a first metatarsal, and the negative direction is a direction away from another bone (e.g., a metatarsal and/or the second metatarsal) along the transverse plane. In this manner, space can be created between the first and second metatarsals and/or the space between the first and second metatarsals can be increased.

The tuner 5408B can be pushed/pulled or slid using any suitable device, mechanism, and/or structure that is known or developed in the future. At least in the illustrated embodiment, the tuner 5408B includes a knob, among other devices, mechanisms, and/or structures that are possible, each or which is contemplated herein.

Figure 54C:
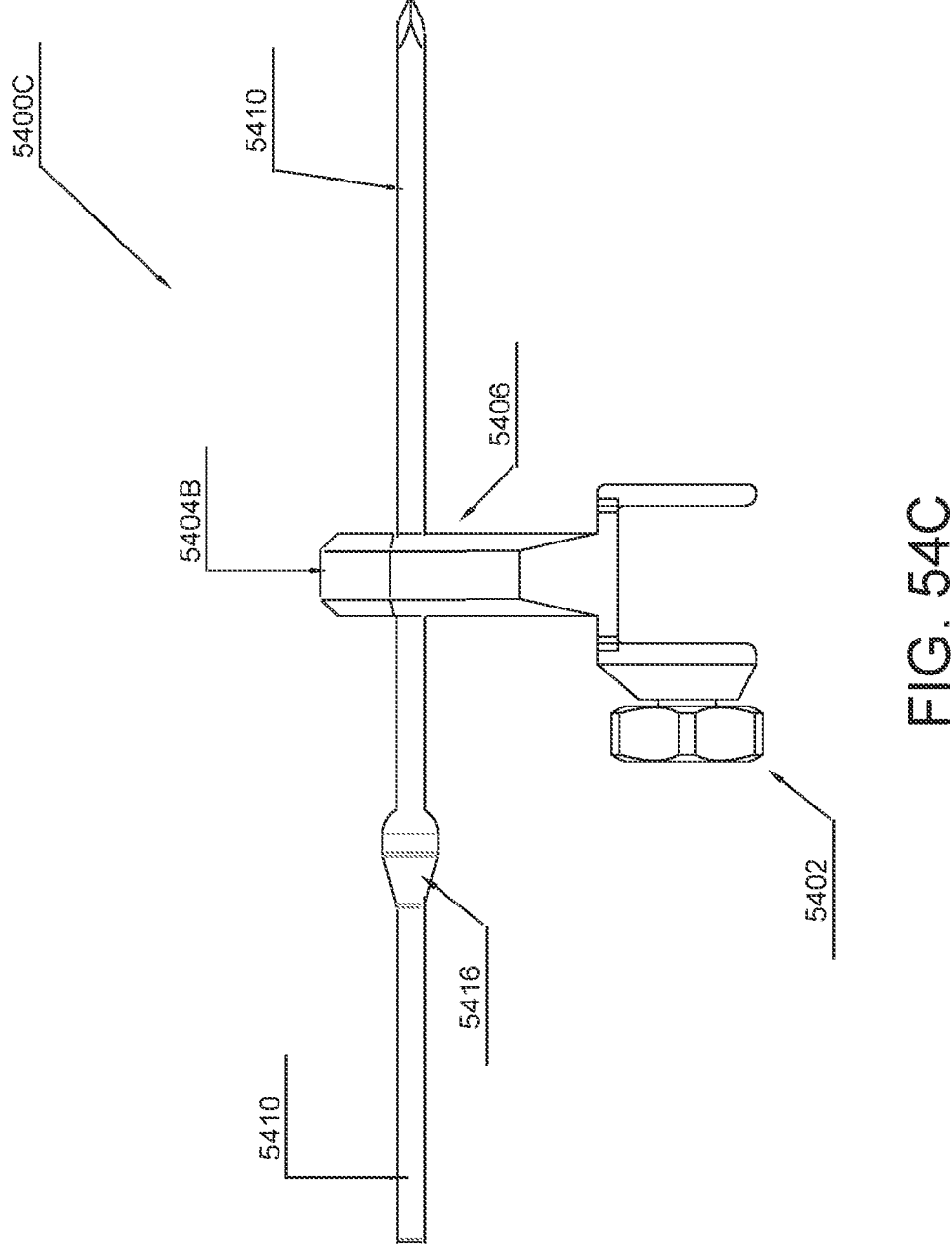

FIG. 54C is a diagram of another embodiment of a positioning device 5400C (or positioner 5400C). The positioning device 5400C, in some embodiments, is an independent device that is capable of being attached and detached (e.g., is detachably coupleable) to a surgical device and/or instrument (e.g., surgical jig 4300). In additional or alternative embodiments, the positioning device 5400C is fixed, coupled to, and/or forms at least a portion of a surgical jig 4300.

The positioning device 5400C and/or each portion of the positioning device 5400C may be formed of any suitable material and/or combination of materials that is/are known or developed in the future. In certain embodiments, the material(s) included in and/or forming the positioning device 5400C and/or portion(s) thereof is/are sterilizable.

The positioning device 5400C includes a securing device 5402 and a body 5404B similar to the securing device 5402 and the body 5404B discussed with reference to the positioning device 5400B. Similar to the embodiments discussed above, the securing device 5402 and the body 5404B is/are configured to be operable with one or more fixation devices 5410, which fixation device(s) 5410 can each be similar to the fixation device(s) 5410 discussed elsewhere herein.

In various embodiments, the inner wall of the body 5404B is configured to enable/allow insertion of the fixation device 5410 into the bone of a subject. Further, the inner wall of the body 5404B is configured to enable/allow adjustment and/or facilitate adjustment of the position and/or location of the bone within which the fixation device 5410 is inserted.

For example, the fixation device 5410 can be slid laterally (e.g., pushed, etc.) to insert the fixation device 5410 into the bone and/or to move the bone laterally. In other words, a force can be applied to the fixation device 5410 in a positive direction (e.g., a positive force) to insert the fixation device 5410 into a bone (e.g., a metatarsal and/or the first metatarsal) and/or to move the bone laterally and/or along a transverse plan. In some embodiments, the bone is a first metatarsal, and the positive direction is a direction toward another bone (e.g., a metatarsal and/or the second metatarsal) along the transverse plane. In this manner, space between the first and second metatarsals can be reduced and/or eliminated.

Additionally, the fixation device can be slid laterally (e.g., pulled, etc.) to remove the fixation device 5410 from the bone and/or to move the bone laterally in the opposite direction. In other words, a force can be applied to the fixation device 5410 in a negative direction (e.g., a negative force) to remove the fixation device 5410 from a bone (e.g., a metatarsal and/or the first metatarsal) and/or to move the bone laterally and/or along a transverse plan. In some embodiments, the bone is a first metatarsal, and the negative direction is a direction away from another bone (e.g., a metatarsal and/or the second metatarsal) along the transverse plane. In this manner, space can be created between the first and second metatarsals and/or the space between the first and second metatarsals can be increased.

While the various embodiments of the positioning devices 5400A, 5400B, and 5400C show the positioning devices 5400A, 5400B, and 5400C being used with a fixation device 5410A, the various embodiments are not limited to such. That is, various other embodiments can use a fixation device 5410B with the positioning devices 5400A, 5400B, and 5400C.

Figure 56:
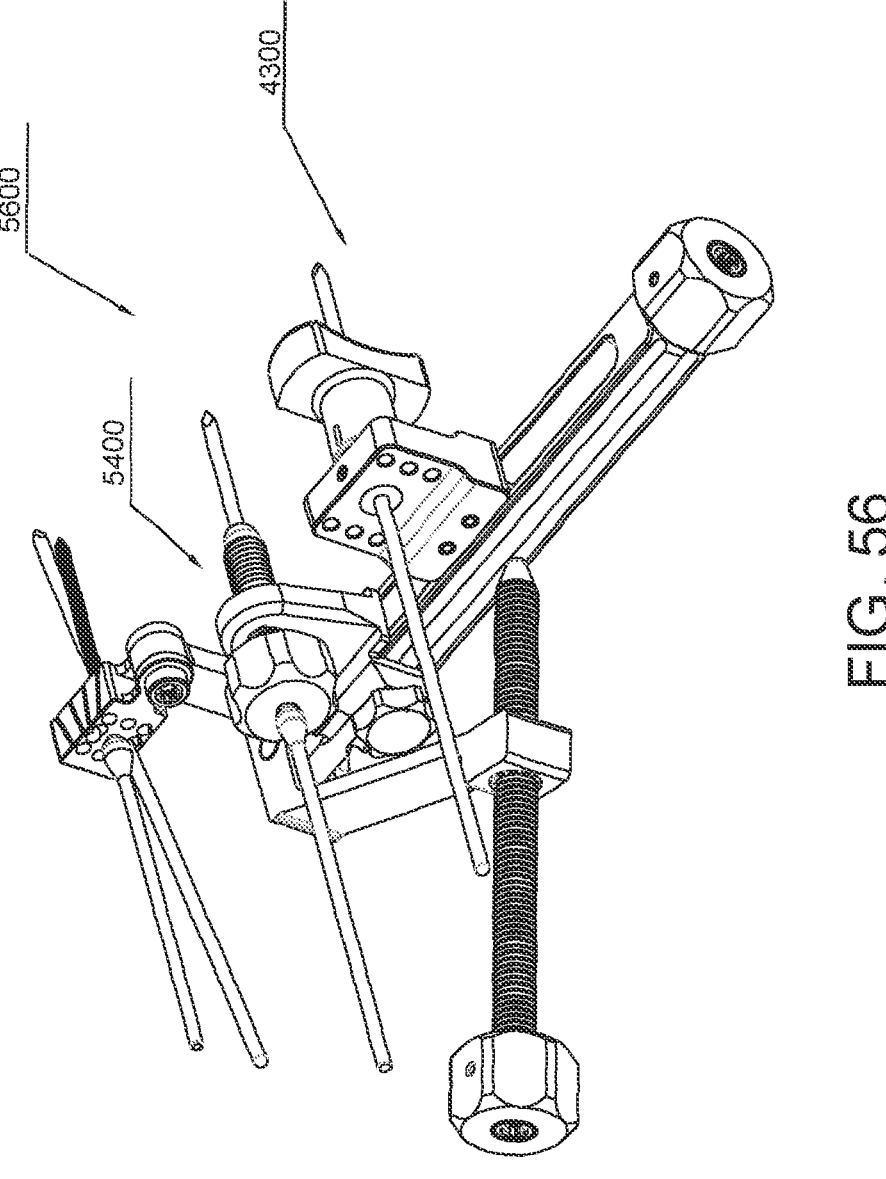
FIG. 56 is a diagram illustrating one embodiment of a surgical system including the surgical jig of FIG. 43 and a positioning device of FIGS. 54A through 54C.

FIG. 56 is a diagram illustrating one embodiment of a surgical system 5600 for use in performing an osteotomy. In certain embodiments, the osteotomy can include a procedure to correct a bunion.

At least in the illustrated embodiment, the surgical system 5600 includes, among other features, components, and/or elements, a surgical jig 4300 and a positioning device 5400. The surgical jig 4300 may include any embodiment of the surgical jig discussed herein.

In various embodiments, the positioning device 5400 can include the positioning device 5400A, the positioning device 5400B, or the positioning device 5400C. That is, while FIG. 56 shows the surgical system 5600 as including the positioning device 5400A, other embodiments can include the positioning device 5400B or the positioning device 5400C.

In some embodiments, the positioning device 5400 is detachably/releasably coupleable with the surgical jig 4300. In other embodiments, the positioning device 5400 is fixedly coupled to and/or forms at least a portion of the surgical jig 4300.

Figures 57A, 57B:
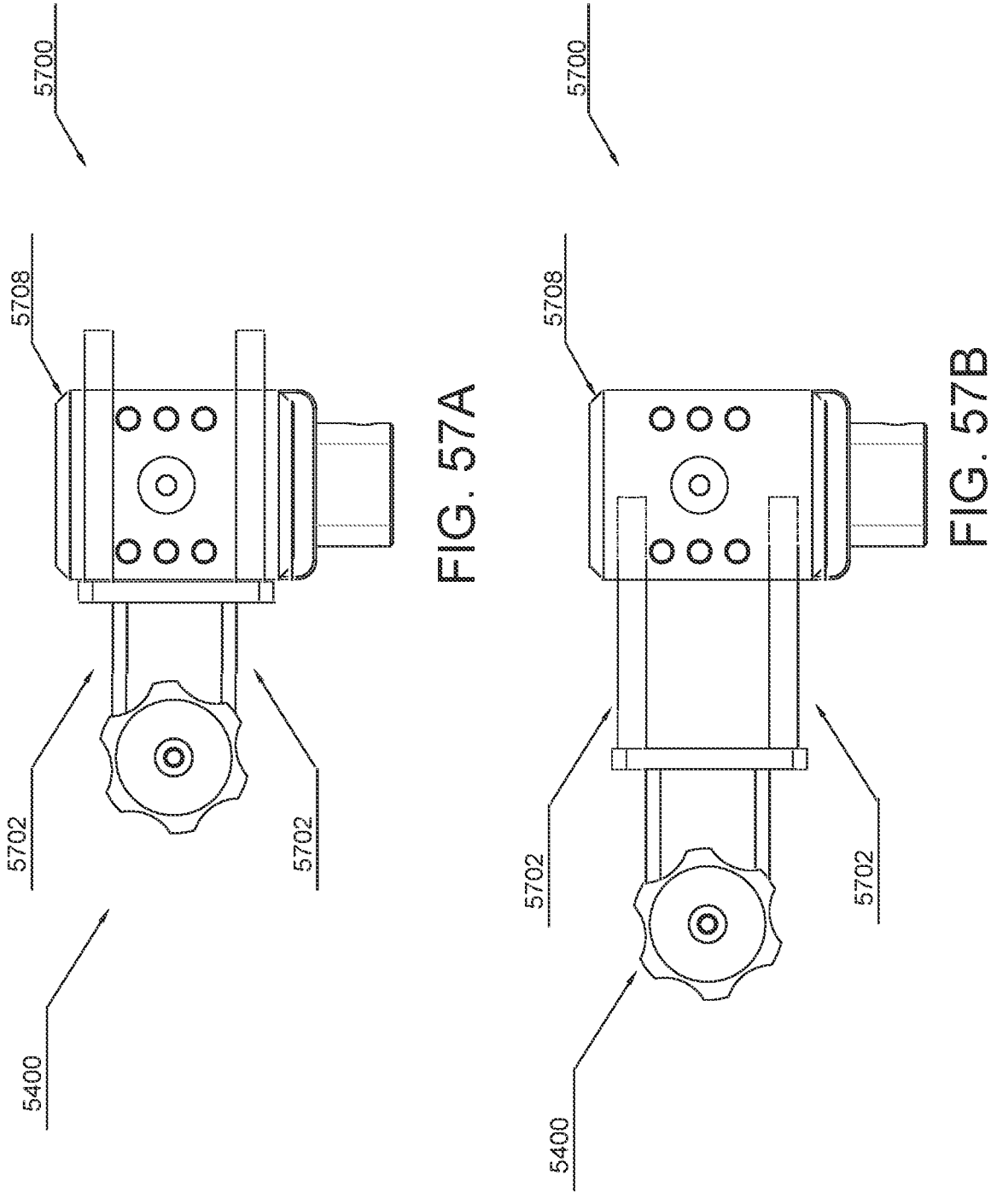
FIGS. 57A and 57B are diagrams illustrating embodiments of a moveable positioning device that includes one of the positioning devices of FIGS. 54A through 54C.

FIGS. 57A and 57B are diagrams illustrating another embodiment of a positioning device 5700 for use in performing an osteotomy. In certain embodiments, the osteotomy can include a procedure to correct a bunion.

At least in the illustrated embodiment, the positioning device 5700 includes, among other elements and/or features, a positioning device 5400, a set of one or more connectors 5702, a distraction body 5708. The positioning device 5400 may include any embodiment of positioning device 5400A, positioning device 5400B, and/or positioning device 5400C discussed elsewhere herein. In addition, the distraction body 5708 may include any embodiment of a distraction body 4308 discussed elsewhere herein.

A connector 5702 may include and/or be formed of any suitable material and/or type of material that is known or developed in the future that is capable of being sterilized. Further, the connector 5702 may include any suitable connector and/or type of connector that is known or developed in the future capable of connecting the positioning device 5400 and the distraction body 5708.

In some embodiments, the connector 5702 is expandable and contractable. For example, FIG. 57A shows a set of connectors 5702 in a contracted position while connecting the positioning device 5400 and the distraction body 5708. In an additional or alternative example, FIG. 57B shows the set of connectors 5702 in an expanded position while connecting the positioning device 5400 and the distraction body 5708.

The set of connectors 5702 may be moved from the contracted position to the expanded position and vice versa using any suitable mechanism and/or technique that is known or developed in the future. In some embodiments, the set of connectors 5702 may be slid from the contracted position to the expanded position and vice versa.

Further, the set of connectors 5702 may be moved from the contracted position to one of a plurality of expanded positions. Here, the degree and/or length to which the set of connectors 5702 are expanded or slid open is dependent upon the corresponding size/length of the subject's metatarsal and/or the position desired for use in a bunion surgery and/or procedure.

Additionally, the set of connectors 5702 may be locked in the contracted position and/or in the expanded position, which locking can be performed using any suitable mechanism and/or technique that is known or developed in the future. In some embodiments, one or more fixation devices 5410 (e.g., K-wire(s) and/or olive wire(s)) can be used to lock the set of connectors 5702 in place by inserting the fixation device(s) 5410 through the aperture 5412 and into the subject's metatarsal 5902 (see, FIGS. 59A and 59B).

While the embodiment illustrated in FIGS. 57A and 57B show a set of connectors 5702 as including two (2) connectors 5702, the various embodiments are not limited to a pair or connectors 5702. That is, various other embodiments can include a single connector 5702 (e.g., one (1) connector 5702) or any suitable quantity of connectors 5702 greater that two connectors 5702 (e.g., three (3) connectors 5702, four (4) connectors 5702, five (5) connectors 5702, or more connectors 5702).

Figure 58:
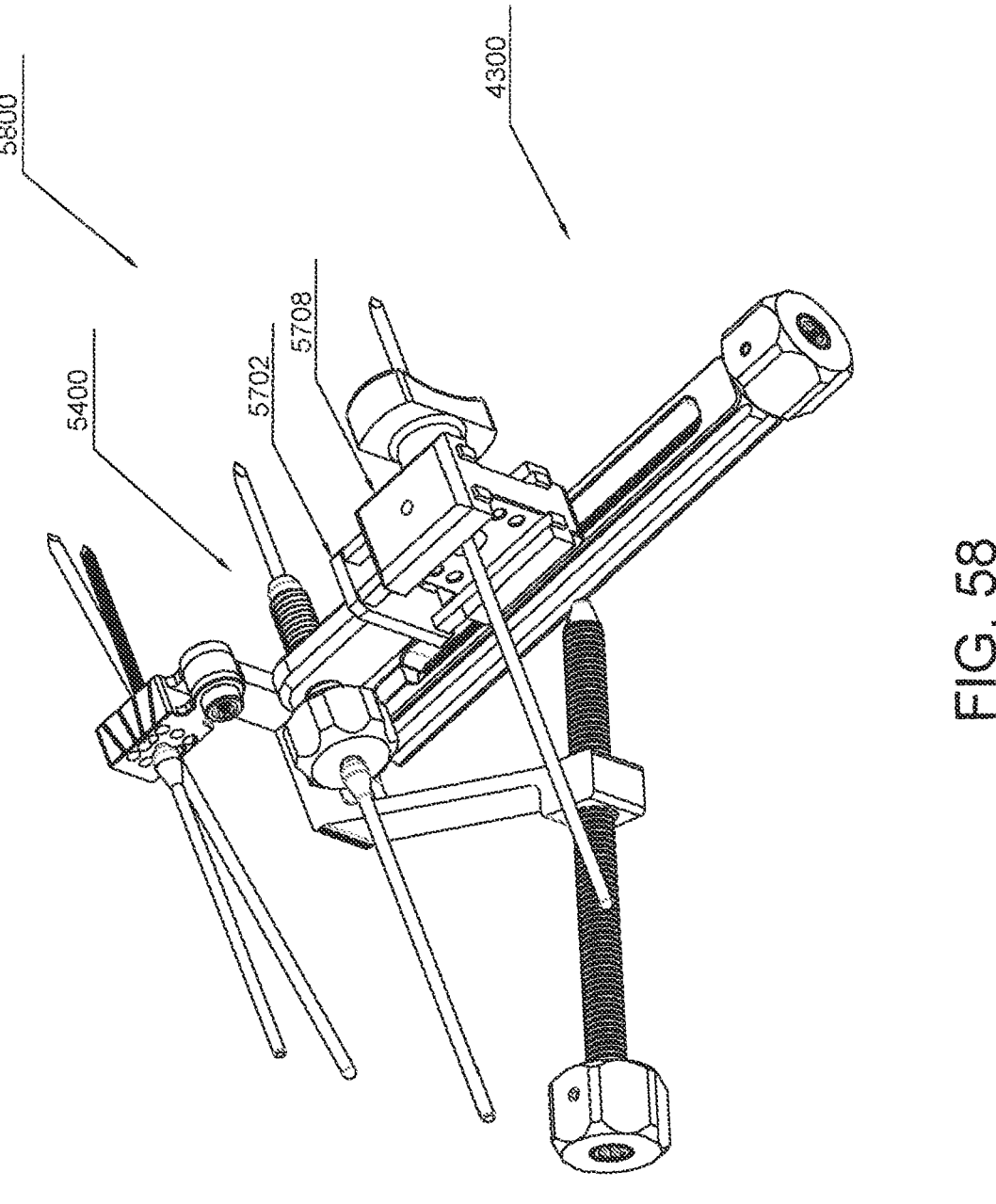
FIG. 58 is a diagram illustrating one embodiment of a surgical system including the surgical jig of FIG. 43 and the positioning device illustrated in FIGS. 57A and 57B.

FIG. 58 is a diagram illustrating another embodiment of a surgical system 5800 for use in performing an osteotomy. In certain embodiments, the osteotomy can include a procedure to correct a bunion.

At least in the illustrated embodiment, the surgical system 5800 includes, among other features, components, and/or elements, a surgical jig 4300 and a positioning device 5700. The surgical jig 4300 may include any embodiment of the surgical jig discussed herein.

In various embodiments, the positioning device 5800 can include the positioning device 5400A, the positioning device 5400B, or the positioning device 5400C. That is, while FIG. 58 shows the surgical system 5600 as including the positioning device 5400A, other embodiments can include the positioning device 5400B or the positioning device 5400C.

In some embodiments, the positioning device 5400 is detachably/releasably coupleable with the connector(s) 5702. In other embodiments, the positioning device 5400 is fixedly coupled to and/or forms at least a portion of the connector(s) 5702.

Figures 59A, 59B:
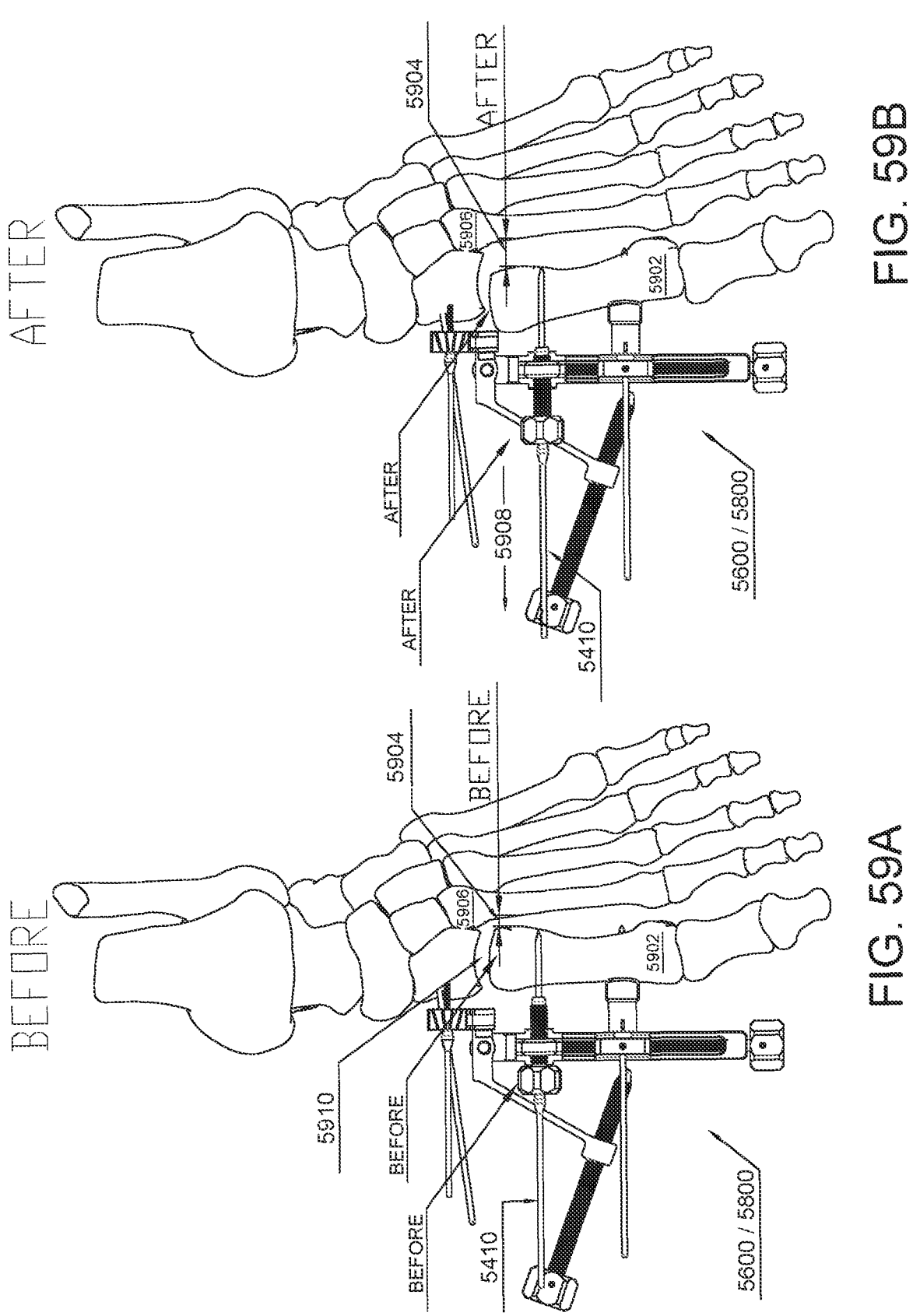
FIGS. 59A and 59B are diagrams illustrating one embodiment of operations of a positioning device of FIGS. 54A through 54C and/or FIGS. 57A and 57B.

With reference to FIGS. 59A and 59B, FIGS. 59A and 59B illustrate before and after illustrations of at least a portion of an osteotomy to correct a bunion. As illustrated, the fixation device 5410 has previously been inserted into the first metatarsal 5902 (e.g., a first bone) of a subject.

In FIG. 59A, a gap or space 5904 exists between the first metatarsal 5902 and a second metatarsal 5906 (e.g., a second bone). The space 5904 at this point in time can be considered and/or referred to as a small, relatively small, or smaller space 5904.

In FIG. 59B, a negative force 5908 being applied to the fixation device 5410 causes the fixation device 5410 to laterally move/pull the first metatarsal 5902 in the direction of the force 5908, which can be considered a negative direction in a transverse plane and/or a lateral plane. As the first metatarsal is moved in the negative direction along the transverse plane and/or the lateral plane, the first metatarsal is moved away from the second metatarsal 5906 enlarging the space 5904. The space 5904 at this point in time can be considered and/or referred to as a large, relatively large, or larger space 5904.

The force 5908 applied to the fixation device 5410, in some embodiments, is applied by a tuner (e.g., tuner 5408A), a positioning device 5400A, a tuner (e.g., a tuner 5408B), a positioning device 5400B, or a positioning device 5800. In additional or alternative embodiments, a positioning device 5400C applies the force 5908 and/or facilitates application of the force 5908 to the fixation device 5410, which force can be mechanically or manually applied (e.g., by a healthcare professional).

Figure 60:
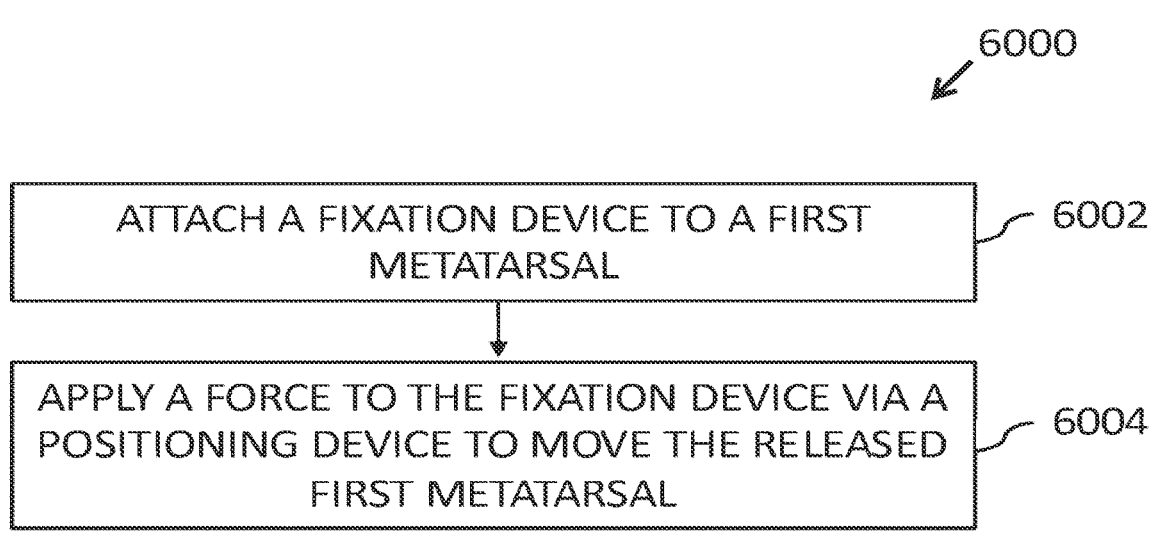
FIGS. 60 through 62 flow are flow diagrams illustrating various embodiments of a method for positioning and/or moving a bone during an osteotomy.

FIG. 60 is a flow diagram illustrating one embodiment of a method 6000 for positioning and/or moving a bone during an osteotomy. At least in the illustrated embodiment, the method 6000 can begin by attaching and/or coupling a fixation device 5410 to a first metatarsal 5902 or other bone (block 6002).

The fixation device 5410 may include any embodiment of a fixation device 5410 discussed elsewhere herein. Further, the fixation device 5410 can be attached/coupled to the first metatarsal 5902 or bone using any embodiment of a positioning device 5400A, 5400B, or 5400C and/or any embodiment of a tuner 5408A or 5408B.

A force 5708 is applied, via the positioning device 5400A, 5400B, or 5400C, to the first metatarsal 5902 or bone to move the first metatarsal 5902 (block 6004). The force 5908 can be a rotational force and/or a sliding force in a negative direction in a lateral plane and/or transverse plane, as discussed elsewhere herein.

In some embodiments, applying the force 5908 moves the first metatarsal 5902 from a first or original position to a second or new position, which can include a corrected position. In this manner, the first metatarsal 5902 is moved away from the second metatarsal 5906 to create space 5904 and/or to increase the size and/or amount of space 5904 between the first metatarsal 5902 and the second metatarsal 5906.

Figure 61:
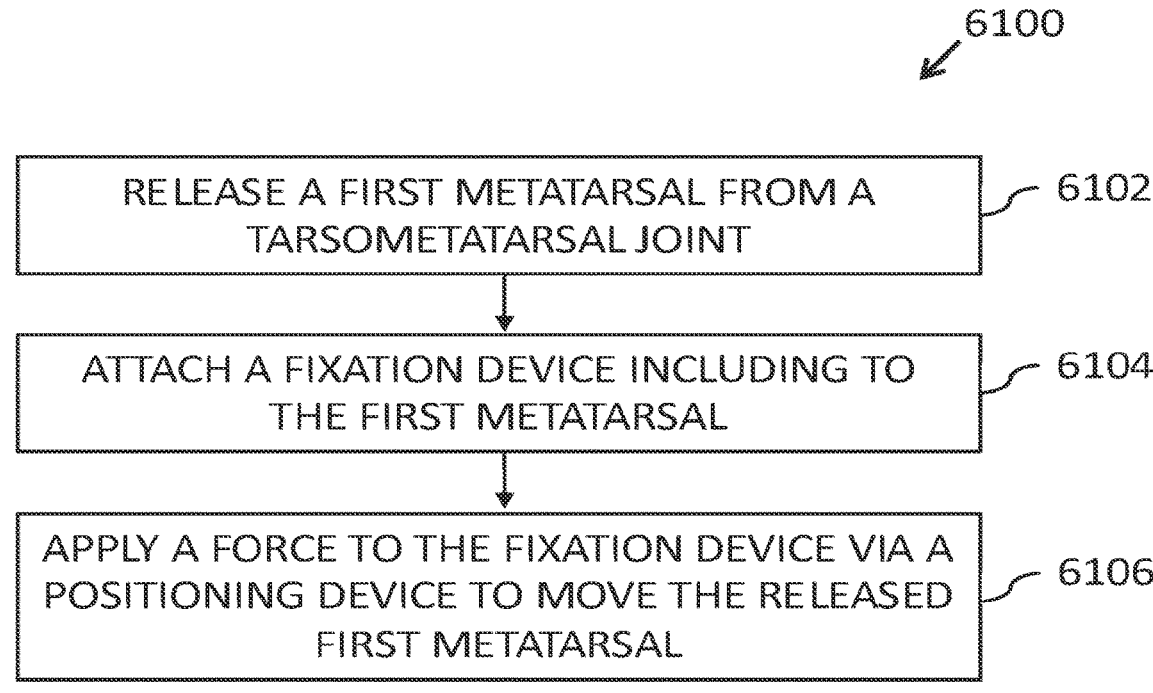

FIG. 61 is a flow diagram illustrating another embodiment of a method 6100 for positioning and/or moving a bone during an osteotomy. At least in the illustrated embodiment, the method 6100 can begin by releasing a first metatarsal 5902 or bone from a tarsometatarsal joint 5910 (see, FIGS. 59A and 59B) or other joint (block 6102). The first metatarsal 5902 can be released by, for example, cutting the first metatarsal 5902 from the tarsometatarsal joint 5910.

A fixation device 5410 is attached and/or coupled to the released first metatarsal 5902 or other bone (block 6104). The fixation device 5410 may include any embodiment of a fixation device 5410 discussed elsewhere herein. Further, the fixation device 5410 can be attached/coupled to the first metatarsal 5902 or bone using any embodiment of a positioning device 5400A, 5400B, or 5400C and/or any embodiment of a tuner 5408A or 5408B.

A force 5908 is applied, via the positioning device 5400A, 5400B, or 5400C, to the released first metatarsal 5902 or bone to move the first metatarsal 5902 (block 6106). The force 5908 can be a rotational force and/or a sliding force in a negative direction in a lateral plane and/or transverse plane, as discussed elsewhere herein.

In some embodiments, applying the force 5908 moves the released first metatarsal 5902 from a first or original position to a second or new position, which can include a corrected position. In this manner, the released first metatarsal 5902 is moved away from the second metatarsal 5906 to create space 5904 and/or to increase the size and/or amount of space 5904 between the released first metatarsal 5902 and the second metatarsal 5906.

Figure 62:
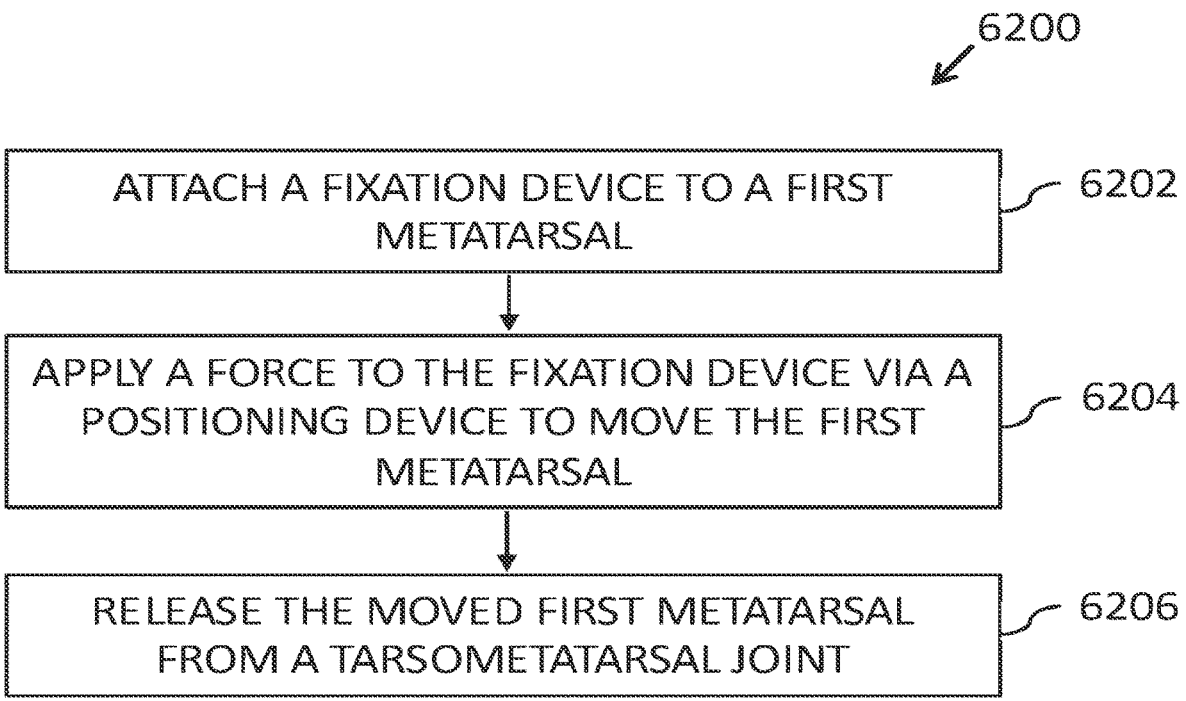

FIG. 62 is a flow diagram illustrating yet another embodiment of a method 6200 for positioning and/or moving a bone during an osteotomy. At least in the illustrated embodiment, the method 6200 can begin by attaching and/or coupling fixation device 5410 to a first metatarsal 5902 or other bone (block 6202).

The fixation device 5410 may include any embodiment of a fixation device 5410 discussed elsewhere herein. Further, the fixation device 5410 can be attached/coupled to the first metatarsal 5902 or bone using any embodiment of a positioning device 5400A, 5400B, 5400C and/or any embodiment of a tuner 5408A or 5408B.

A force 5908 is applied, via the positioning device 5400A, 5400B, or 5400C, to the first metatarsal 5902 or bone to move the first metatarsal 5902 (block 6204). The force 5908 can be a rotational force and/or a sliding force in a negative direction in a lateral plane and/or transverse plane, as discussed elsewhere herein.

In some embodiments, applying the force 5908 moves the first metatarsal 5902 from a first or original position to a second or new position, which can include a corrected position. In this manner, the first metatarsal 5902 is moved away from the second metatarsal 5906 to create space 5904 and/or to increase the size and/or amount of space 5904 between the first metatarsal 5902 and the second metatarsal 5906.

The moved first metatarsal 5902 or bone is released from a tarsometatarsal joint 5910 (see, FIGS. 59A and 59B) or other joint (block 6206). The moved first metatarsal 5902 can be released by, for example, cutting the moved first metatarsal 5902 from the tarsometatarsal joint 5910.

Figure 63:
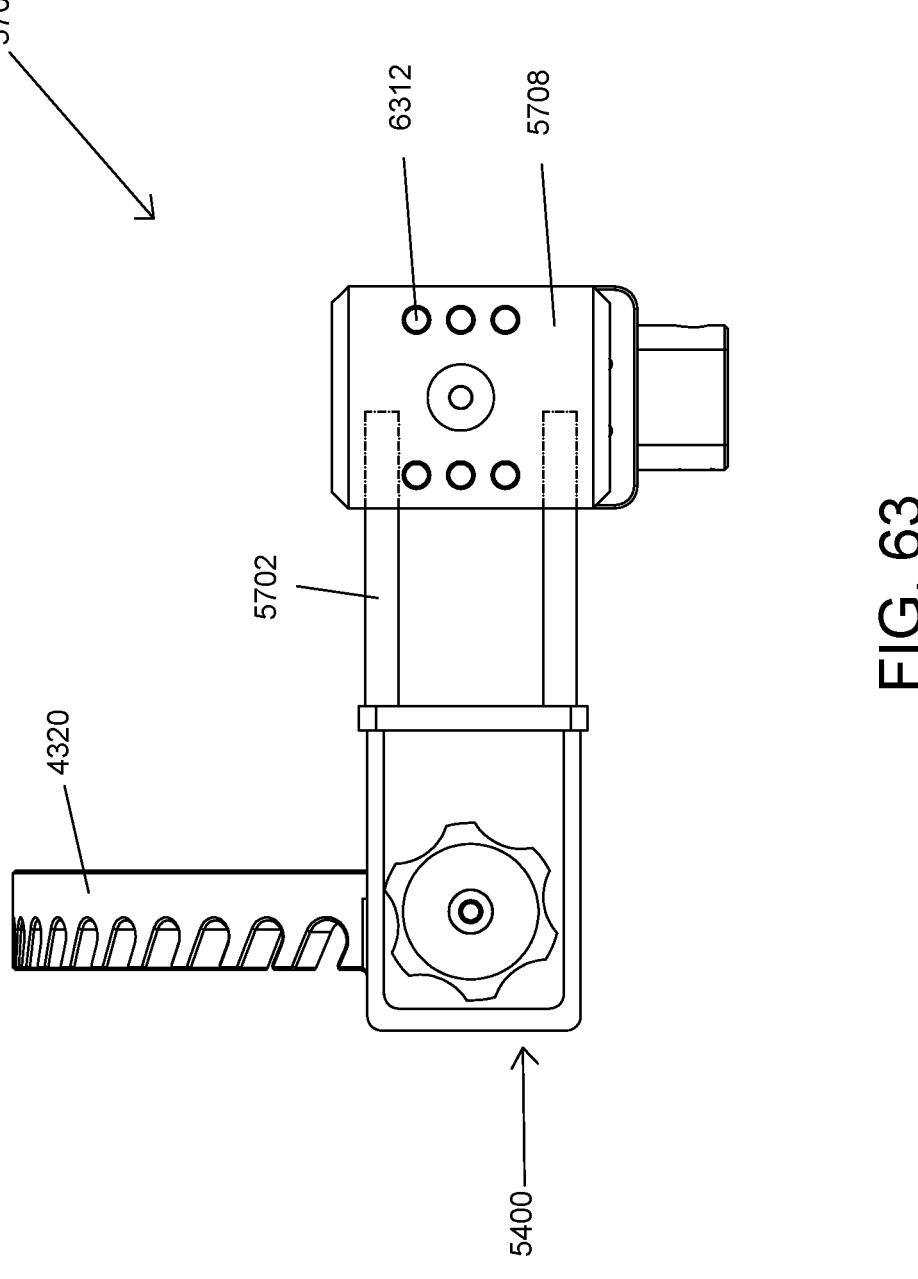
FIG. 63 is a diagram illustrating one embodiment of a moveable positioning device.

FIG. 63 is a diagram illustrating another embodiment of positioning device 5700. At least in the illustrated embodiment, the positioning device 5700 includes, among other elements and/or features, a positioning device 5400, a set of one or more connectors 5702, a distraction body 5708, and a rotation guide 4320. The rotation guide 4320 may be coupled to, detachably coupled to, or at least partially integral with the positioning device 5400. The rotation guide 4320 may be coupled to, detachably coupled to, or at least partially integral with the connectors 5702. The rotation guide 4320 may be coupled to, detachably coupled to, or at least partially integral with the distraction body 5708.

Figure 64:
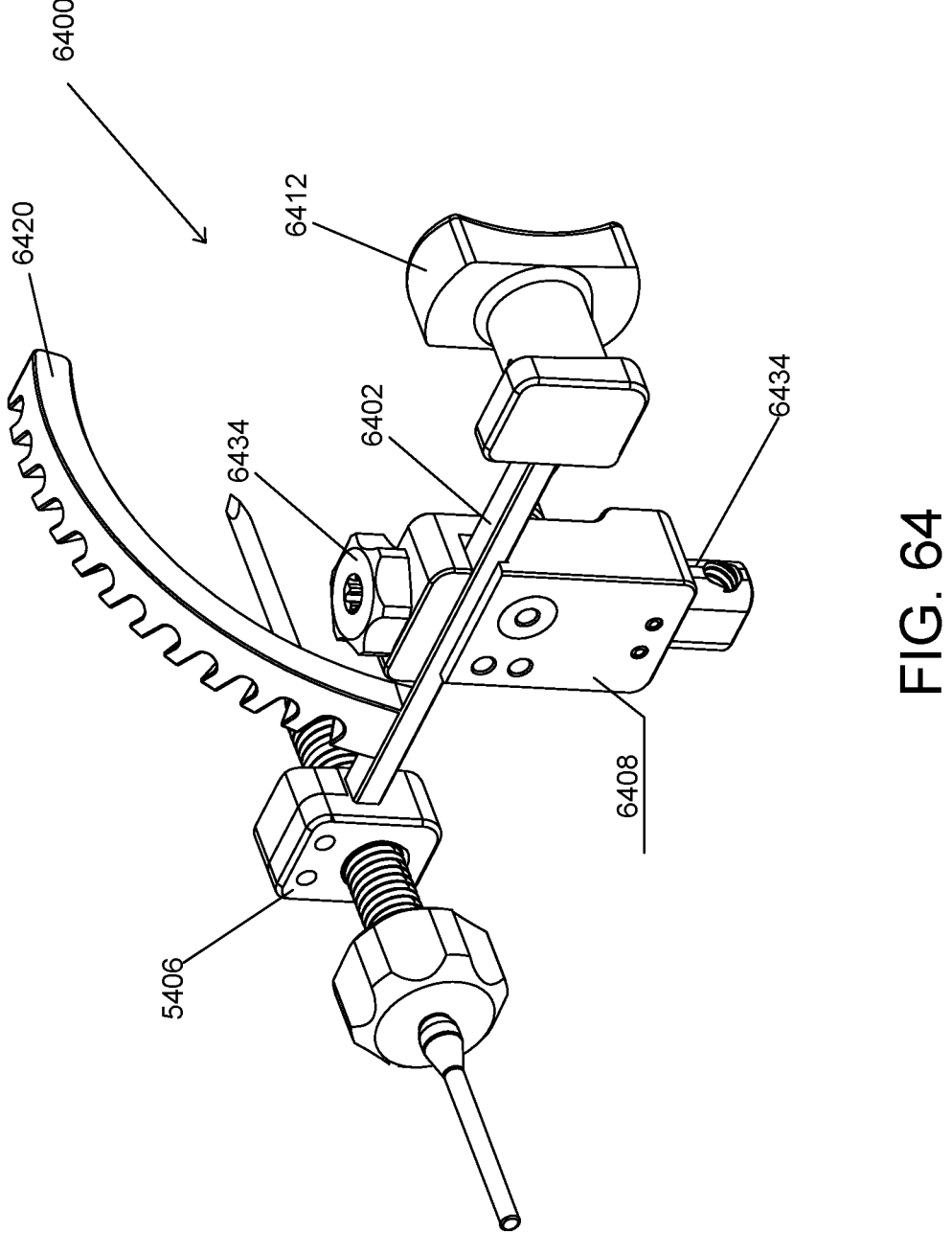
FIG. 64 is a diagram illustrating one embodiment of a surgical system including a positioning device, distraction body, and rotation guide.

FIG. 64 is a diagram illustrating another embodiment of positioning device 6400 for use in performing an osteotomy. In certain embodiments, the osteotomy can include a procedure to correct a bunion.

The positioning device 6400, in some embodiments, is an independent device that is capable of being attached and detached (e.g., is detachably coupleable) to a surgical device and/or instrument (e.g., surgical jig 4300). In additional or alternative embodiments, the positioning device 6400 is fixed, coupled to, and/or forms at least a portion of a surgical jig 4300.

At least in the illustrated embodiment, the positioning device 6400 includes, among other elements and/or features, a positioning device 5400, a set of one or more connector(s) 6402, a distraction body 6408, a metatarsal contact 6412, and a rotation guide 6420. The positioning device 5400 may include any embodiment of positioning device 5400A, positioning device 5400B, and/or positioning device 5400C discussed elsewhere herein. The connector(s) 6402 may include any embodiment of connectors 5702 discussed elsewhere herein. The distraction body 6408 may include any embodiment of a distraction body 4308 discussed elsewhere herein. The metatarsal contact 6412 may include any embodiment of a metatarsal contact 4312 discussed elsewhere herein. The rotation guide 6420 may include any embodiment of rotation guide 4320 discussed elsewhere herein.

The positioning device 5400 may be coupled to, detachably coupled to, or at least partially integral with the connector(s) 6402. The distraction body 6408 may be coupled to, detachably coupled to, or at least partially integral with the connector(s) 6402. The metatarsal contact 6412 may be coupled to, detachably coupled to, or at least partially integral with the connector(s) 6402. The rotation guide 6420 may be coupled to, detachably coupled to, or at least partially integral with the connector(s) 6402. The positioning device 5400, the rotation guide 6420, the distraction body 6408, and/or the metatarsal contact 6412 can be coupled to the connector(s) 6402 in any order and/or configuration. The positioning device 5400, the rotation guide 6420, the distraction body 6408, and/or the metatarsal contact 6412 may be coupled to the connector(s) 6402 at any location on the connector(s) 6402.

The location of the positioning device 5400 on the connector(s) 6402 may be set by a securing device 6434. The location of the rotation guide 6420 on the connector(s) 6402 may be set by the securing device 6434. The location of the distraction body 6408 on the connector(s) 6402 may be set by the securing device 6434. The location of the metatarsal contact 6412 on the connector(s) 6402 may be set by the securing device 6434. The securing device 6434 may include any embodiment of securing device 5402 discussed elsewhere herein. The securing device 6434 may comprise a screw, a set screw, a locking screw, a bolt, a locking bolt, a nut, a rivet, a detent, and/or magnet, along with other devices that are possible and contemplated herein. The securing device may set the location of at least two of the position device 5400, the rotation guide 6420, the distraction body 6408, and the metatarsal contact 6412 on the connector(s) 6402 simultaneously or individually.

The securing device 6434, the positioning device 5400, the rotation guide 6420, the distraction body 6408, the metatarsal contact 6412 and/or the connector(s) 6402 may include a set of complimentary shaped devices (e.g., notches and tab(s), hook and eye, detent, along with other shapes that are possible and contemplated herein) that allow for the coupling, setting, and/or removal of the positioning device 5400, the rotation guide 6420, the distraction body 6408, the metatarsal contact 6412 with/from the connector(s) 6402.

Figure 65A:
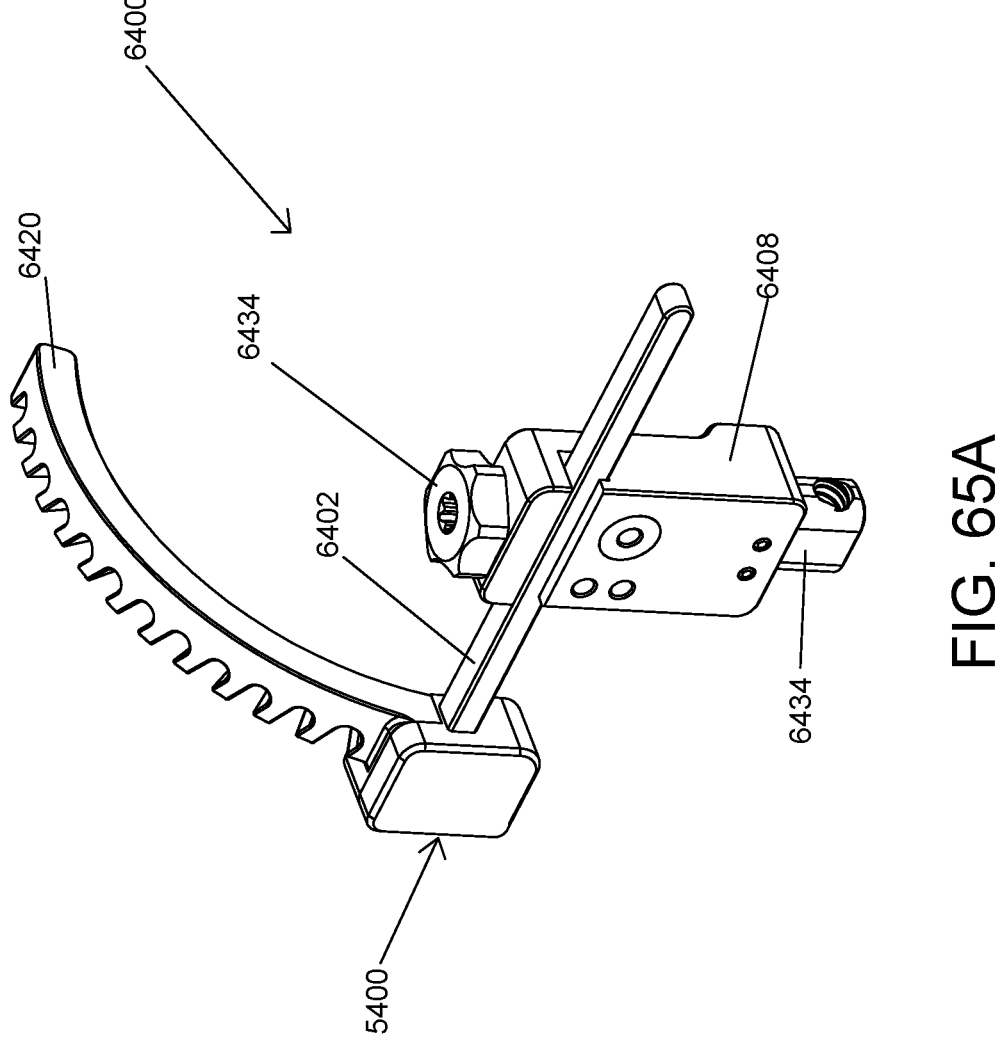
FIG. 65A-65C are diagrams illustrating various embodiments of a surgical system including a positioning device, distraction body, and rotation guide.
Figure 65B:
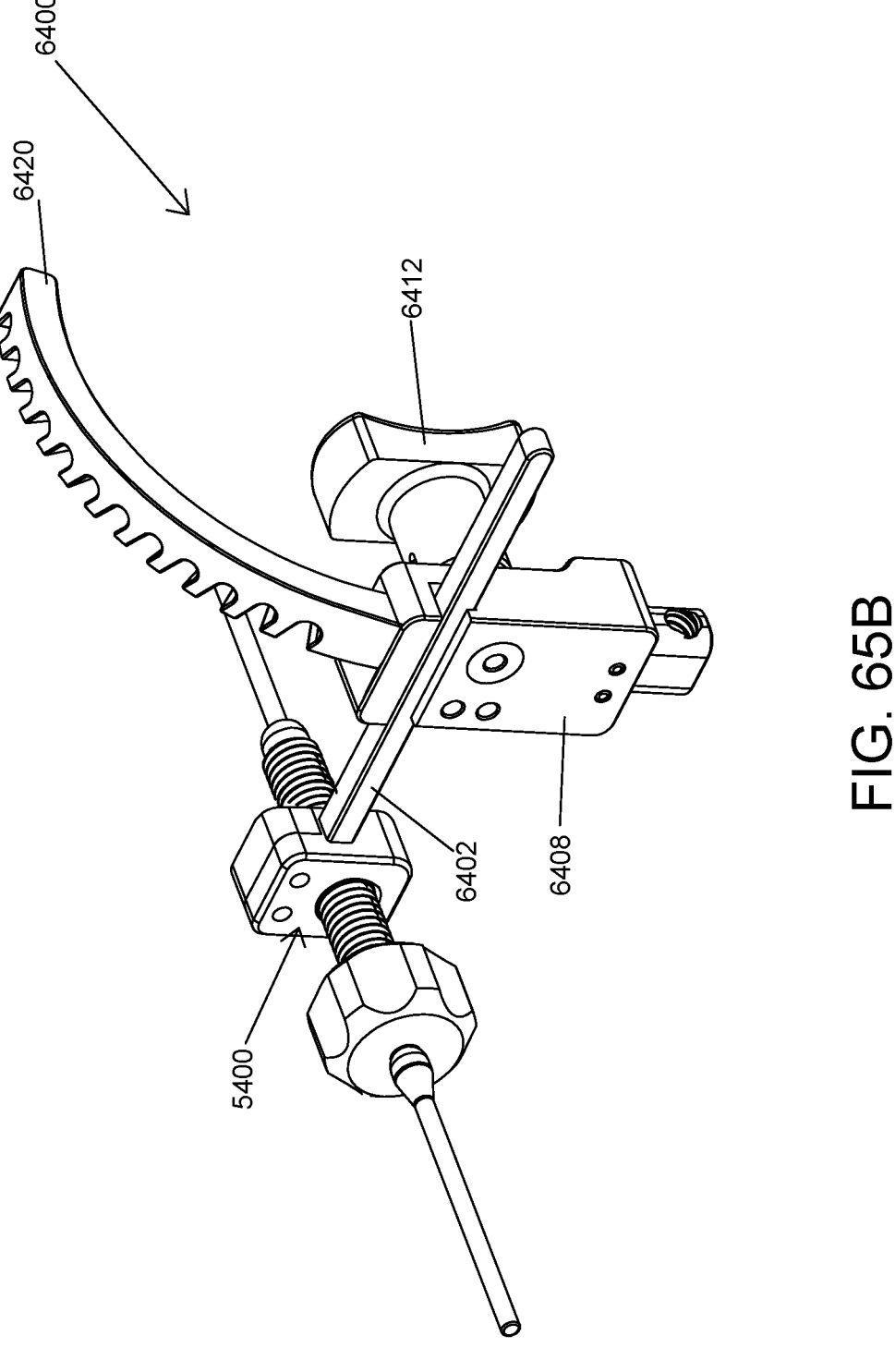
Figure 65C:
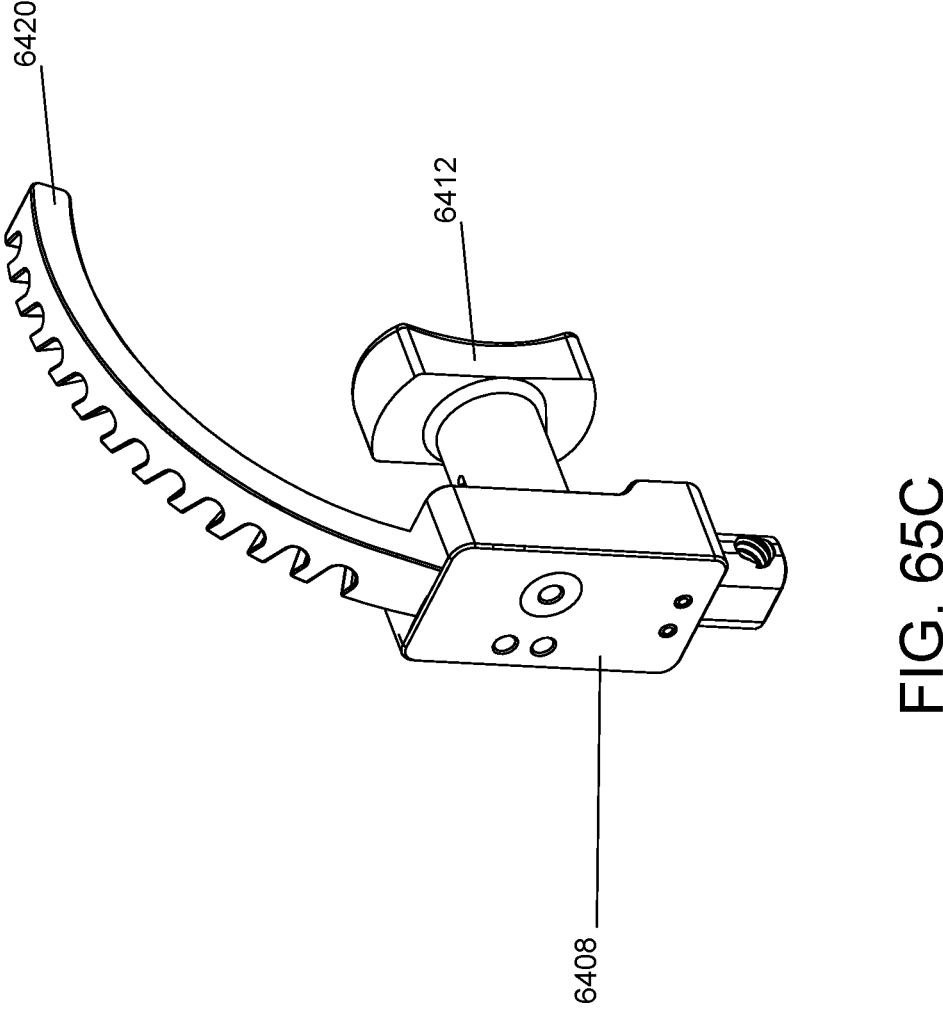

FIG. 65A is a diagram illustrating another embodiment of positioning device 6400. At least in the illustrated embodiment, the positioning device includes, among other elements and/or features, the positioning device 5400, the rotation guide 6420, the distraction body 6408, the metatarsal contact 6412, the connector(s) 6402, and/or at least one securing device 6434. In at least one embodiment the positioning device 5400, the rotation guide 6420, the distraction body 6408, and/or the metatarsal contact 6412 may be coupled to, detachably coupled to, or at least partially integral with each other. For example, at least in the illustrated embodiment, the positioning device 5400 is coupled to, detachably coupled to, or at partially integral with the rotation guide. FIG. 65B is a diagram illustrating another embodiment of positioning device 6400, wherein the rotation arm 6420, and the distraction body 6408, may be coupled, detachably coupled, or at least partially integral. FIG. 65C is a diagram illustrating another embodiment of positioning device 6400, wherein the rotation arm 6420 may be coupled to, detachably coupled to, or at least partially integral with the distraction body 6408.

Figure 66:
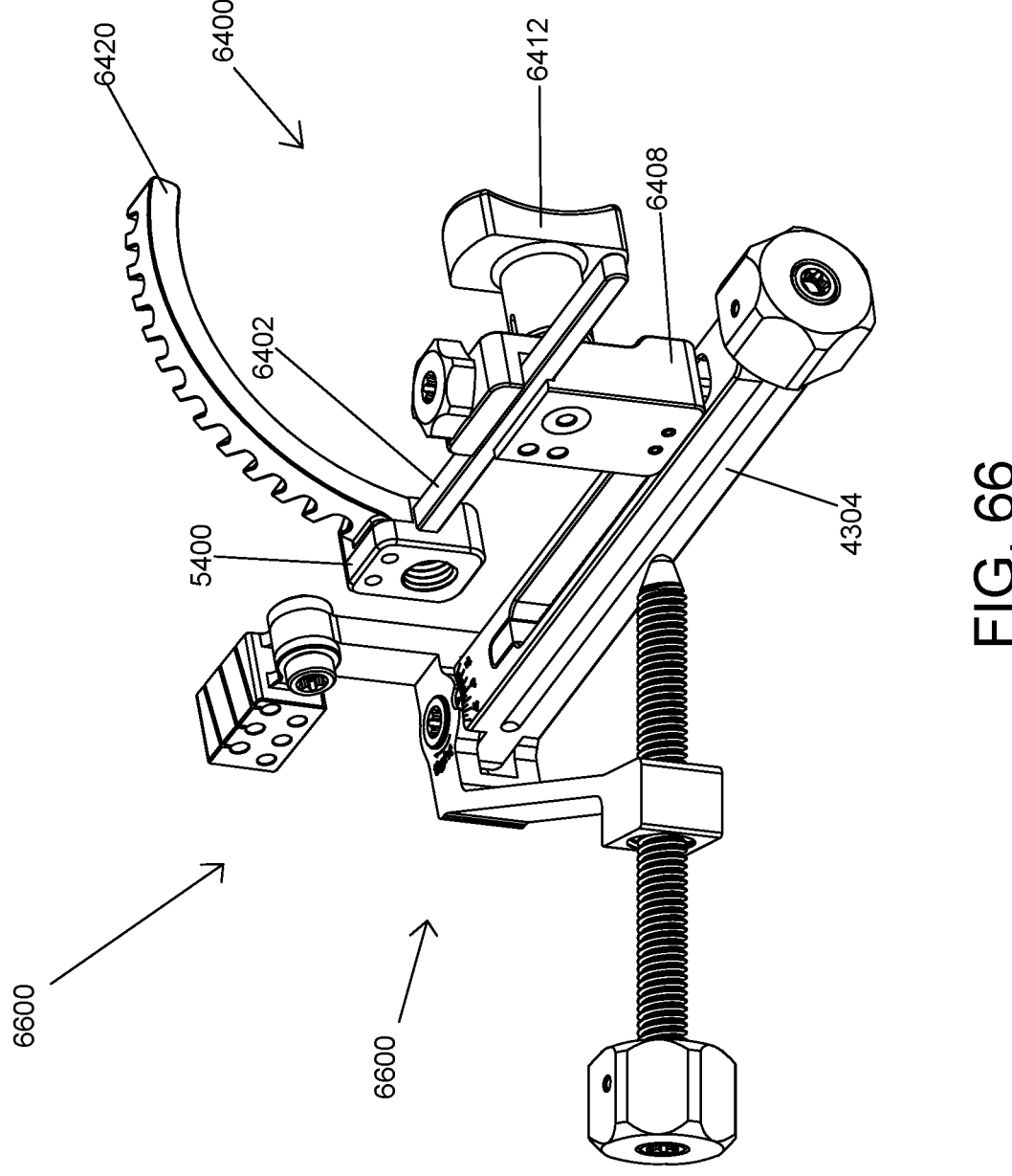
FIG. 66 is a diagram illustrating one embodiment of a surgical system including the surgical jig, a positioning device, distraction body, and rotation guide.

FIG. 66 is a diagram illustrating another embodiment of a surgical system 6600 for use in performing an osteotomy. In certain embodiments, the osteotomy can include a procedure to correct a bunion.

At least in the illustrated embodiment, the surgical system 6600 includes, among other features, components, and/or elements, a surgical jig 4300 and a positioning device 6400. The surgical jig 4300 may include any embodiment of the surgical jig 4300 discussed herein. The positioning device 6400 may include any embodiment of the positioning device 6400 discussed herein.

Figure 67:
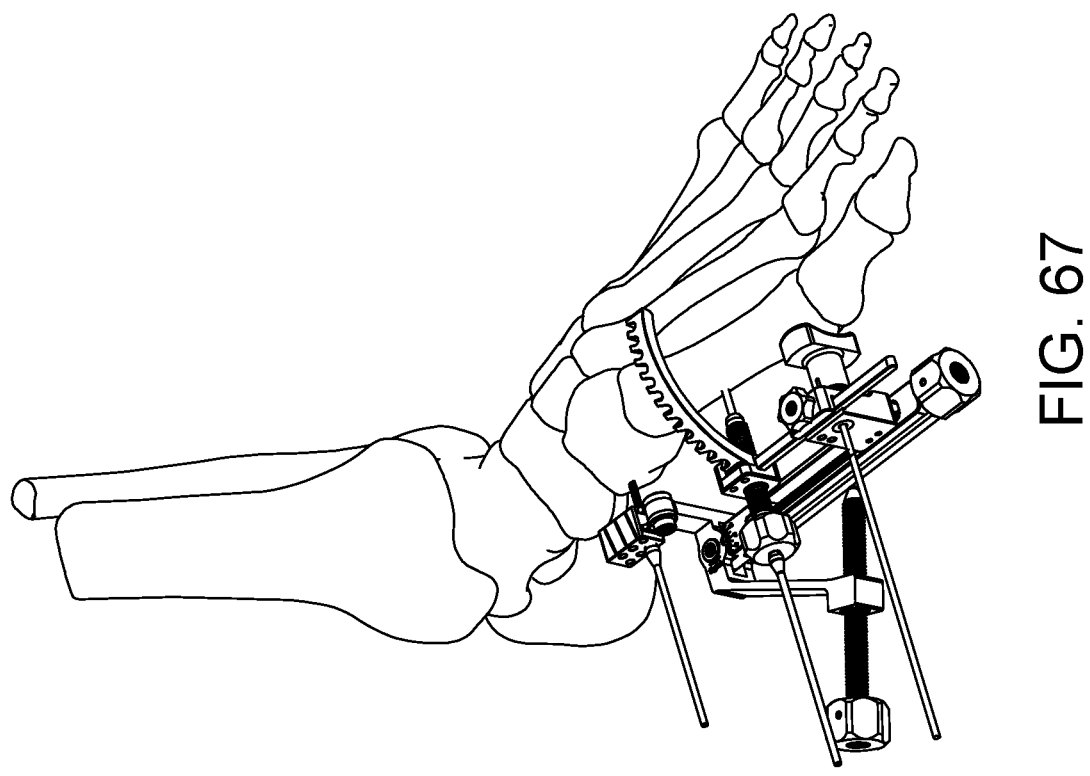
FIG. 67 is a diagram illustrating one embodiment of a surgical system including a positioning device, distraction body, and rotation guide on a foot.

FIG. 67 illustrates the positioning device 6400 coupled to the surgical jig 4300 and coupled to a foot. At least in the illustrated embodiment the alignment of the first metatarsal has been corrected in the transverse, sagittal, and frontal planes. Embodiments may be practiced in other specific forms. The described embodiments are to be considered in all respects only as illustrative and not restrictive. The scope of the various embodiments and/or invention is, therefore, indicated by the appended claims rather than by the foregoing description. All changes which come within the meaning and range of equivalency of the claims are to be embraced within their scope.

The invention claimed is:

1. An apparatus operable for performing an osteotomy for correction of a bunion, comprising:
    a surgical instrument;
    a distraction body coupled to the surgical instrument and configured to move along the surgical instrument in response to a force being applied to the distraction body;
    at least one connector configured to engage the distraction body; and
    a positioning body coupled to the connector;
    wherein the positioning body comprises a first aperture;
    a tuner, wherein:
        the first aperture is configured to receive the tuner; and
        the tuner comprises an elongated body and a second aperture configured to receive at least one fixation device for engaging at least a portion of a metatarsal.

2. The apparatus of claim 1,
    further comprising a rotation arm coupled to at least one connector.

3. The apparatus of claim 2,
    wherein the rotation arm is coupled to the at least one connector via the positioning body.

4. The apparatus of claim 3, wherein the distance between the distraction body and the positioning body is adjustable.

5. An apparatus operable for performing an osteotomy for correction of a bunion, comprising:
    a surgical instrument;
    a distraction body couplable to the surgical instrument and configured to move along the surgical instrument in response to a force being applied to the distraction body;
    a connector configured to engage the distraction body;
    a positioning body couplable to the connector;
    a tuner, wherein the positioning body comprises a first aperture configured to receive the tuner, and the tuner comprises a second aperture configured to receive at least one fixation device for engaging at least a portion of a metatarsal;

a rotation arm couplable to the connector, wherein the rotation arm is couplable to the connector via the positioning body; and wherein the distance between the distraction body and the positioning body is adjustable.

6. The apparatus of claim 4, wherein the first aperture includes threads and an exterior surface of the tuner includes threads, wherein the first aperture threads are configured to interact with the tuner exterior surface threads such that as the tuner is rotated the elongated body moves through the first aperture.

7. The apparatus of claim 6, wherein the tuner includes a knob at a first end of the elongated body.

8. The apparatus of claim 7, wherein the at least one connector is a single connector.

9. The apparatus of claim 8, wherein the distraction body is removable from the surgical instrument.

10. The apparatus of claim 9, wherein the connector is removable from the distraction body.

11. The apparatus of claim 10, wherein the connector is integral with the positioning body.

12. The apparatus of claim 2, wherein the rotation arm is removable from the connector.

* * * * *